United States Patent
Gueguen et al.

(10) Patent No.: US 10,773,978 B2
(45) Date of Patent: Sep. 15, 2020

(54) METHODS AND USES OF DISSOLVED ORGANIC MATERIAL FRACTIONS FOR BINDING METAL IONS

(71) Applicant: NOBLEGEN INC., Peterborough (CA)

(72) Inventors: Celine Gueguen, Sherbrooke (CA); Vaughn Mangal, Ajax (CA)

(73) Assignee: Noblegen, Inc., Peterborough, Ontario (CA)

( * ) Notice: Subject to any disclaimer, the term of this patent is extended or adjusted under 35 U.S.C. 154(b) by 0 days.

(21) Appl. No.: 16/326,541

(22) PCT Filed: Aug. 18, 2017

(86) PCT No.: PCT/CA2017/050984
§ 371 (c)(1),
(2) Date: Feb. 19, 2019

(87) PCT Pub. No.: WO2018/032115
PCT Pub. Date: Feb. 22, 2018

(65) Prior Publication Data
US 2019/0210898 A1    Jul. 11, 2019

Related U.S. Application Data

(60) Provisional application No. 62/513,018, filed on May 31, 2017, provisional application No. 62/377,323, filed on Aug. 19, 2016.

(51) Int. Cl.
*C02F 1/68* (2006.01)
*C02F 1/62* (2006.01)
(Continued)

(52) U.S. Cl.
CPC .............. *C02F 1/683* (2013.01); *C02F 1/62* (2013.01); *C12P 1/00* (2013.01); *C02F 3/322* (2013.01);
(Continued)

(58) Field of Classification Search
CPC ........ C02F 1/683; C02F 1/62; C02F 2103/20; C02F 3/322; C02F 2103/10; C02F 2101/20; C12P 1/00
(Continued)

(56) References Cited

U.S. PATENT DOCUMENTS 8,308,944 B2   11/2012   Horst
8,663,953 B2   3/2014   Behrens et al.
(Continued)

FOREIGN PATENT DOCUMENTS

CA   2103495 A1   5/1994
CA   2166717 A1   1/1995
(Continued)

OTHER PUBLICATIONS

Dieguez et al., Influence of dissolved organic matter character on mercury incorporation by planktonic organisms: An experimental study using oligotrophic water from Patagonian lakes, (2013), Journal of Environmental Sciences, pp. 1980-1991.*
(Continued)

*Primary Examiner* — Fred Prince
(74) *Attorney, Agent, or Firm* — Troutman Pepper Hamilton Sanders LLP

(57) ABSTRACT

The present application discloses a method of binding a metal ion in water. The method comprises contacting the water with a fraction of dissolved organic material (DOM) to form a complex between the DOM fraction and the metal ion; and optionally separating the complex from the water. The present application also discloses a use of DOM for binding a metal ion in water.

17 Claims, 57 Drawing Sheets

(51) Int. Cl.
  *C12P 1/00*    (2006.01)
  *C02F 3/32*    (2006.01)
  *C02F 101/20*  (2006.01)
  *C02F 103/20*  (2006.01)
  *C02F 103/10*  (2006.01)

(52) U.S. Cl.
  CPC ...... *C02F 2101/20* (2013.01); *C02F 2103/10* (2013.01); *C02F 2103/20* (2013.01)

(58) Field of Classification Search
  USPC ........................................ 210/684, 688, 602
  See application file for complete search history.

(56) References Cited

U.S. PATENT DOCUMENTS

| | | | |
|---|---|---|---|
| 8,951,773 B2 | 2/2015 | Kato et al. | |
| 9,045,785 B2 | 6/2015 | Pfeifer, III et al. | |
| 9,249,434 B2 | 2/2016 | Behrens et al. | |
| 9,457,108 B2 | 10/2016 | Schaap et al. | |
| 2010/0176065 A1* | 7/2010 | Looney | C02F 1/683 210/743 |
| 2011/0153213 A1* | 6/2011 | Buchanan | B09C 1/105 702/2 |
| 2017/0327427 A1* | 11/2017 | Blaney | C05B 7/00 |

FOREIGN PATENT DOCUMENTS

| | | |
|---|---|---|
| CN | 107673483 A | 2/2018 |
| DE | 3713882 A1 | 11/1988 |
| DE | 102010001907 A1 | 8/2011 |
| EP | 0288917 B1 | 9/1992 |
| EP | 1706500 B1 | 9/2010 |
| GB | 1395462 A | 5/1975 |
| WO | 2012151673 A1 | 11/2012 |
| WO | 2013138899 A1 | 9/2013 |
| WO | 2018032115 A1 | 2/2018 |
| WO | 2018184120 A1 | 10/2018 |

OTHER PUBLICATIONS

Miller et al., Influence of Dissolved Organic Matter on the Complexation of Mercury Under Sulfidic Conditions, (2007), Environmental Toxicology and Chemistry, vol. 26, No. 4, p. 624-633.*

Kumar et al., 2015. Green synthesis and characterization of silver nanoparticles using Andean blackberry fruit extract. Saudi Journal of Biological Sciences. 24(1):45-50.

Kurepa et al., 2014. Direct isolation of flavonoids from plants using ultra-small anatase TiO2 nanoparticles. The Plant Journal. 77(3):443-53.

Lancelot, C. 1984. Extracellular Release of Small and Large Molecules by P hytoplankton in the Southers Bight of the North Sea Estuaries, Coastal & Shelf Science. 18: p. 65-77.

Le Faucheur, S. et al. "Interactions between mercury and phytoplankton: speciation, bioavailability, and internal handling", Environmental Toxicology & Chemistry. 33(6): p. 1211-1224, 2014.

Leclerc, M. et al, "Relationship between Extracellular Low-Molecular-Weight Thiols and Mercury Species in Natural Lake Periphytic Biofilms", Environmental Science & Technology.49(13): p. 7709-7716, 2015.

Lehnherr et al.; 2011. Methylation of inorganic mercury in polar marine waters. Nat Geosci. 4:298-302.

Lemire et al.; Antimicrobial activity of Metals: Mechanism, Molecular Targets and Applications. Nat. Rev. Microbial 2016, 11, 371-384.

Levy, J et al., "Using diffusive gradients in thin films to probe the kinetics of metal interaction with algal exudates", Environmental Chemistry 8 (2011): 517-524.

Ma et al.; Mercury (II) Adsorption on Three Contrasting Chinese Soils Treated with Two Sources of Dissolved Organic Matter: II. Spectroscopic Characterization. Soil Sed. Cont.2015, 24, 719-730.

Malik, D. "Algal biomass as adsorbents for heavy metal sorption from aqueous solutions." Loughborough University nstitutional Repository. Doctoral Thesis. 1999.

Mangal et al., Molecular characterization of phytoplankton dissolved organic matter (DOM) and sulfur components ising high resolution Orbitrap Mass Spectrometry. Anal. Bioanal. Chem. 2016, 408 (7), 1891-1900.

Mangal et al.; Examining concentrations and molecular weights of thiols in microorganism cultures and in Churchill River (Manitoba) using a fluorescent-labeling method coupled to asymmetrical flow field-flow fractionation. Anal. Bioanal. Chem. 2015, 407, 4305-4313.

Mangal, V., "Assessing cadmium and vanadium accumulation using diffusive gradient in thin-films (DGT) and phytoplankton in the Churchill River estuary", Manitoba. Chemosphere. 163: p. 90-98, 2016.

Martone et al., 2009. Discovery of lignin in seaweed reveals convergent evolution of cell-wall architecture. Current Biology. 19(2): p. 169-175.

McIntyre, AM et al., "Binding interactions of algal-derived dissolved organic matter with metal ions.", Chemosphere 90 (2013): 620-626.

Michaelson et al., 2010. Viral trans-dominant manipulation of algal sphingolipids. Trends Plant Science. 15(12): p. 651-655.

Mierle et al.; The Role of Flumic Substances in the mobilization of Mercury from watersheds. Water Air Soil Pollut. 1991, 56 349-357.

Moreau et al.; The Effect of Natural Organic Matter on Mercury Methylation by Desulfobulbus propionicus I pr3. Front. Microbial. 2015, 6 (1389), 1-15.

Müller et al., 2006. Brunsvicamides A-C: Sponge-Related Cyanobacterial Peptides with Mycobacterium tuberculosis Protein Tyrosine Phosphatase Inhibitory Activity. J. Med. Chem. 49, 4871-4878. doi:10.1021/jm0060327w.

Muresan B. et al., "Measurement and modeling of mercury complexation by dissolved organic matter isolates from freshwater and effluents of a major wastewater treatment plant", Appl. Geochem. 2011, 26, 2057-2063.

Ndu et al.; Effect of Inorganic and Organic Ligands on the Bioavailability of Methylmercury as Determined by Using a mer-lux Bioreporter. App. Environ. Microbial. 2012, 78 (20), 7276-7282.

Ngu-Schwemlein et al., Synthesis and ESI mass spectrometric analysis of the association of mercury(II) with multi-cysteinyl peptides. J Inorg Biochem, 2014, 133, 8-23.

Oestreich et al.; Colored Dissolved Organic Matter in Shallow Estuaries: Relationships between Carbon sources and light attenuation. Biogeosciences. 2016, 13, 583-595.

Ohno et al., Influence of heteroatom pre-selection on the molecular formula assignment of soil organic matter components determined by ultrahigh resolution mass spectrometry. Anal. Bioanal. Chem., 2013, 405 (10), 3299-3306.

Percopo et al., 2013. A new potentially toxic Azadinium species (Dinophyceae) from the Mediterranean Sea, A. dexteroporum sp. nov. J. Phycol. 49, n/a-n/a, doi: 10.1111/jpy.12104.

Peuravuori et al.; ESI-MS analyses of Lake Dissolved Organic Matter in Light of Supramolecular Assembly. Anal. Bioanal Chem. 2007, 389, 1559-1568.

Pirastru et al., 2012. Long-term stress induced by nitrate deficiency, sodium chloride, and high light on photosystem II activity and carotenogenesis of green alga Scenedesmus sp. Botany. 90(10): p. 1007-1014.

Prince et al., 1983. The glucose effect in Bacillus subtilis. European Journal of Biochemistry. 134: 105-7.

Qi et al.. Absorption-Mode: The Next Generation of Fourier Transform Mass Spectra. Anal. Chem. 2012, 84, 2923-2929.

Quoc et al., "Identification of Organic Ligands in Dissolved Organic Matter Produced by Scenedesmus obliquus Using Fourier Transform Ion Cyclotron Resonance Mass Spectomerty", [powerpoint presented on May 29, 2017].

Rasala et al., 2015. Photosynthetic biomanufacturing in green algae; production of recombinant proteins for industrial, nutritional, and medical uses. Photosynthesis Research. 123(3): p. 227-239.

Ravichandran M., "Interactions between Mercury and Dissolved Organic Matter-A Review",. Chemosphere. 2004, 55:319-331.

(56) References Cited

OTHER PUBLICATIONS

Rehman, A., "Heavy Metals Uptake by Euglena proxima Isolated from Tannery Effluents and Its Potential Use in Wastewater Treatment", Department of Microbiology and Molecular Genetics, ISSN 1067-4136, Russian Journal of Ecology, 2011, vol. 42, No. 1, pp. 44-49.

Remucal et al., 2012. Low molecular weight components in an aquatic humic substance as characterized by membrane dialysis and orbitrap mass spectrometry. Environmental Science & Technology. 46(17): p. 9350-9359.

Riedel, T., "Molecular fractionation of dissolved organic matter with metal salts", Environ Sci Technol, 2012, 46, 4419-4426.

Rodriguez, MS et al., "Metal biosorption onto dry biomass of Arthrospira (Spirulina) platensis and Chlorella vulgaris: multi-metal systems.", Journal of Hazardous Materials 217 (2012): 246-255.

Rossolini et al., 2006. New beta-lactamases a paradigm for the rapid response of bacterial evolution in the clinical setting. Future Microbiology. 1(2): p. 295-308.

Roth et al., Latitude and pH driven trends in the molecular composition of DOM across a north south transect along the Yenisei River. Geochim Cosmochim Acta, 2013, 123, 93-105.

Roth et al., The molecular composition of dissolved organic matter in forest soils as a function of pH and temperature. PLoS One, 2013, 10 (3), 1-23.

Schaefer et al.; Effect of Divalent Metals on Hg (II) Uptake and Methylation by Bacteria. Environ. Sci. Technol. 2014, 48, 3007-3013.

Schartup A.T. et al., "Contrasting Effects of Marine and Terrestrially Derived Dissolved Organic Matter on mercury Speciation and Bioavailability in Seawater", Environ. Sci. Technol. 2015, 49, 5965-5972.

Schnitzer et al.; The alkaline hydrolysis of humic substances. Geoderma. 1975, 13, 171-188.

Schulze et al.; 2016. A one-stage cultivation process for lipid- and carbohydrate-rich biomass of Scenedesmus obtusiusculus based on artificial and natural water sources. Bioresource Technology. 218: p. 498-504.

Seitzinger S.P. et al., "Molecular-level chemical characterization and bioavailability of dissolved organic matter using electrospray ionization mass spectrometry", Limnol. Oceanogr. 2005, 50 (1), 1-12.

Selifonova et al.; Bioluminescent Sensors for Detection of Bioavailable Hg (II) in the Environment. Appl. Environ. Micro 1993, 59 (9), 3083-3090.

Singh P. K., 1975. Sensitization of algal virus to UV by the incorporation of 5-bromouracil and mutations of host alga Plectonema boryanum. Journal of Basic Microbiology. 75(7):547-52.

Sipler et al., 2017. Microbial Community Response to Terrestrially Derived Dissolved Organic Matter in the Coastal Arctic. Frontiers in Microbiology. 8(1018): p. 1018.

Smith et al.; 2005. Metlin-A metabolite mass spectral database. Therapeutic Drug Monitoring. 27(6): p. 747-751.

Smith, S.; Metal Speciation in Natural Waters with Emphasis on Reduced Sulfur Groups as Strong Metal Bindings Sites. Comp Biochem Phys C. 2002, 133, 65-74.

Solliec et al., Quantitative performance of liquid chromatography coupled to Q-Exactive high resolution mass spectrometry (HRMS) for the analysis of tetracyclines in a complex matrix. Anal Chim Acta, 2015, 853, 415-424.

100th Canadian Chemistry Conference and Exhibition (CSC 2017); see p. 11, "17:20"; Technical Program shows title only, May 28, 2017.

Abdel-Aal et al., 2015. Successive solvent extraction and GC-Ms analysis for the evaluation of the phytochemical constituents of the filamentous green alga Spirogyra longata. The Egyptian Journal of Aquatic Research. 41(3):233-46.

Aiken et al.; Dissolved Organic Matter in the Florida Everglades: Implications for Ecosystem Restoration. Environ. Sci. Technol. 2011, 41 (1), 271-248.

Aluwihare et al., 1997. A major biopolymeric components to DOC in surface sea water. Letters to Nature 387(8): p. 166-169.

Amon et al.; Photochemical and microbial consumption of dissolved organic carbon and dissolved oxygen in the Amazon River System. Geochimica. Cosmochim Acta. 1996, 60 (10), 41-51.

Baars et al., 2014. ChelomEx: Isotope-assisted discovery of metal chelates in complex media using high-resolution LC-Ms. Analytical Chemistry. 86(22): p. 11298-11305.

Baba et al., 2013. Biosynthesis of Lipids and Hydrocarbons in Algae, Photosynthesis: Agricultural and Biological Sciences. ISBN: 978-953-51/1161-0.

Bagwell et al., 2014. A diverse assemblage of indole- 3-acetic acid producing bacteria associated with unicellular green algae. Applied Biochemistry and Biotechnology. 173(8): 1977-84.

Balch J et al.; Effects of Molecular Weight on the Diffusion Coefficient of Aquatic Dissolved Organic Matter and Humic Substances. Chemosphere. 2015, 119, 498-503.

Barkay T. et al., "Effects of Dissolved Organic Carbon and Salinity on Bioavailability of Mercury", App. Environ. Micro.1997, 63 (11), 4267-4273.

Bauersachs. 2010. (Thesis) Development and application of proxies for past cyanobacterial N2 fixation.

Benoit et al.; Constants for Mercury Binding by Dissolved Organic Matter Isolates from the Florida Everglades. Geochim. Cosmochim. Acta. 2001, 65 (24), 4445-4451.

Bertrand, S.; Siderophore Base-The WebData Base of Microbial Siderophores. 2014.

Bronk et al., 2007. DON as a source of bioavailable nitrogen for phytoplankton. Biogeosciences. 4: p. 283-296.

Cabaniss S.E. et al., "A stochastic model for the synthesis and degradation of natural organic matter. Part I. Data structures and reaction kinetics", Biogeochem. 2005, 76, 319-347.

Chen, H, et al., Identification of Mercury and Dissolved Organic Matter Complexes Using Ultrahigh Resolution Mass Spectrometry. Environ. Sci. Technol. Lett., 2017, 4, 59-65.

Chiasson-Gould S.A. et al., "Dissolved Organic Matter Kinetically Controls Mercury Bioavailability", Environ. Sci. Technol. 2014, 48, 3153-3161.

Choi et al., 1987. Lipid content and fatty acid composition of green algae Scenedesmus obliquus grown in a constant cell density apparatus. Food Biotechnology. I (1): 117-28.

Cole et al.; Differential support of lake food webs by three types of ten-estrial carbon. Ecolo. Lett. 2006, 9 (5), 558-568.

Cortez-Rocha et al., 2002. Effect of extrusion processing on fumonisin B(I) and hydrolyzed fumonisin B(I) in contaminated alkali-cooked corm Bull Environ Contam Toxicol. 69(4): p. 471-478.

Cory et al.; Singlet Oxygen in the Coupled Photochemical and Biochemical Oxidation of Dissolved Organic Matter. Environ. Sci. Technol. 2010, 44, 3683-3689.

Cuss et al.; Impacts of Microbial Activity on the Optical and Copper-Binding Properties of Leaf-Litter Leachate. Front. Microbial. 2012, 3 (166), 1-10.

D' Andrilli et al.; Characterization of IHSS Pony Lake fulvic acid dissolved organic matter by electrospray ionization Fourier transform ion cyclotron resonance mass spectrometry and fluorescence spectroscopy. Org. Geochem. 2013, 65, 19-28.

Diez et al., 2016. Role of Settling Particles on Mercury Methylation in the Oxic Water Colunm of Freshwater Systems. Environmental Science & Technology. 50(21): p. 11672-11679.

Doran et al., A computer program to simplify analysis of mass scan data of organometallic compounds from high-resolution mass spectrometers. Rap. Comm. Mass Spec., 2016, 30, 2561-67.

Drexel et al.; Mercury (II) sorption to two Florida Everglades peats: evidence for strong and weak binding and competition by dissolved organic matter released from the peat. Environ. Sci. Technol.2002, 36 (19), 4058-4064.

Driscoll et al.; Mercury as a Global Pollutant: Sources,Pathways and Effects. Environ Sci. Technol. 2013, 47, 1967-4983.

Duong et al.; 2015. High protein- and high lipid-producing microalgae from northern Australia as potential feedstock for animal feed and biodiesel. Frontiers in Bioengineering & Biotechnology. 3(53): p. 1-7.

(56) References Cited

OTHER PUBLICATIONS

Dupont et al., 2004. Diurnal cycling of GSH in marine phytoplankton: Field and culture studies. Limnology and Oceanography. 49(4): p. 991-996.

Everall et al., 1997. The identification and signifigance of chemicals released from decomposing barley straw during reservoir algal control. Water Research. 31(3): p. 614-620.

Freire-Nordi, CS et al., "The metal binding capacity of Anabaena spiroides extracellular polysaccharide: an EPR study.", Process Biochemistry 40 (2005): 2215-2224.

Gonzalez-Davila, M et al., "Binding of Cu(II) to the Surface and Exudates of the Alga Dunaliella tertiolecta in Seawater.", Environmental Science & Technology 29 (1995): 289-301.

Graham et al.; Dissolved Organic Matter Enhances Microbial Mercury Methylation Under Sulfidic Conditions. Environ Sci. Technol. 2012, 46, 2715-2723.

Greene, "Removal of heavy metal ions from contaminated water by Chlorella vulgaris", 29th Annual New Mexico Water Conference Proceedings, WRRI Report No. 181, Jul. 1984.

Haitzer et al., 2002. Binding of Hg to DOM the role of the Hg DOM ratio. Environmental Science & Technology. 36: p. 3564-3570.

Hammer et al.; PAST: Paleontological Statistics Software Package for Education and Data Analysis. Palaeontol. Electron. 2001, 4 (1), 9.

Han et al.; 2008. Towards high-throughput metabolomics using ultrahigh-field Fourier transform ion cyclotron resonance mass spectrometry. Metabolomics. 4(2): p. 128-140.

Hasterberg et al.; Bonding of Hg (II) to reduced organic sulfur in humic acid as affected by S/Hg ratio. Environ. Sci. Technol. 2001, 35 (13), 2741-2745.

Hernes et al., 2007. Fractionation of lignin during leaching and sorption and implications for organic matter "freshness". Geophysical Research Letters. 34(17): p. 1-6.

Hider, R.C. et al., "Chemistry and biology of siderophores", Natural Product Reports. 27(5): p. 637-657, 2009.

Holguin at al., 2013. Characterization of microalgal lipid feedstock by direct-infusion FT-ICR mass spectrometry. Algal Research. 2(1): p. 43-50.

Hopkinson et al.; Terrestrial inputs of organic matter to Coastal Ecosystems: An Intercomparison of Chemical Characteristics and Bioavailability. Biogeochem. 1998, 43, 211-234.

Hughes et al., 1998. The thiol oxireductase ERp57 is a component of the MHC class I peptide-loading complex. Current Biology. 8(12):p. 709-713.

International Search Report and Written Opinion for PCT/CA2018/050431 dated Jul. 12, 2018.

Johnstone et al., 2015. Beyond iron: non-classical biological functions of bacterial siderophores. Dalton Transactions. 44(14): p. 6320-6339.

Kanehisa et al., 2000. KEGG-Kyoto Encyclopedia of Genes and Genomes. Nucleic Acids Research. 28(1): p. 27-30.

Kaplan, D et al., "Chelating properties of extracellular polysaccharides from Chlorella spp.", Applied and Environmental Microbiology 53 (1987): 2953-2956.

Kim et al.; Graphical Method dor Analysis of Ultrahigh-Resolution Broadband Mass Spectra of natural Organic Matter, the Van Krevelen Diagram. Anal. Chem. 2003, 75, 5336-5344.

Koch et al.; From mass to structure: An aromaticity Index for High-Resolution Mass Data of Natural Organic Matter. Rap. Comm. Mass. Spec. 2006, 20, 926-932.

Koukal, B et al., "Effect of Pseudokirchneriella subcapitata (Chlorophyceae) exudates on metal toxicity and colloid aggregation.", Water Research 41 (2007): 63-70. [Abstract].

Sun L., Perdue E.M. et al., "Use of Elemental Composition to Predict Bioavailability of Dissolved Organic Matter in Georgia River", Limnol. Oceanogr. 1997, 42 (4), 714-721.

Superville et al.; Identification and on-line monitoring of reduced sulfur species (RSS) by voltammetry in oxic waters. Talanta. 2013, 112, 55-62.

Thornton, D.C.O. "Dissolved organic matter (DOM) release by phytoplankton in the contemporary and future ocean", European Journal of Phycology. 49(1): p. 20-46, 2014.

Vestola et al., 2014. Hassallidins antifunfal glycolipopeptides are widespread among cyanobacteria and are the end product of a nonribsomal pathway. Proceedings of the National Academy of Sciences. 111 (18): E1909-17.

Ward et al., 2016. Complete and Partial Photo-oxidation of Dissolved Organic Matter Draining Permafrost Soils. Environmental Science & Technology. 50(7): p. 3545-3553.

Xia et al.; A. X-Ray Absorption Spectroscopic Evidence for the Complexation of Hg (II) by Reduced Sulfur in Soil Humic Substances. Environ. Sci. Technol. 1999, 33, 257-261.

Yamada, E et al. "Biodegradation of Dissolved Organic Matter released from Phytoplankton in Lake Biwa", Analytical Sciences. 28: p. 675-681, 2012.

Yamamoto et al., 2014. Determination of volatile compounds in four commercial samples of Japanese green algae using SPE GO-MS. The Scientific World Journal. 2014:1-8.

Yang et al.; Silver Nanoparticle Behavior, Uptake and Toxicity in Caenorhabditis elegans: Effect of Natural Organic Matter. Environ. Sci. Technol. 2014, 48, 3486-3495.

* cited by examiner

METHODS AND USES OF DISSOLVED ORGANIC MATERIAL FRACTIONS FOR BINDING METAL IONS

CROSS-REFERENCE TO RELATED APPLICATIONS

The present application claims the benefit of priority from U.S. provisional application nos. 62/377,323 filed on Aug. 19, 2016 and 62/513,018 filed on May 31, 2017, the contents of each of which are incorporated herein by reference in their entirety.

FIELD

The present application relates to methods of binding metal ions. For example, the present application relates to methods and uses of dissolved organic material for binding a metal ion in water such as wastewater.

BACKGROUND

Mercury (Hg) is a toxic metal that can disrupt natural enzymatic processes and cause cellular stress[1a]. In addition to being toxic as inorganic $Hg^{II}$, humans and wildlife are also exposed to the potent neurotoxin monomethylmercury (MMHg). Upon deposition from the atmosphere, $Hg^{II}$ first interacts with inorganic and organic ligands under oxic conditions. Furthermore, whereas microbial $Hg^{II}$ methylation to toxic MMHg occurs under anoxic conditions, recent reports suggest that methylation may not solely be limited to anoxic microbial habitats[1b]. Therefore, a comprehensive approach to studying $Hg^{II}$ pathways from the atmosphere to methylation sites requires that $Hg^{II}$ speciation and bioavailability to microbial cells be studied over a wide range of environments, including oxic freshwaters[2,13]. Such studies, characterizing dissolved organic matter (DOM) on a molecular level and how it interacts with $Hg^{II}$ are not known to have previously been disclosed. DOM is a complex mixture of heterogeneous material deriving from a variety of autochthonous and allochthonous sources that can, for example, act as a microbial nutrient source, affect light penetration in solution and chelate metals[3-7].

DOM has a very diverse and dynamic composition that, while not wishing to be limited by theory, may interact with $Hg^{II}$ in several ways. First, the binding of $Hg^{II}$ to DOM can decrease its mobility and bioavailability via the formation of metastable structures with large hydrophobic DOM molecules[5-7]. Alternatively, the binding of Hg to small molecules such as amino acids or peptides (e.g., cysteine or glutathione (GSH)) has been shown to increase Hg bioavailability[8]. DOM hydrogenation and oxygenation has been previously correlated to microbial uptake of DOM nutrient sources[9]. For example, DOM high in hydrogenated (larger H/C, lower O/C) nitrogen containing compounds correspond to more bioavailable amino acid rich material whereas highly oxygenated (larger O/C, lower H/C) carbon sources are less favorable microbial nutrient sources[9-19]. Sulfides (free or associated with DOM) are predicted to be an important ligand for $Hg^{II}$ under anoxic conditions that also favor MMHg formation, but strong interactions between $Hg^{II}$ and DOM in oxic waters can affect subsequent binding to sulfides[7]. This is important in stratified aquatic ecosystems where an oxic water column overlies an anoxic zone[11-14]. The binding of Hg to DOM is controlled by a group of homologous structures within DOM containing reduced sulfur species (R-SH), but understanding how composition and size of organic ligands influence Hg bioavailability has also been lacking[15-19].

SUMMARY

Accordingly, the present application includes a method of binding a metal ion in water, the method comprising:
contacting the water with a fraction of dissolved organic material (DOM) to form a complex between the DOM fraction and the metal ion; and
optionally separating the complex from the water.

The present application also includes a use of a fraction of dissolved organic material (DOM) for binding a metal ion in water.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The present application will now be described in greater detail with reference to the drawings, in which.

Asterisk represents a significant difference (p<0.05) in composition between LMW and HMW fractions for both SRFA and PLFA.

Figure 8:
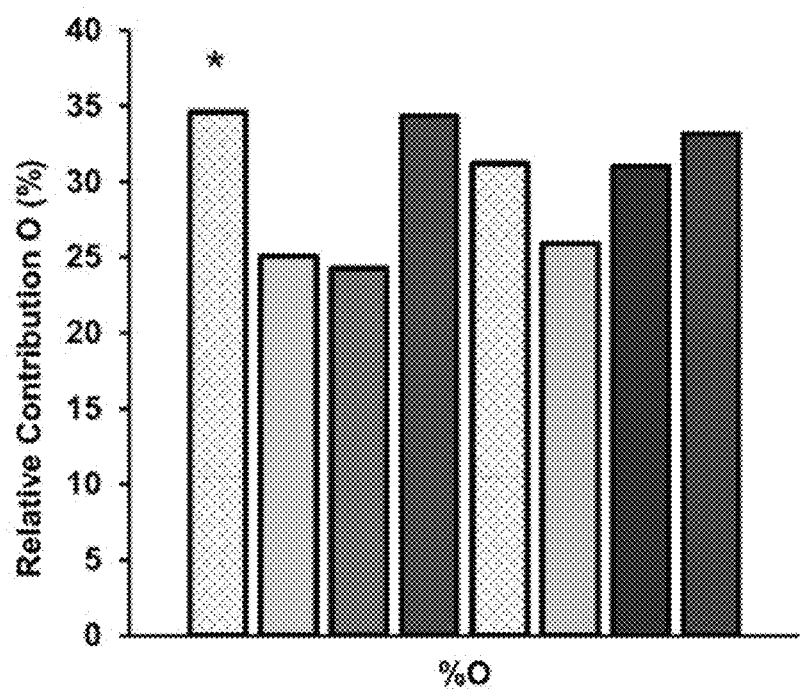

FIG. 8 shows FT ICR-MS weighted elemental contribution within bulk (dotted) and AF4 size fractions of SRFA (left four bars) and PLFA (right four bars) for oxygen. Asterisk represents a significant difference (p<0.05) in composition between LMW and HMW fractions for both SRFA and PLFA.

Figure 9:
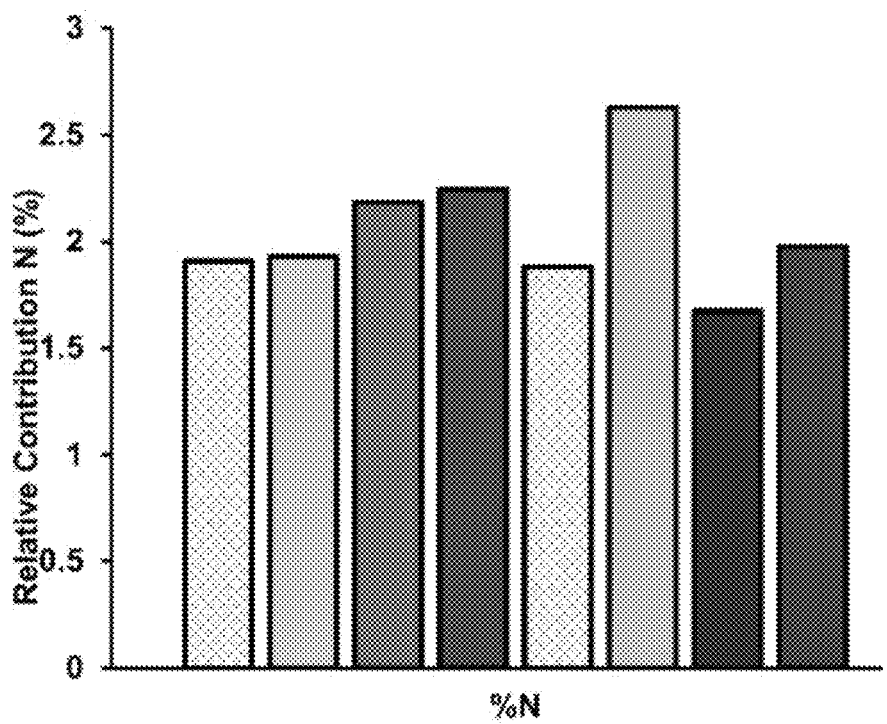

FIG. 9 shows FT ICR-MS weighted elemental contribution within bulk (dotted) and AF4 size fractions of SRFA (left four bars) and PLFA (right four bars) for nitrogen.

Figure 10:
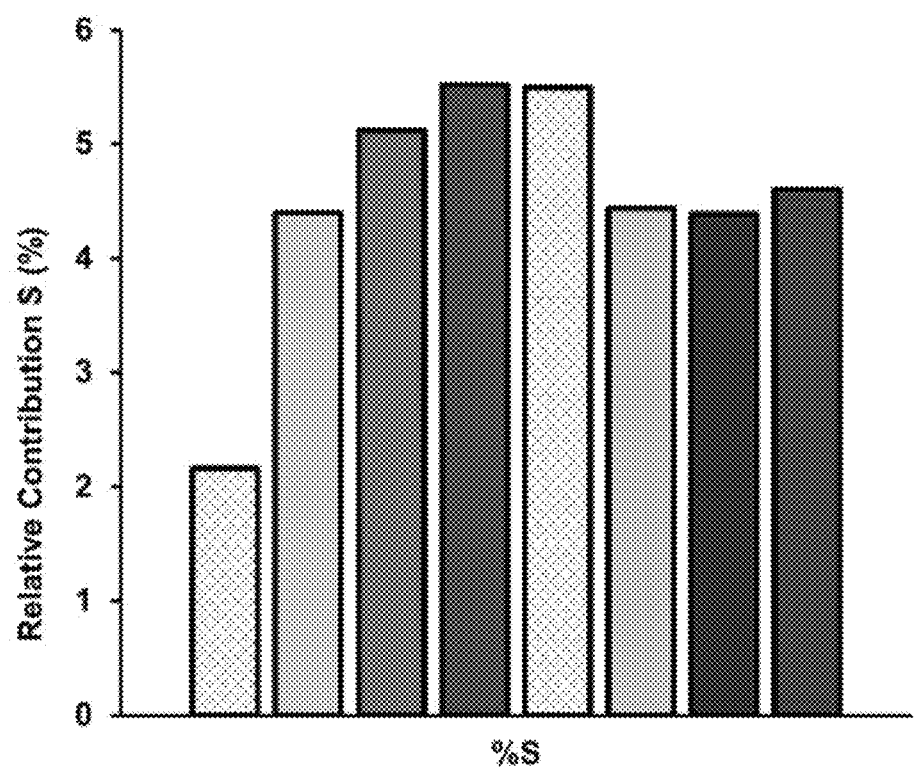

FIG. 10 shows FT ICR-MS weighted elemental contribution within bulk (dotted) and AF4 size fractions of SRFA (left four bars) and PLFA (right four bars) for sulfur.

Figure 11:
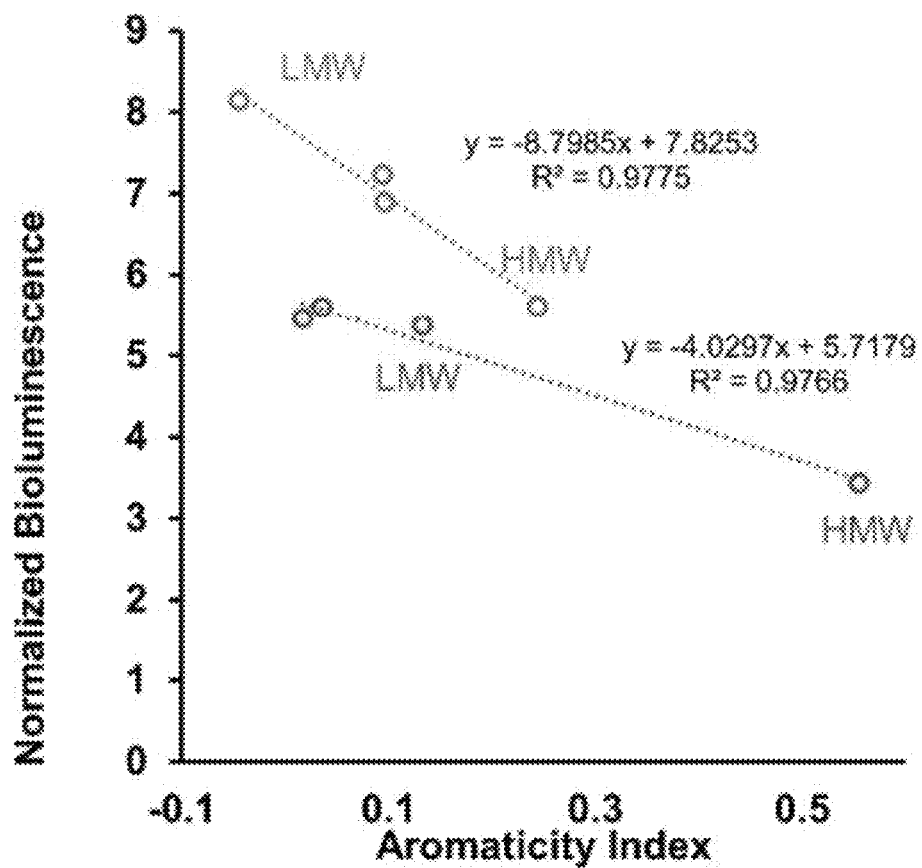

FIG. 11 is a plot showing the inverse relationships between normalized bioassays and corresponding aromaticity index (AI) of each size fraction and unfractionated sample in FIGS. 6-10.

Figure 12:
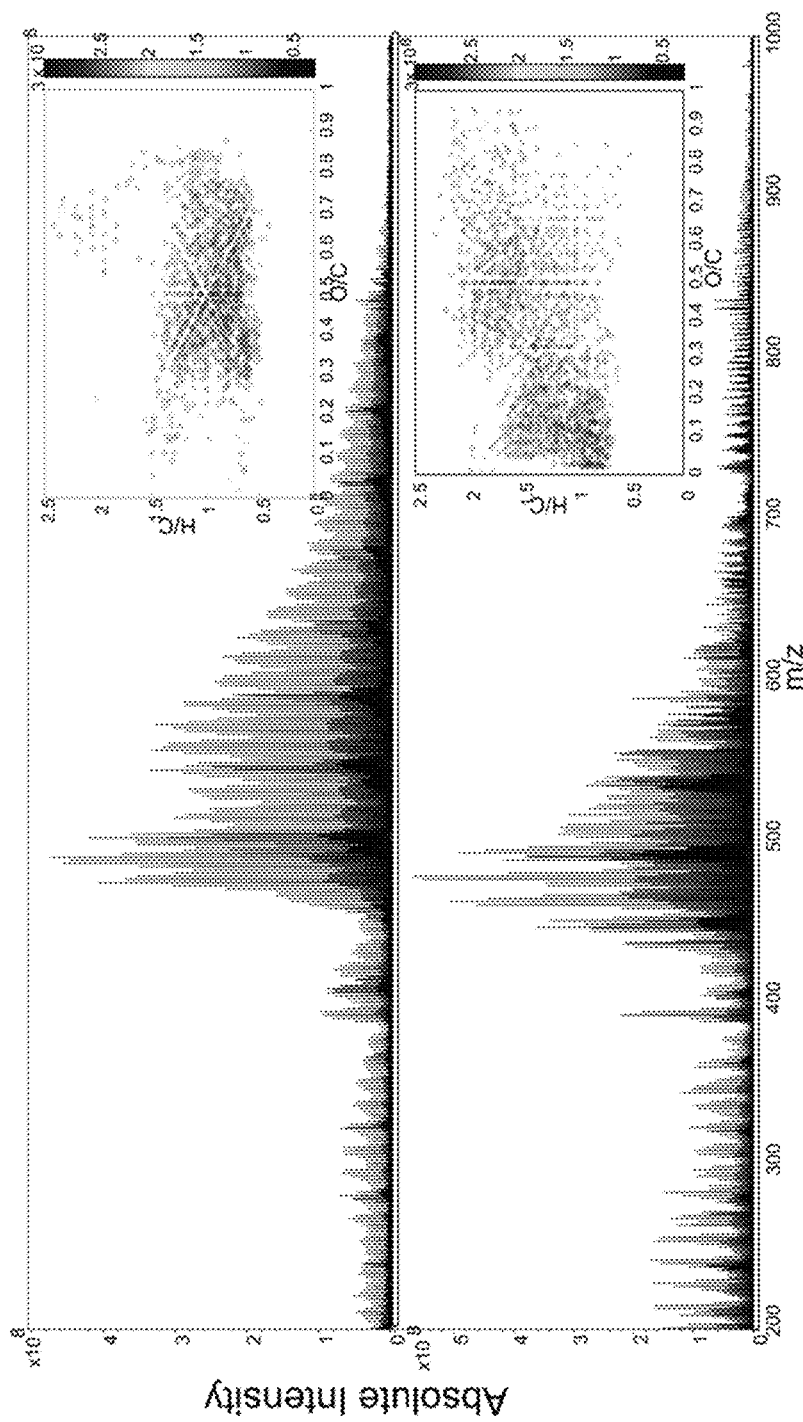

FIG. 12 shows FT ICR-MS spectra of SRFA (top) and PLFA (bottom) based on an average of 200 scans and corresponding 3D van Krevelen diagrams (insert graphs). In colored figures, the van Krevelen diagram shade is based on the absolute intensity of the corresponding peak (light to dark increasing in intensity).

Figure 13:
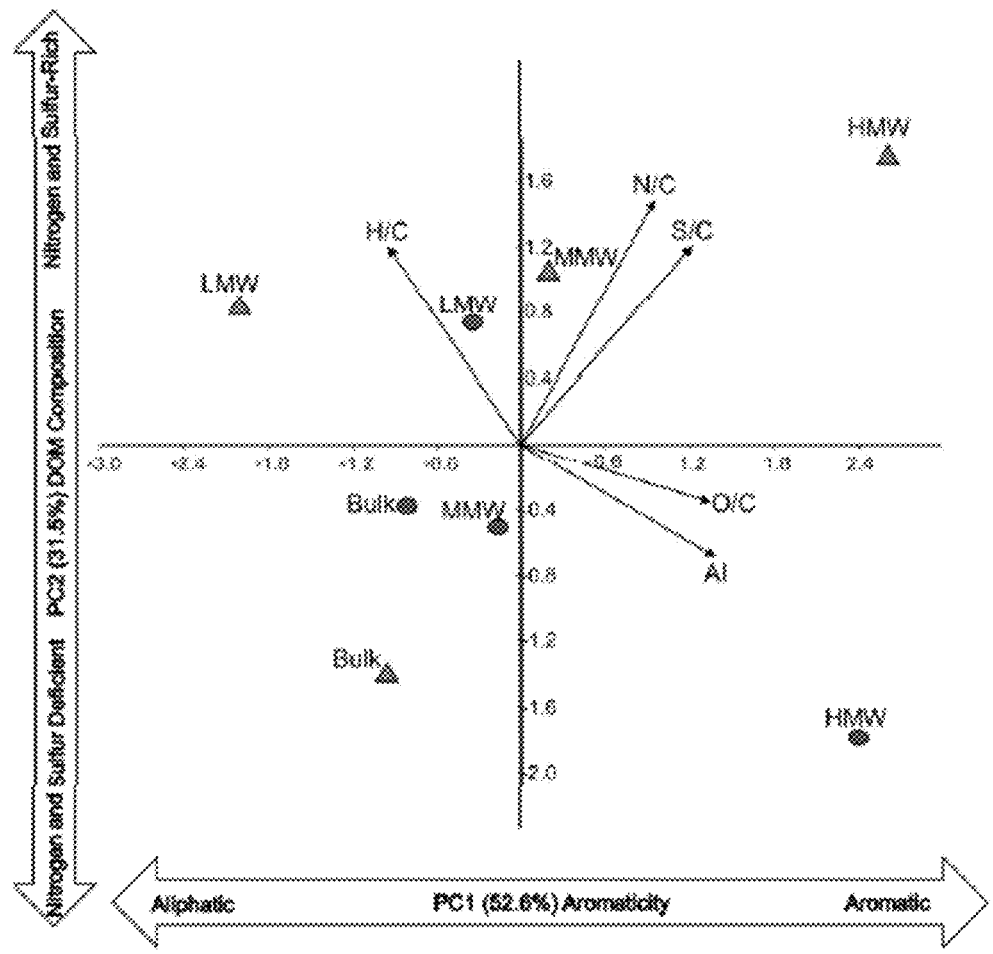

FIG. 13 shows principal component analysis (PCA) of atomic ratios and size fractions by SRFA (triangles) and PLFA (circles).

Figure 14:
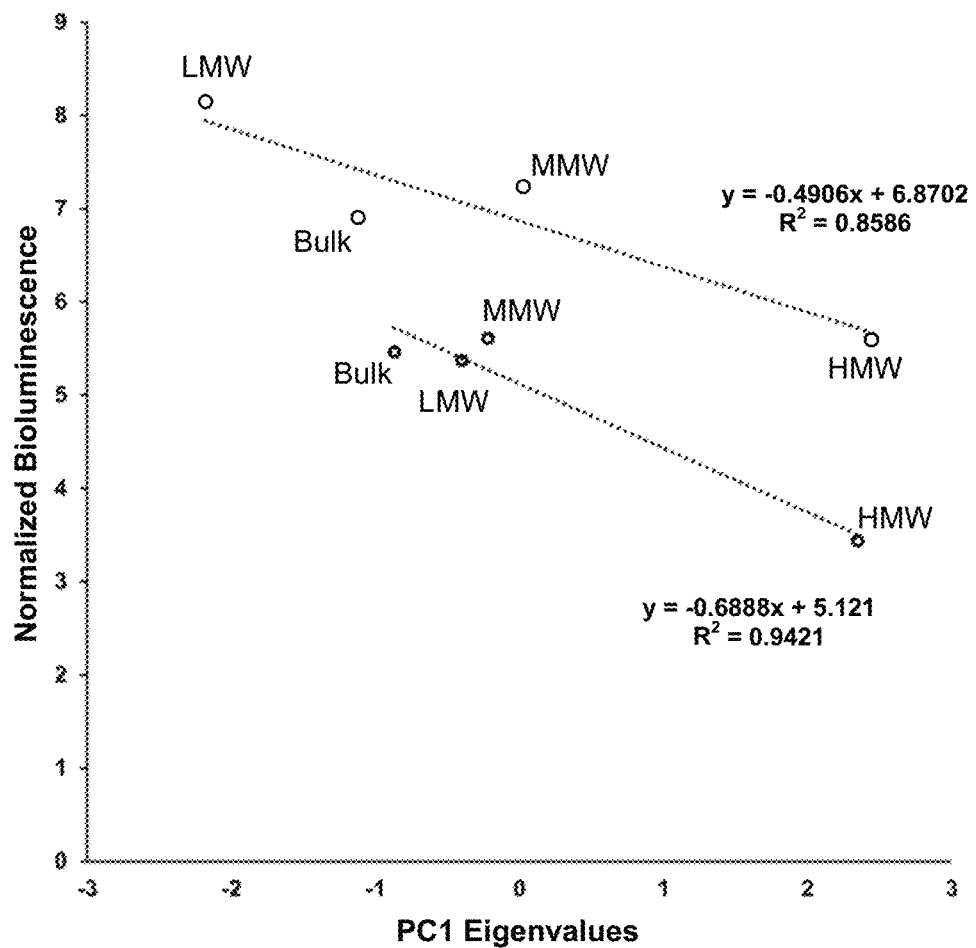

FIG. 14 shows principal component 1 (PC1) eigenvalues vs. normalized bioluminescence response for SRFA (top) and PLFA (bottom).

Figure 15:
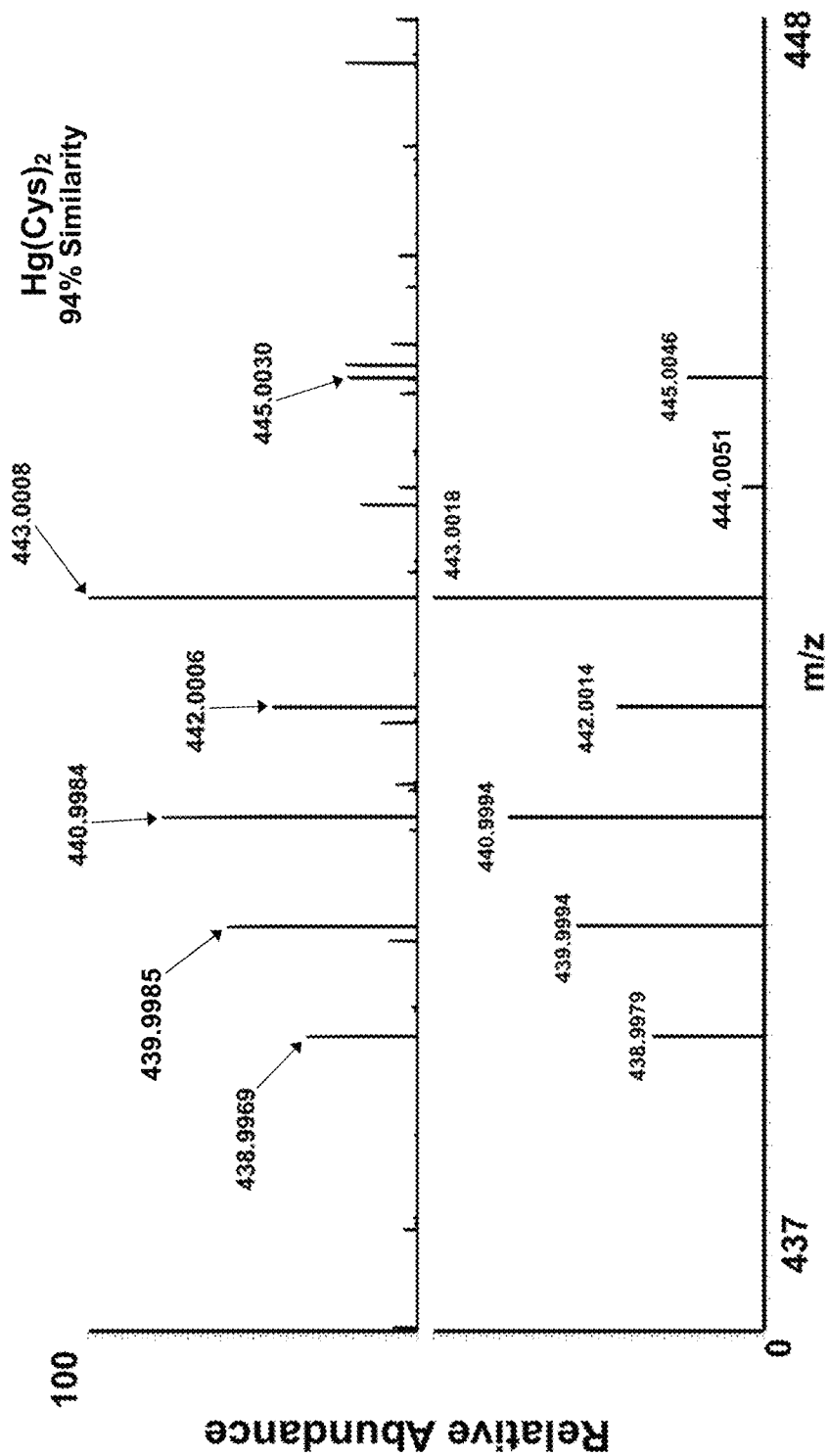

FIG. 15 shows the relative abundance of various ions for $Hg(Cys)_2$ complexes detected (top) in comparison to the theoretical isotopic distribution (bottom) according to an example of the present application.

Figure 16:
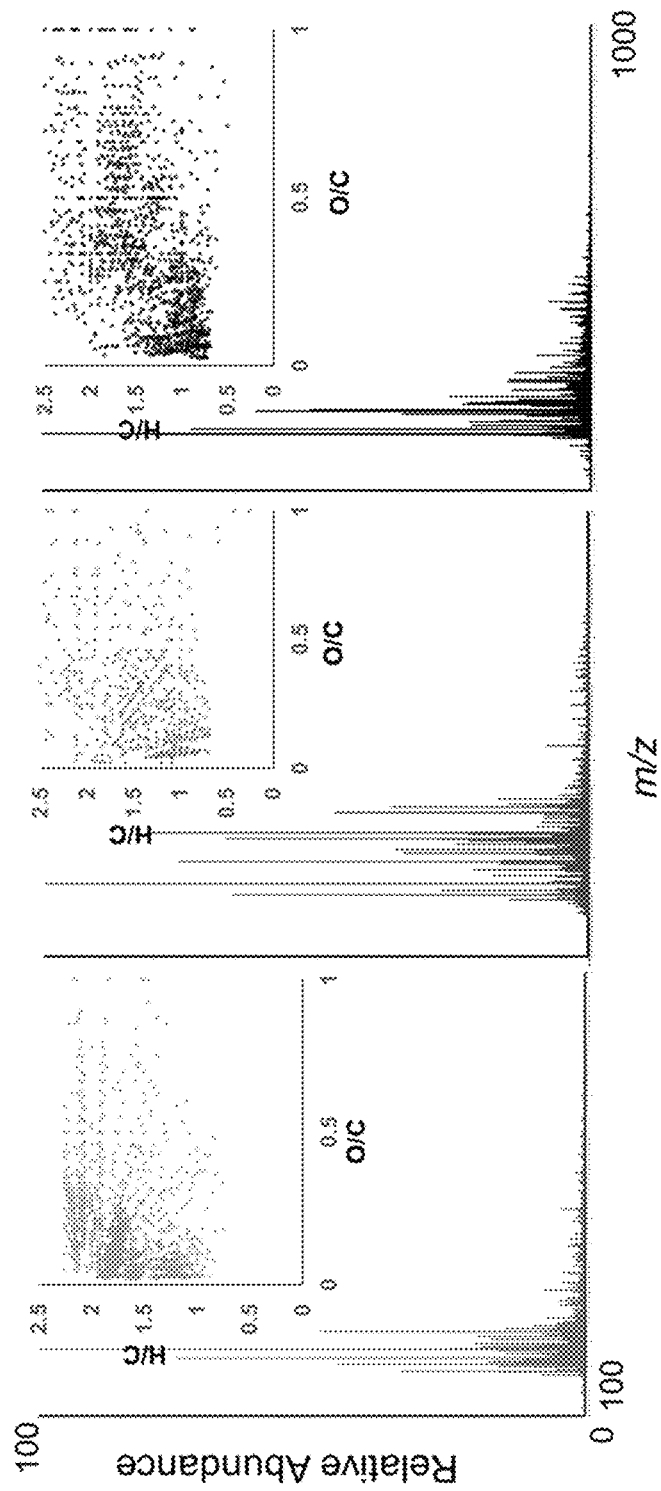

FIG. 16 shows mass spectra and van Krevelen plots (insets) for phytoplankton derived DOM from *Chlorella* (left), *Chlamydomonas* (middle) and *Euglena* (right) according to examples of the present application.

Figure 17:
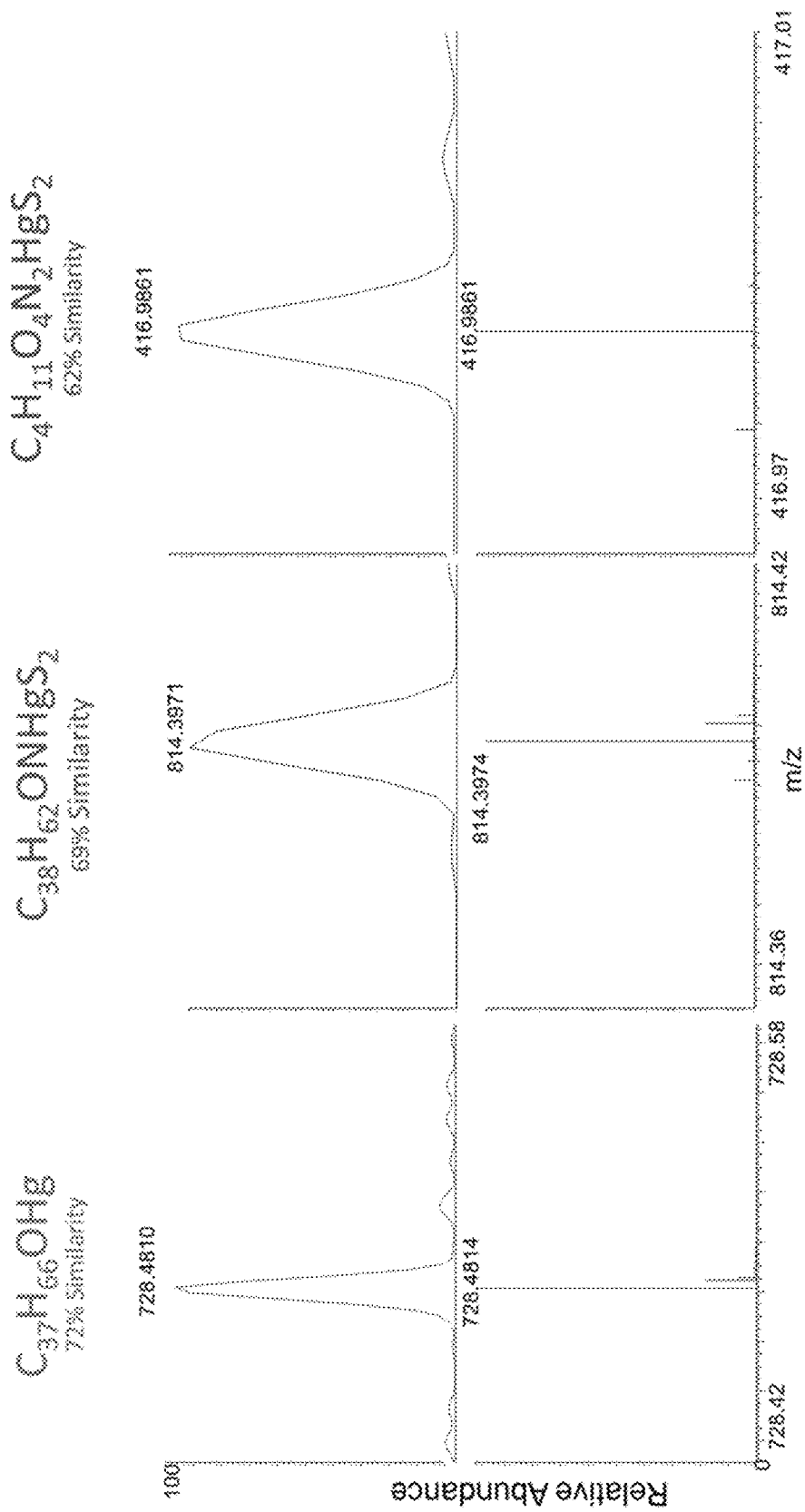

FIG. 17 shows a comparison between the observed (top) and predicted (bottom) isotopic distributions for the $^{202}Hg$ peak found in phytoplankton-derived DOM Hg complexes from *Chlorella* (left), *Chlamydomonas* (middle) and *Euglena* (right) according to an example of the present application.

Figure 18:
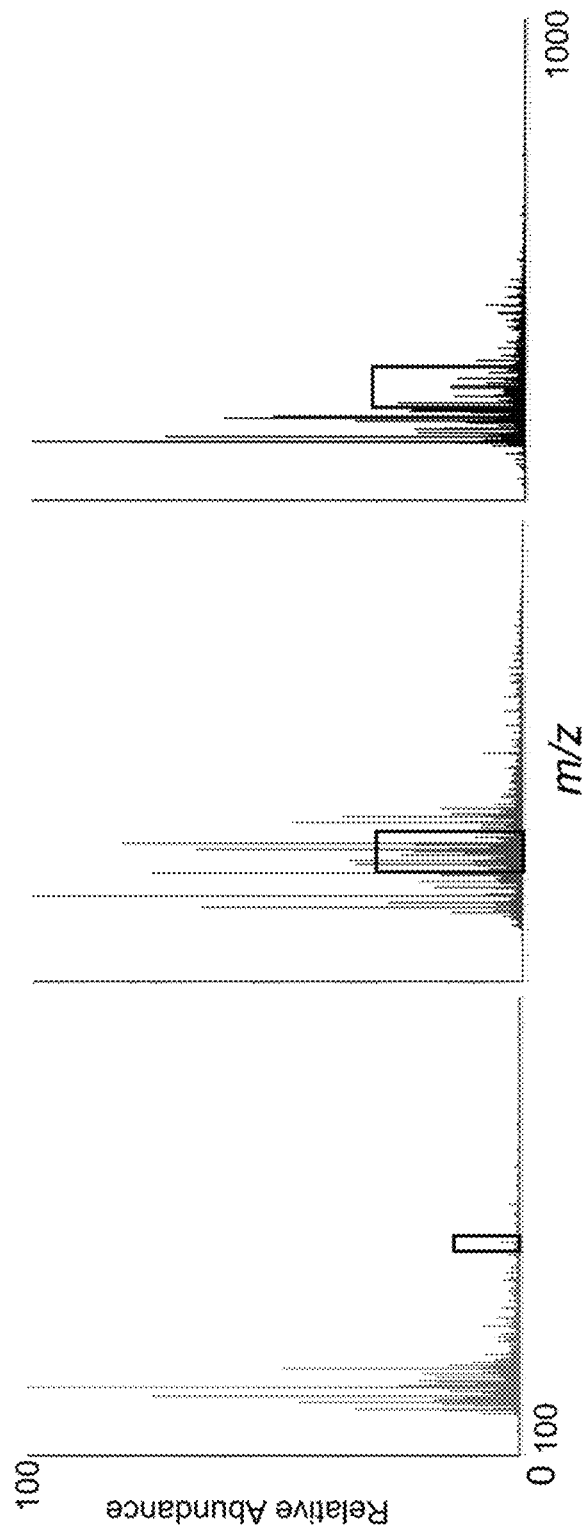

FIG. 18 shows mass spectra for phytoplankton-derived DOM Hg complexes from *Chlorella* (left), *Chlamydomonas* (middle) and *Euglena* (right) according to an example of the present application. Boxes indicate the location along the m/z axis left to right, the formulae: $C_{37}H_{66}OHg$, $C_8H_{15}N_2Hg$ and $C_{10}H_{11}O_2HgS$.

Figure 19:
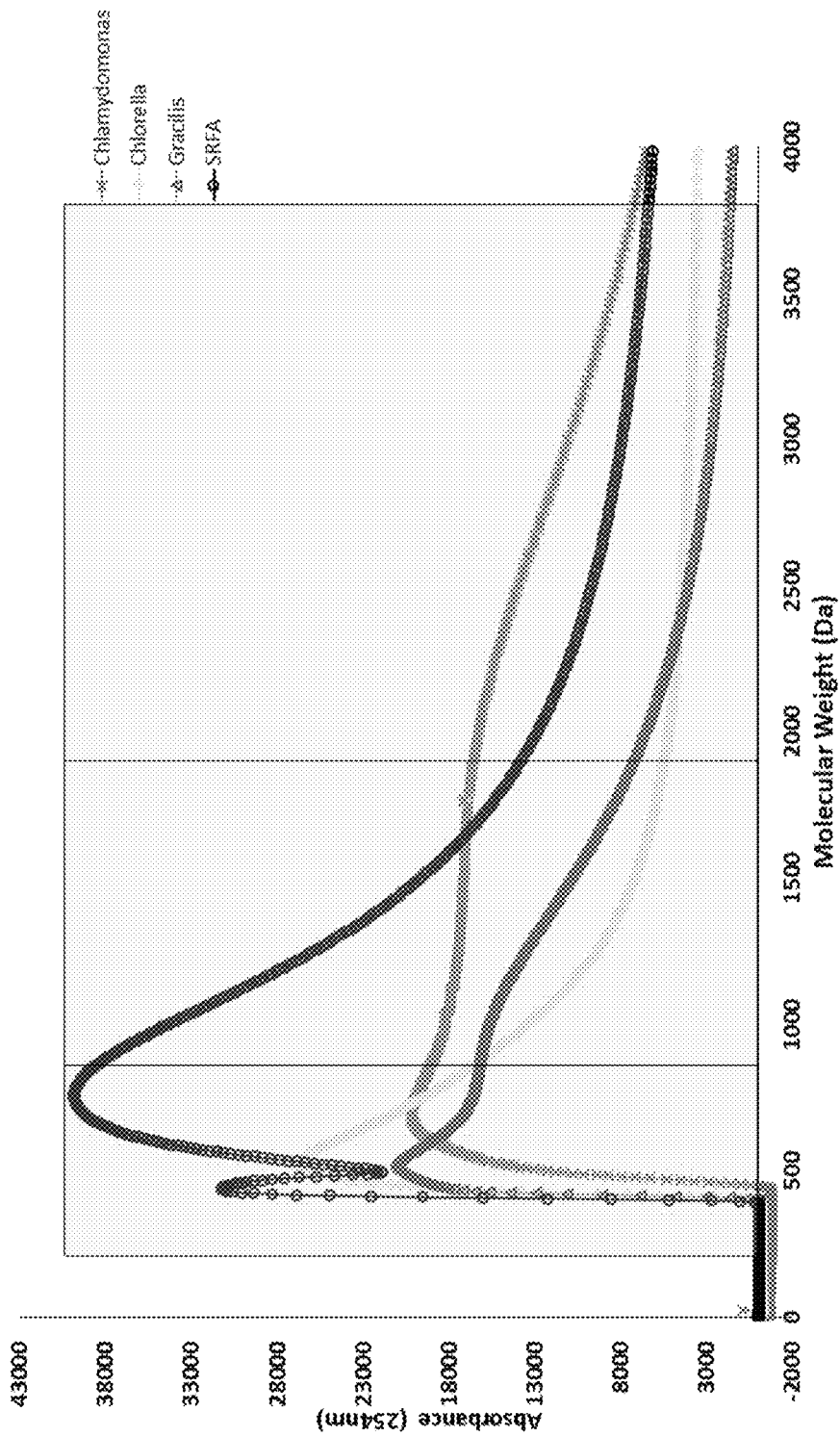

FIG. 19 is a plot of AF4 used to separate DOM from SRFA, *Chlorella vulgaris*, *Chlamydomonas reinhardtii*, and *Euglena gracilis* according to examples of the present application with vertical bars indicating the boundaries between low molecular weight (LMW; 300-900 Da); medium molecular weight (MMW; 900-1800 Da) and high molecular weight (HMW; 1800-3500 Da) fractions.

Figure 20:
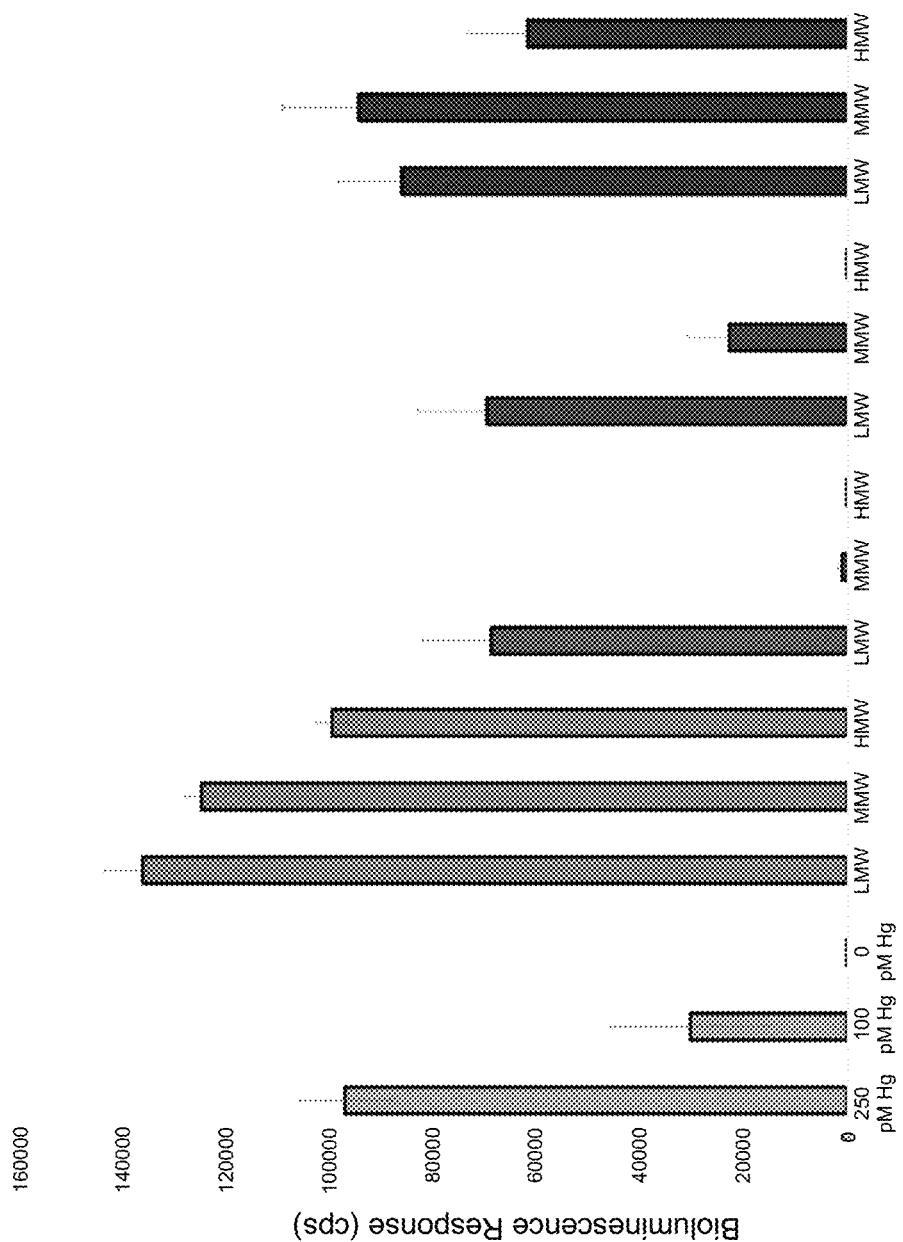

FIG. 20 is a plot of bioluminescence response as a function of the fractions in FIG. 19 exposed to 250 pM of $Hg(NO_3)_2$ according to examples of the present application (4-6 bars from left: SRFA; 7-9 bars from left: *Chlorella*; 10-12 bars from left: *Chlamydomonas*; 13-15 bars from left: *Euglena*). The first through third bars from the left indicate 250 pM, 100 pM and 0 pM, respectively of $HgNO_3$ added in the absence of ligands.

Figure 21:
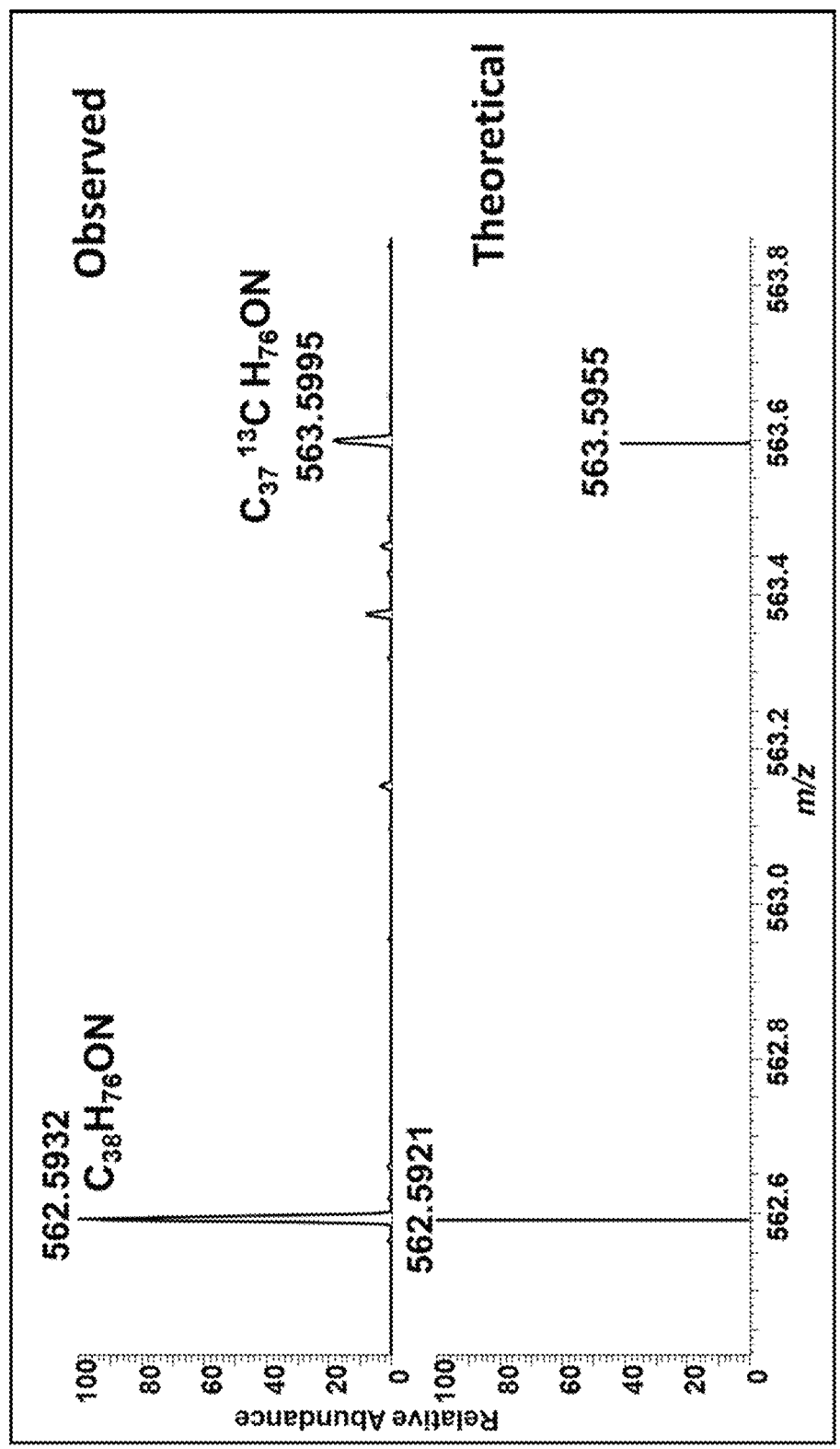

FIG. 21 shows a comparison between observed (top) vs theoretical (bottom) isotopic distribution confirming $^{13}C$ isotope of the molecule $C_{38}H_{76}ON$ to reinforce accurate formula assignment.

Figure 22:
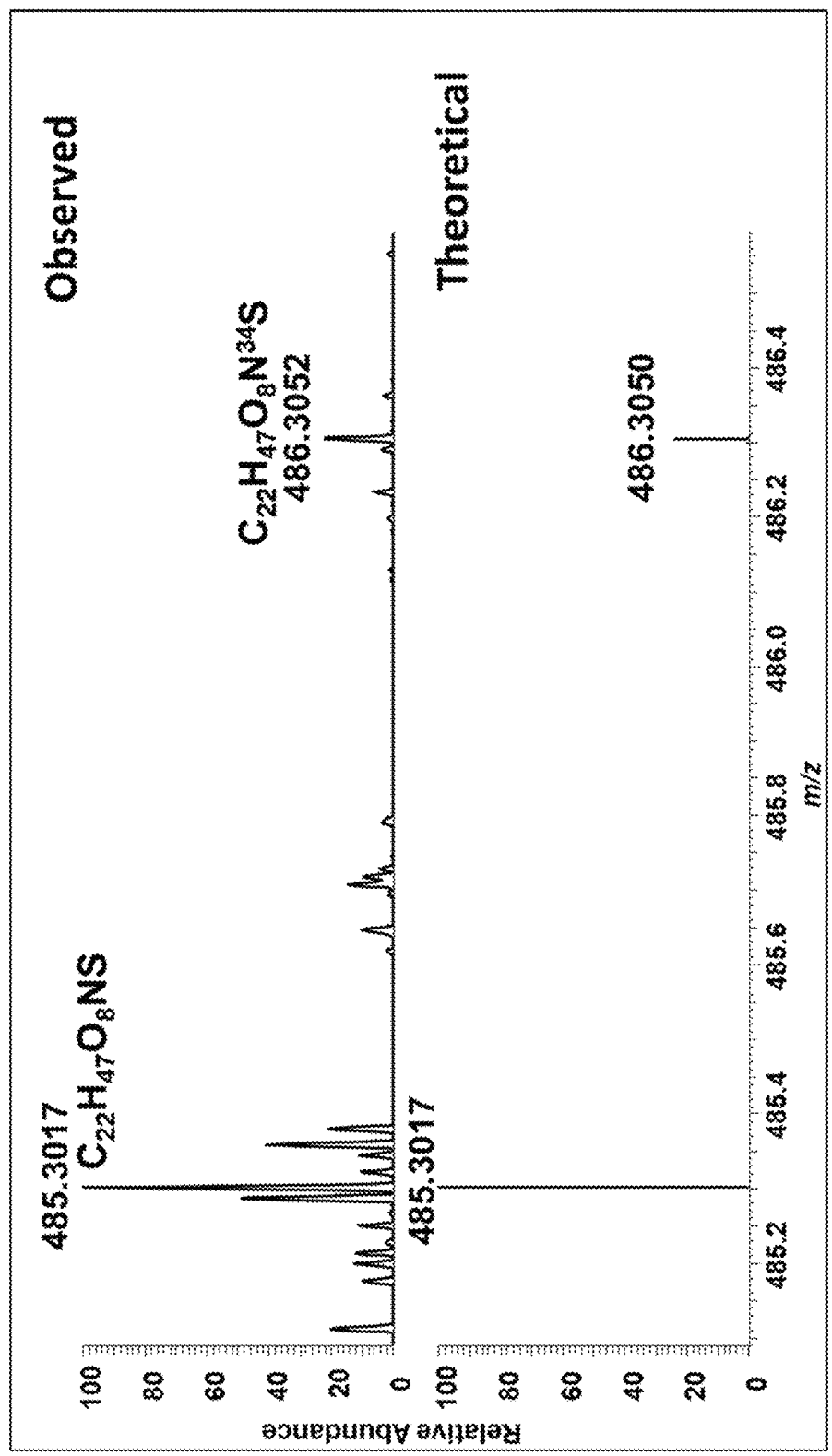

FIG. 22 shows a comparison between observed (top) vs theoretical (bottom) isotopic distribution confirming $^{34}S$ isotope of the molecule $C_{22}H_{47}O_8NS$ to reinforce accurate formula assignment.

Figure 23:
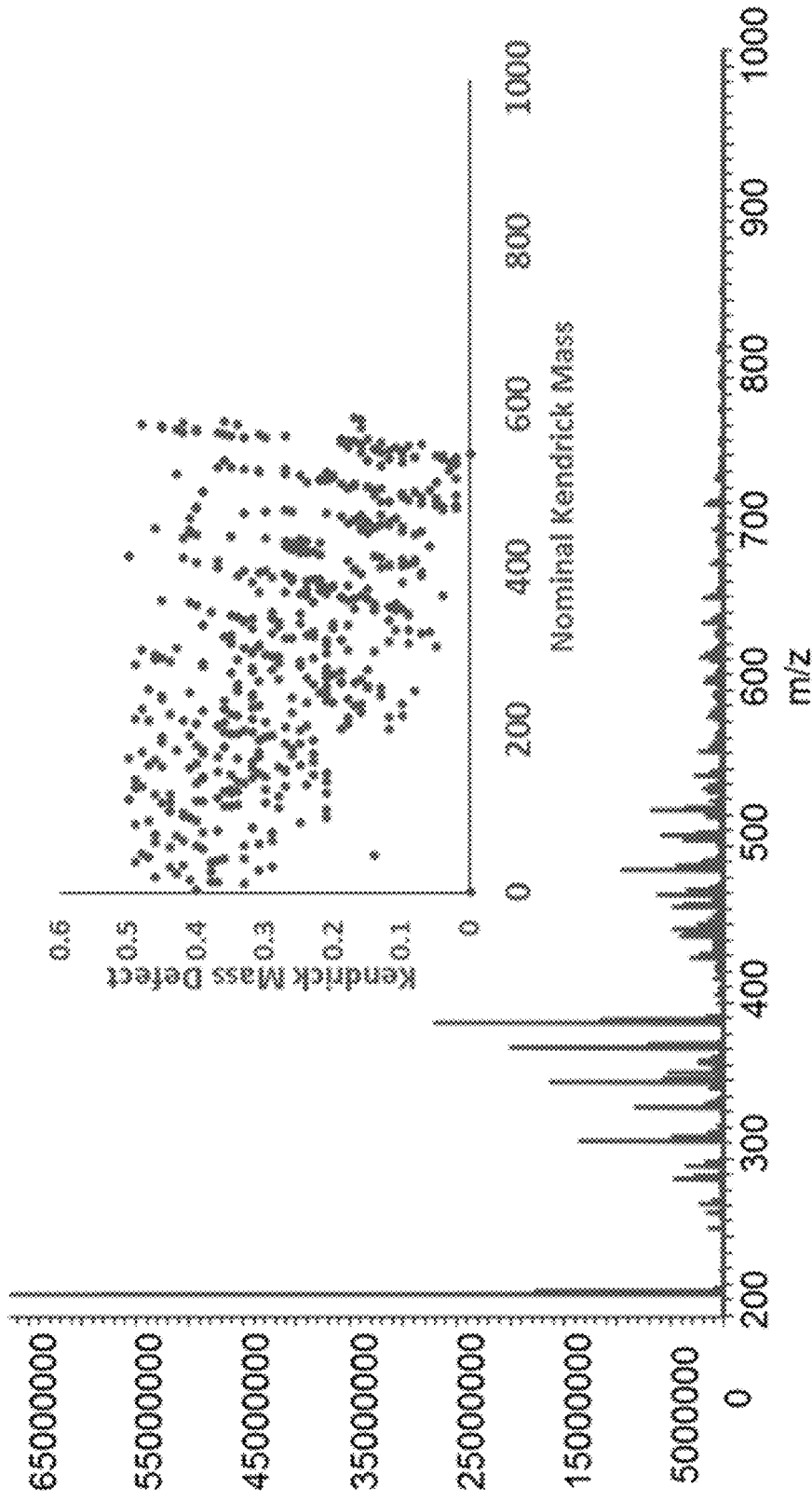

FIG. 23 shows a mass spectrum of the DOM composition and a Kendrick mass defect plot to display homologous $CH_2$ shifts indicative of DOM (inset) for *Chlorella* exposed to a standard (16:8 h) light regime in the absence of Hg according to an example of the present application.

Figure 24:
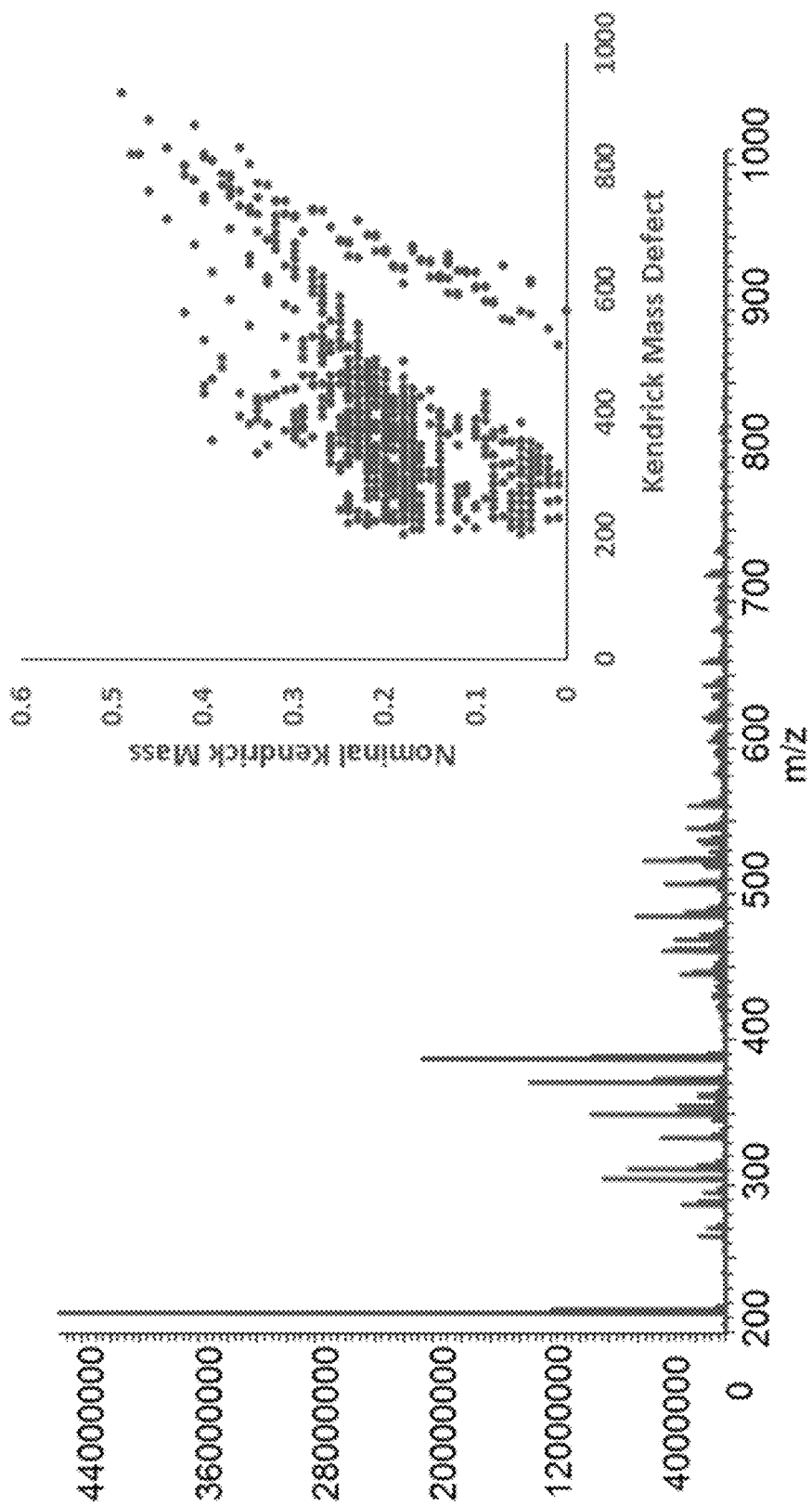

FIG. 24 shows a mass spectrum of the DOM composition and a Kendrick mass defect plot to display homologous $CH_2$ shifts indicative of DOM (inset) for *Chlorella* exposed to a standard (16:8 h) light regime in the presence of Hg according to an example of the present application.

Figure 25:
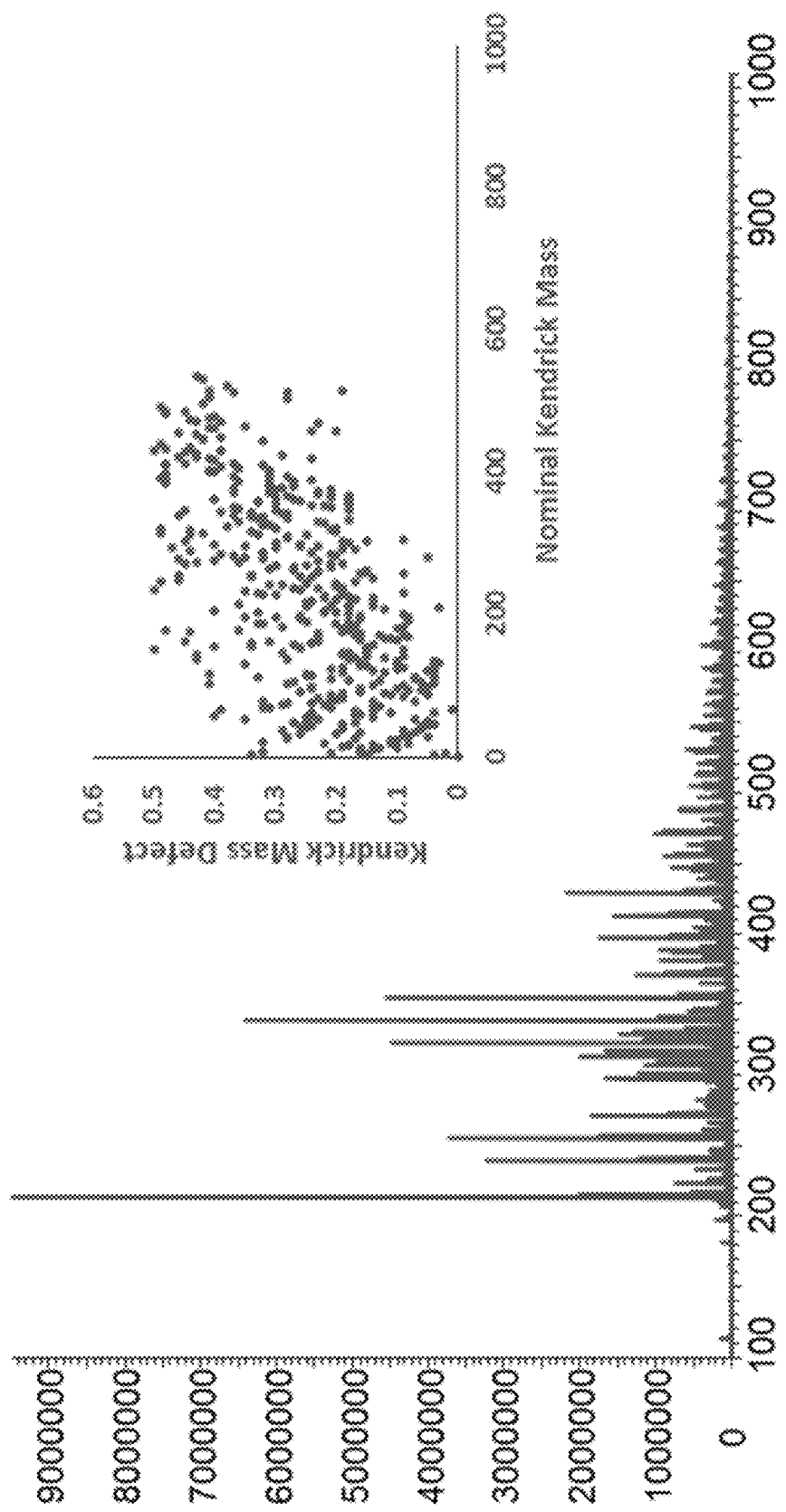

FIG. 25 shows a mass spectrum of the DOM composition and a Kendrick mass defect plot to display homologous $CH_2$ shifts indicative of DOM (inset) for *Chlorella* exposed to a high (20:4 h) light regime in the absence of Hg according to an example of the present application.

Figure 26:
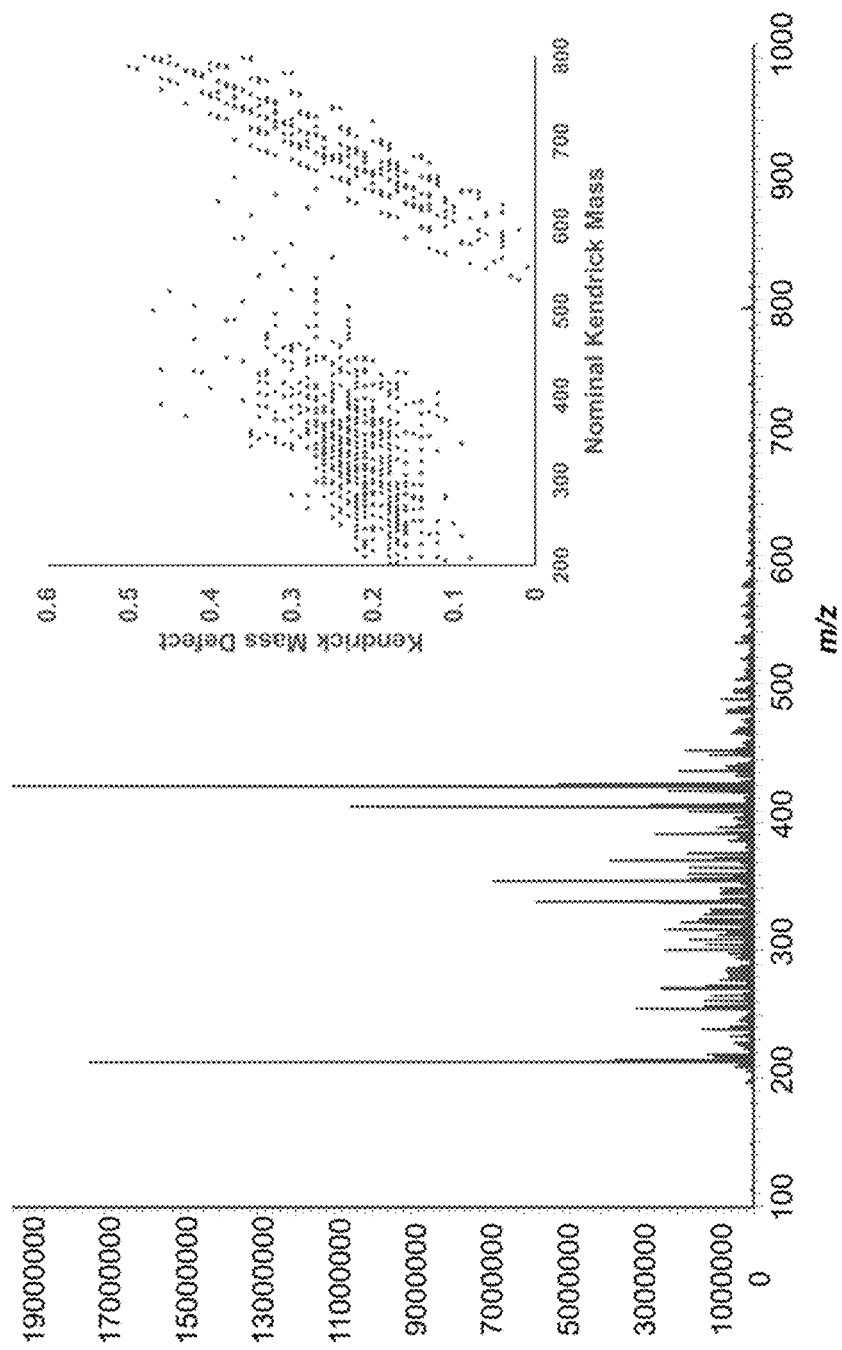

FIG. 26 shows a mass spectrum of the DOM composition and a Kendrick mass defect plot to display homologous $CH_2$ shifts indicative of DOM (inset) for *Chlorella* exposed to a high (20:4 h) light regime in the presence of Hg according to an example of the present application.

Figure 27:
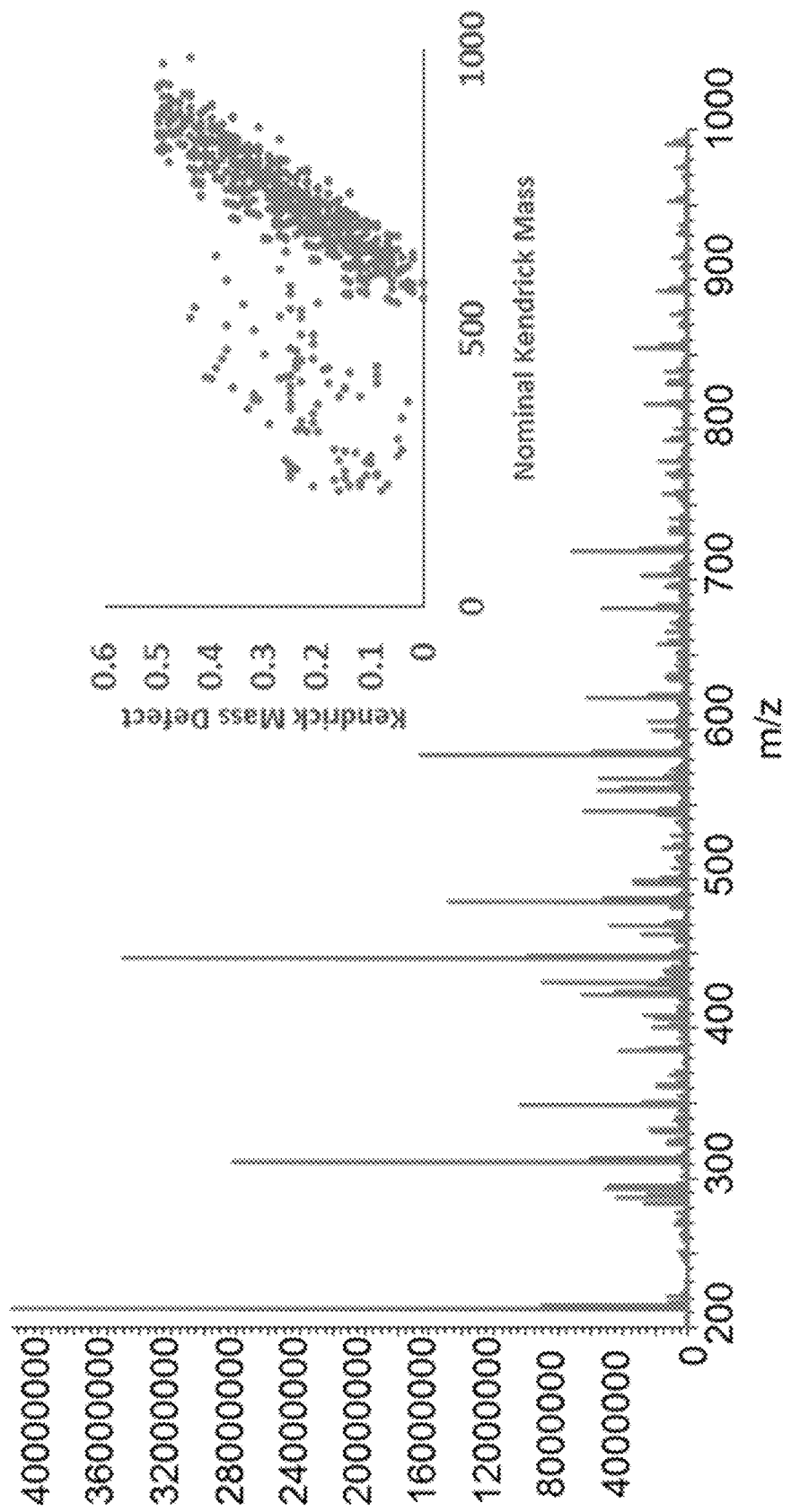

FIG. 27 shows a mass spectrum of the DOM composition and a Kendrick mass defect plot to display homologous $CH_2$ shifts indicative of DOM (inset) for *Chlamydomonas* exposed to a standard (16:8 h) light regime in the absence of Hg according to an example of the present application.

Figure 28:
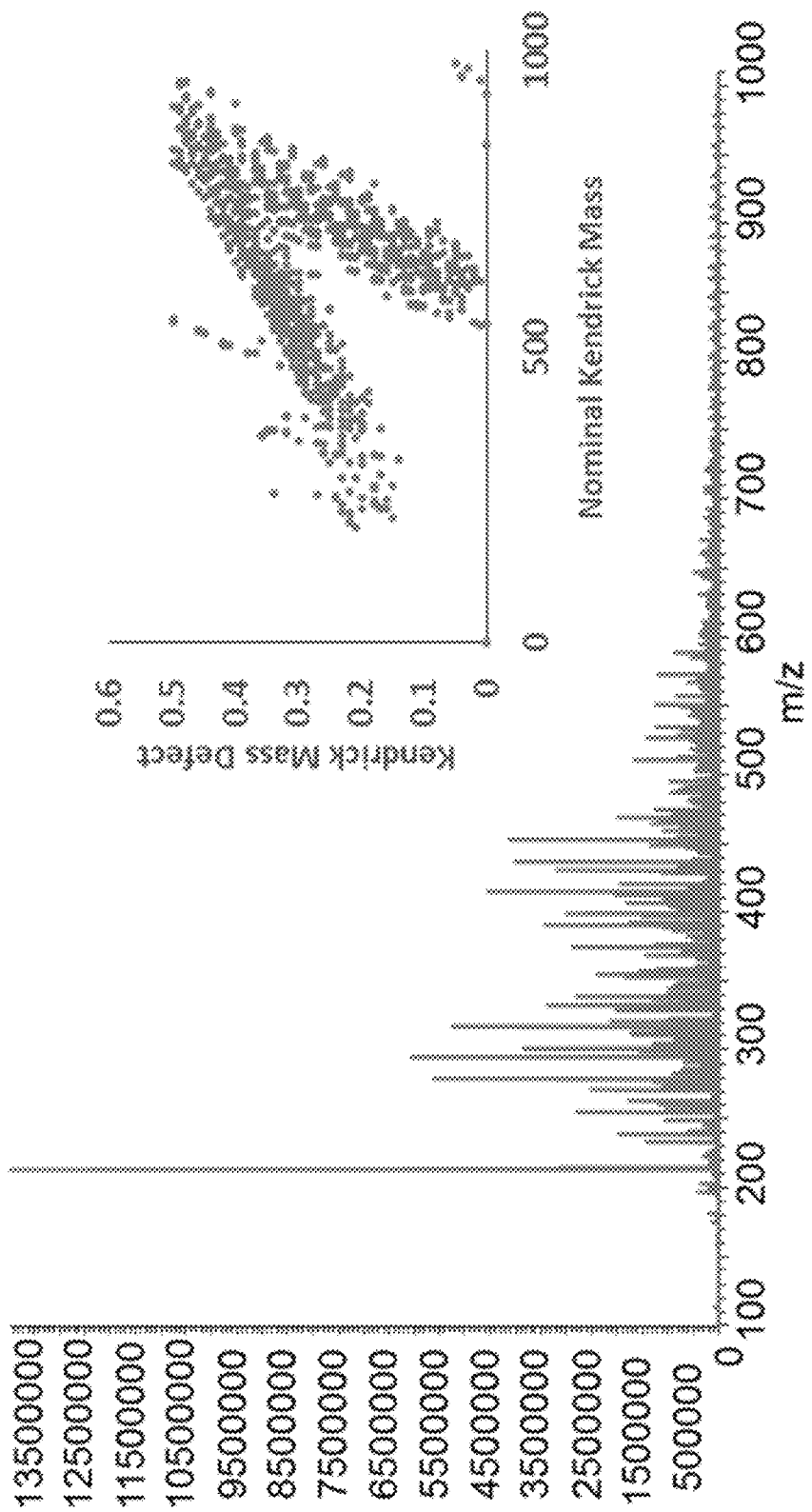

FIG. 28 shows a mass spectrum of the DOM composition and a Kendrick mass defect plot to display homologous $CH_2$ shifts indicative of DOM (inset) for *Chlamydomonas* exposed to a standard (16:8 h) light regime in the presence of Hg according to an example of the present application.

Figure 29:
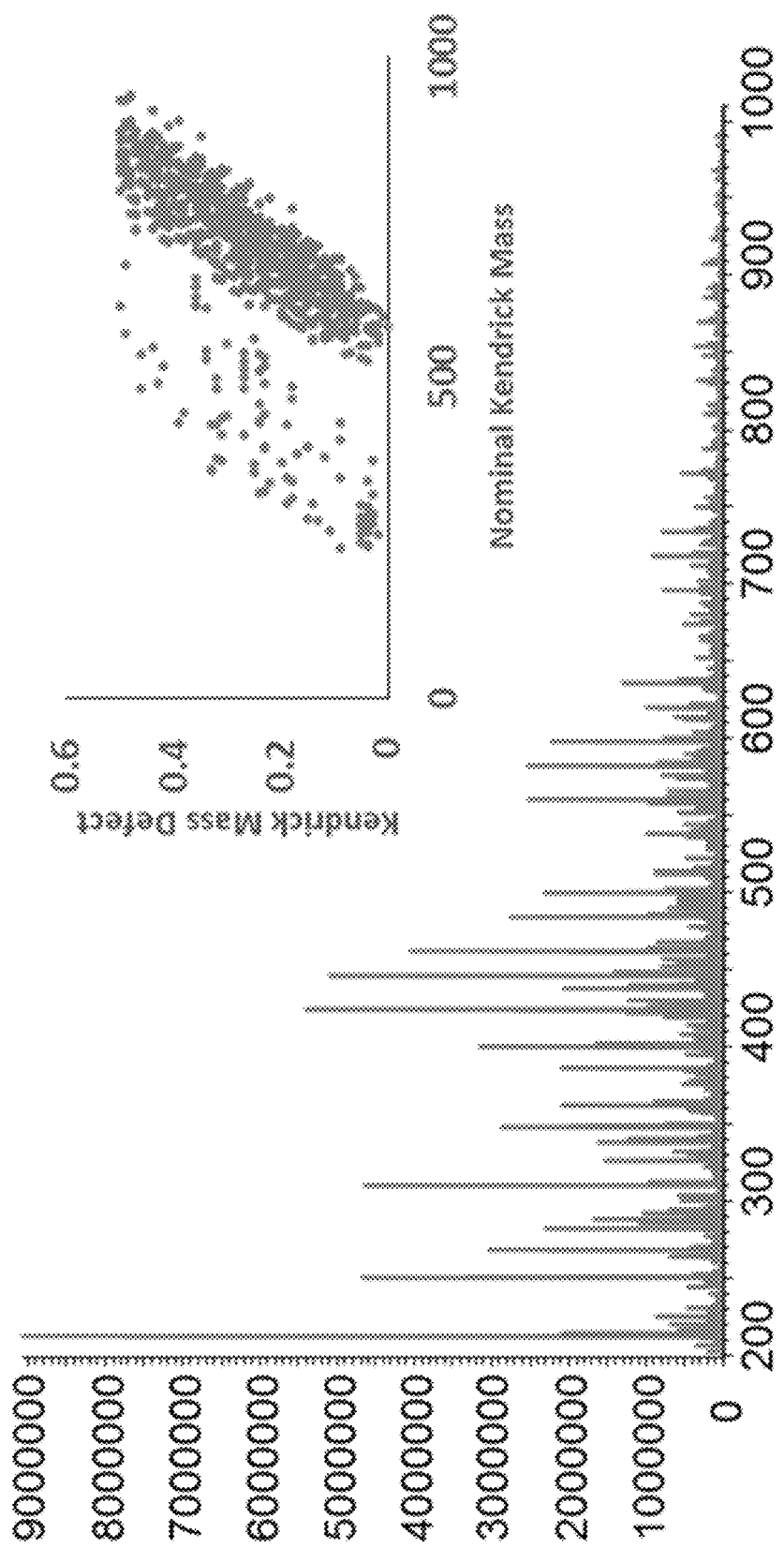

FIG. 29 shows a mass spectrum of the DOM composition and a Kendrick mass defect plot to display homologous $CH_2$ shifts indicative of DOM (inset) for *Chlamydomonas* exposed to a high (20:4 h) light regime in the absence of Hg according to an example of the present application.

Figure 30:
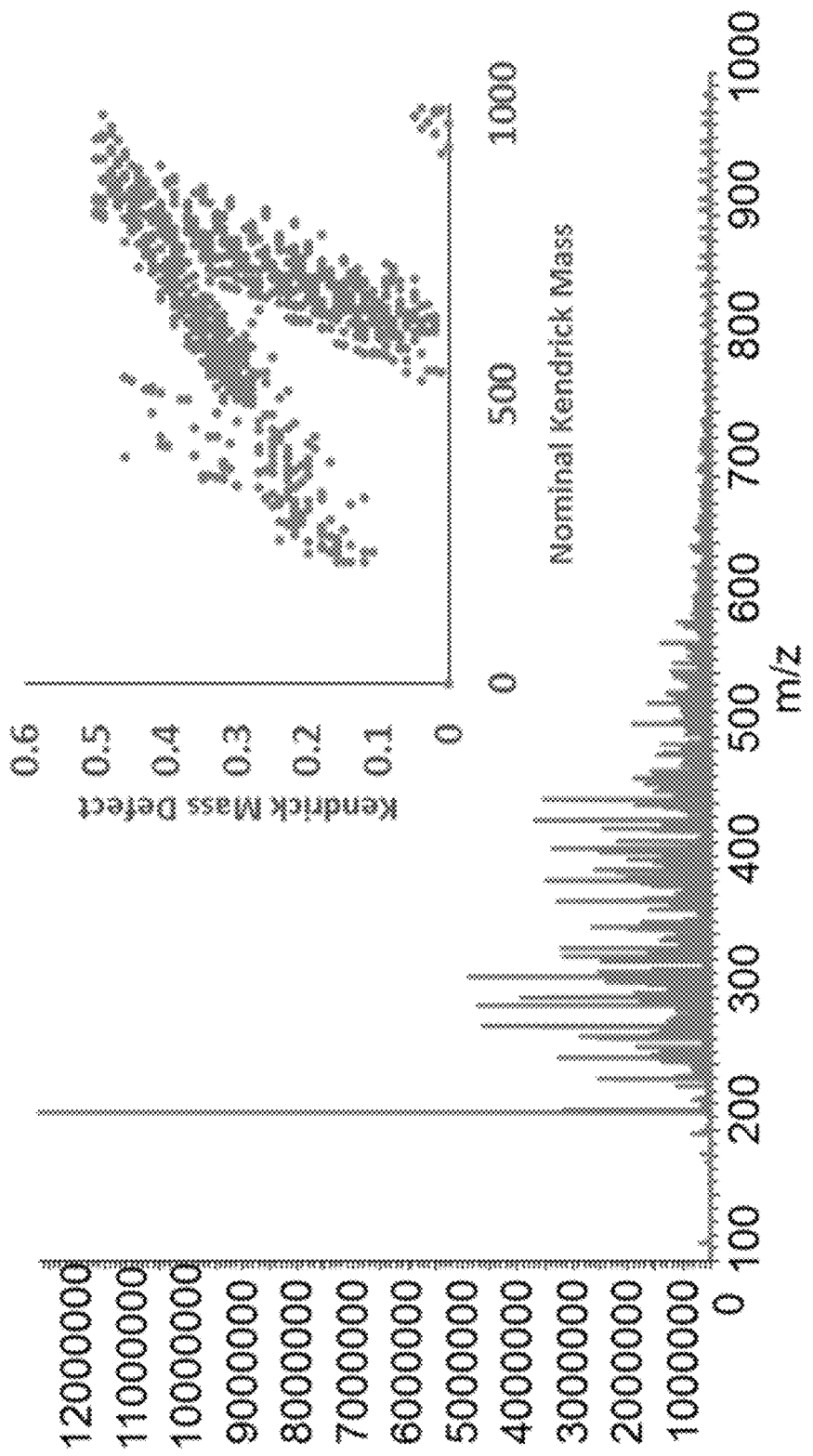

FIG. 30 shows a mass spectrum of the DOM composition and a Kendrick mass defect plot to display homologous $CH_2$ shifts indicative of DOM (inset) for *Chlamydomonas* exposed to a high (20:4 h) light regime in the presence of Hg according to an example of the present application.

Figure 31:
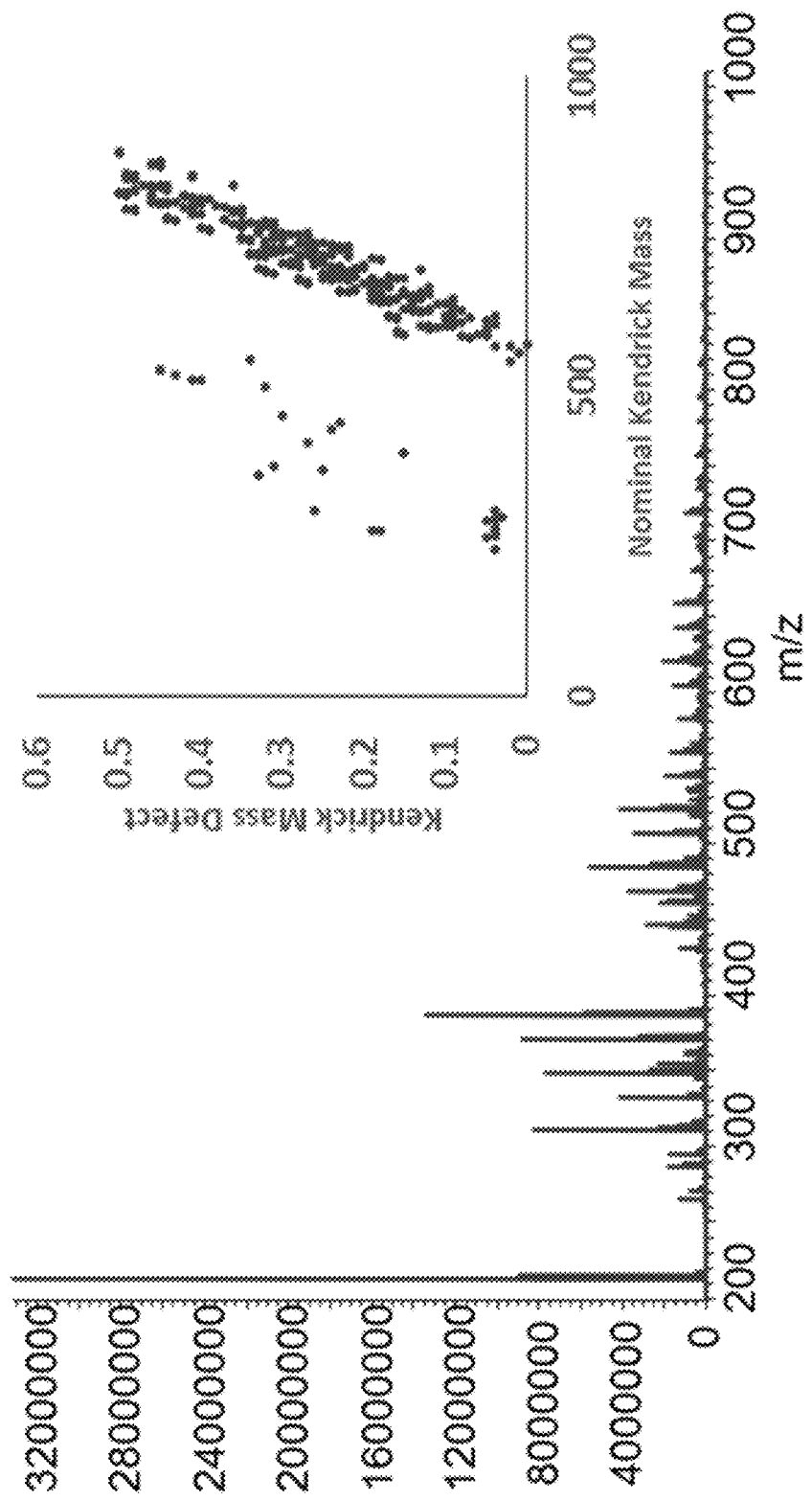

FIG. 31 shows a mass spectrum of the DOM composition and a Kendrick mass defect plot to display homologous $CH_2$ shifts indicative of DOM (inset) for *Scenedesmus* exposed to a standard (16:8 h) light regime in the absence of Hg according to an example of the present application.

Figure 32:
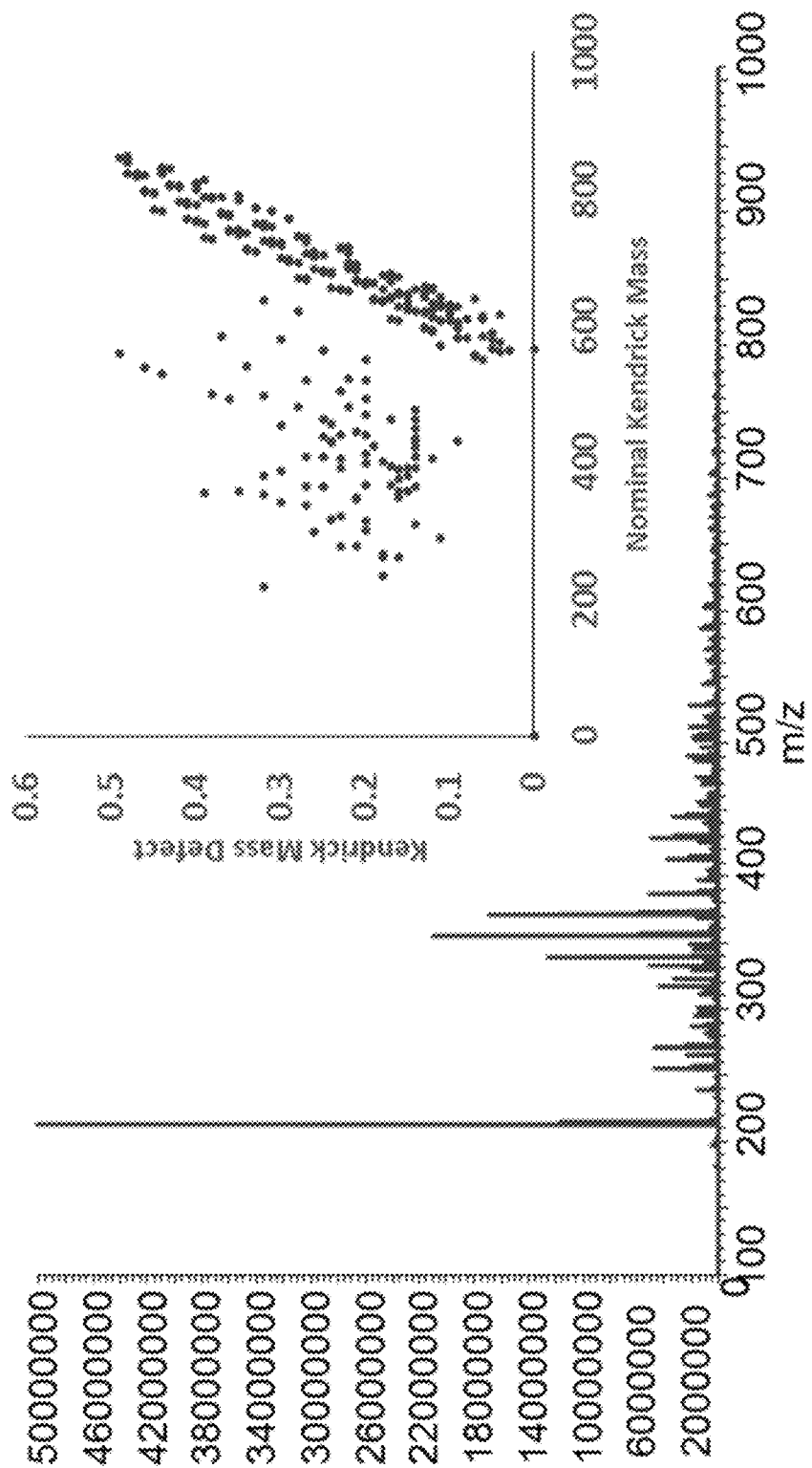

FIG. 32 shows a mass spectrum of the DOM composition and a Kendrick mass defect plot to display homologous $CH_2$ shifts indicative of DOM (inset) for *Scenedesmus* exposed to a standard (16:8 h) light regime in the presence of Hg according to an example of the present application.

Figure 33:
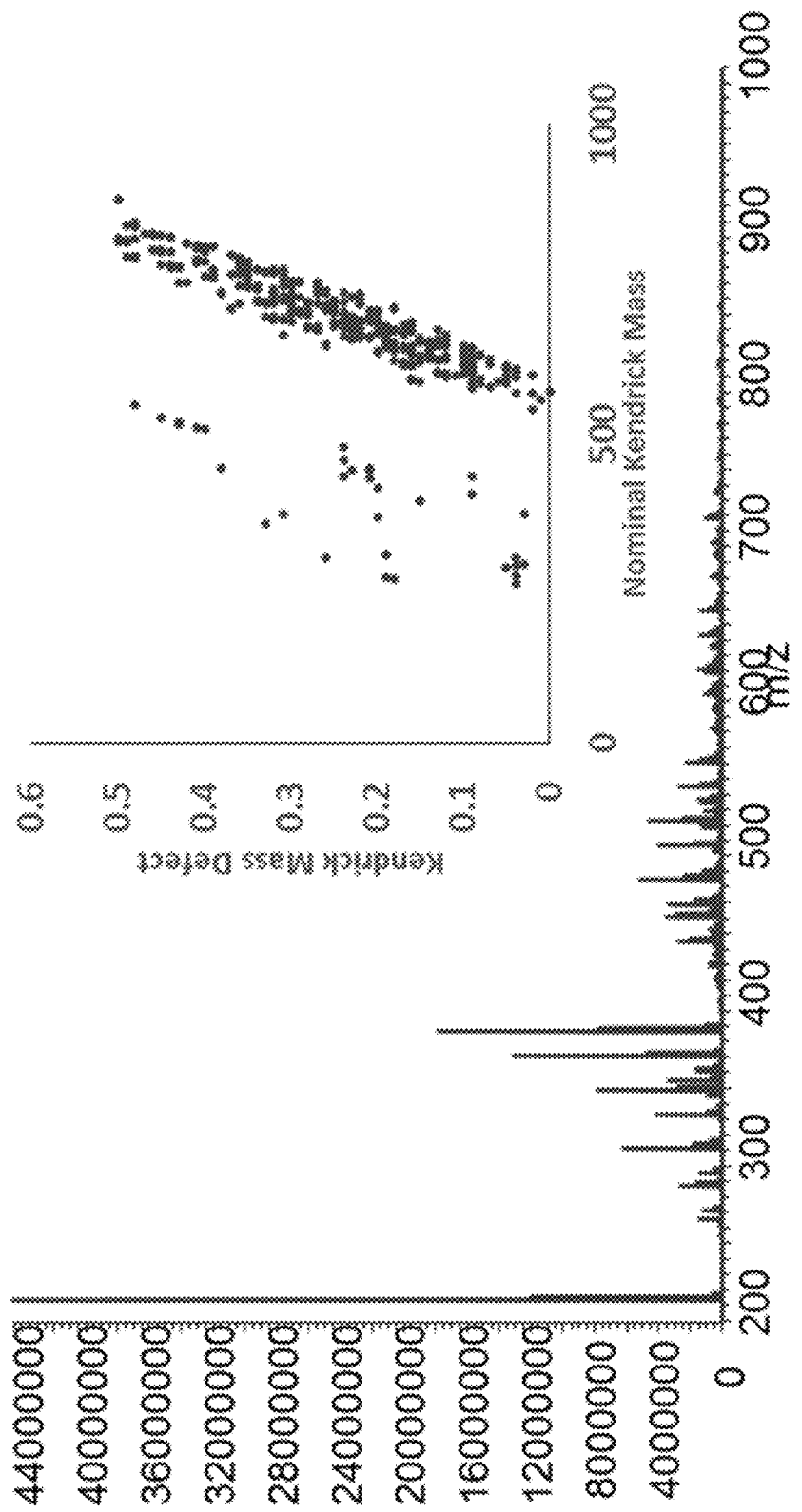

FIG. 33 shows a mass spectrum of the DOM composition and a Kendrick mass defect plot to display homologous $CH_2$ shifts indicative of DOM (inset) for *Scenedesmus* exposed to a high (20:4 h) light regime in the absence of Hg according to an example of the present application.

Figure 34:
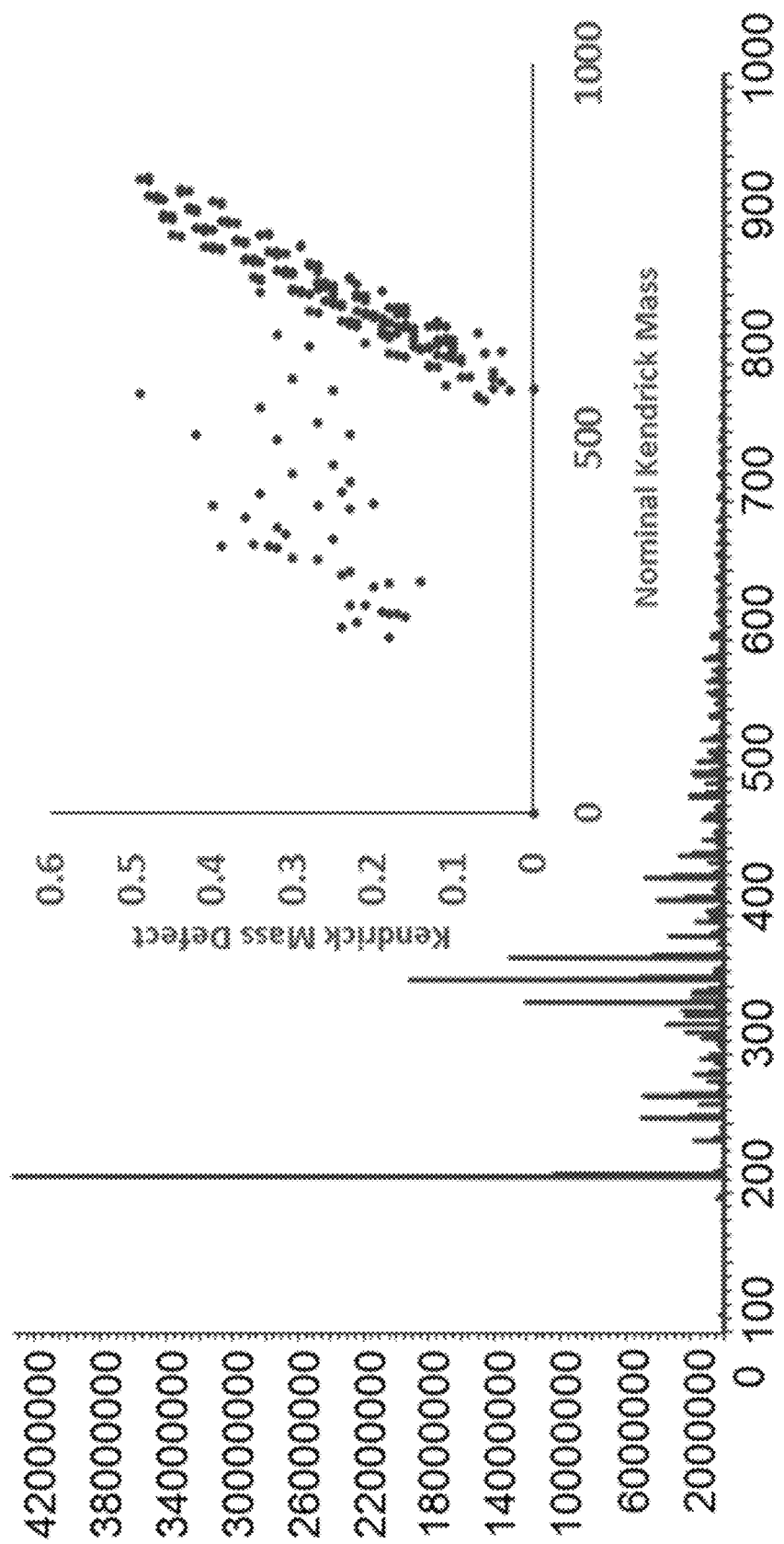

FIG. 34 shows a mass spectrum of the DOM composition and a Kendrick mass defect plot to display homologous $CH_2$ shifts indicative of DOM (inset) for *Scenedesmus* exposed to a high (20:4 h) light regime in the presence of Hg according to an example of the present application.

Figure 35:
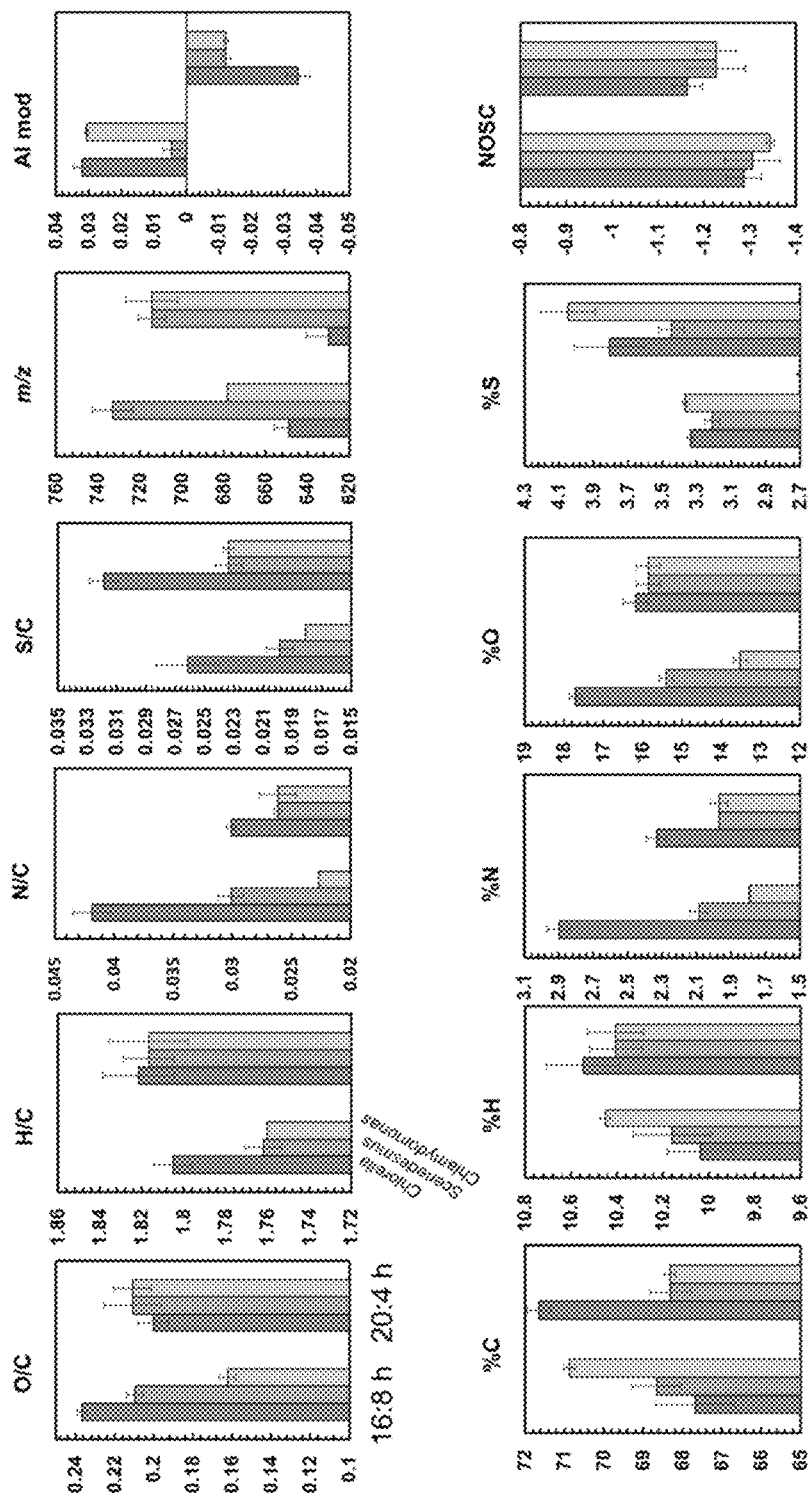

FIG. 35 shows plots of weighted average molecular characteristics (clockwise from top left: O/C, H/C, N/C, S/C, m/z, AI mod, NOSC, % S, % O, % N, % H and % C) of DOM produced from *Chlorella* (black bars), *Chlamydomonas* (light grey bars), and *Scenedesmus* (white bars) exposed to a standard (16:8 h) light regime (left three bars of each plot) or high (20:4 h) light regime (right three bars of each plot according to examples of the present application.

Figure 36:
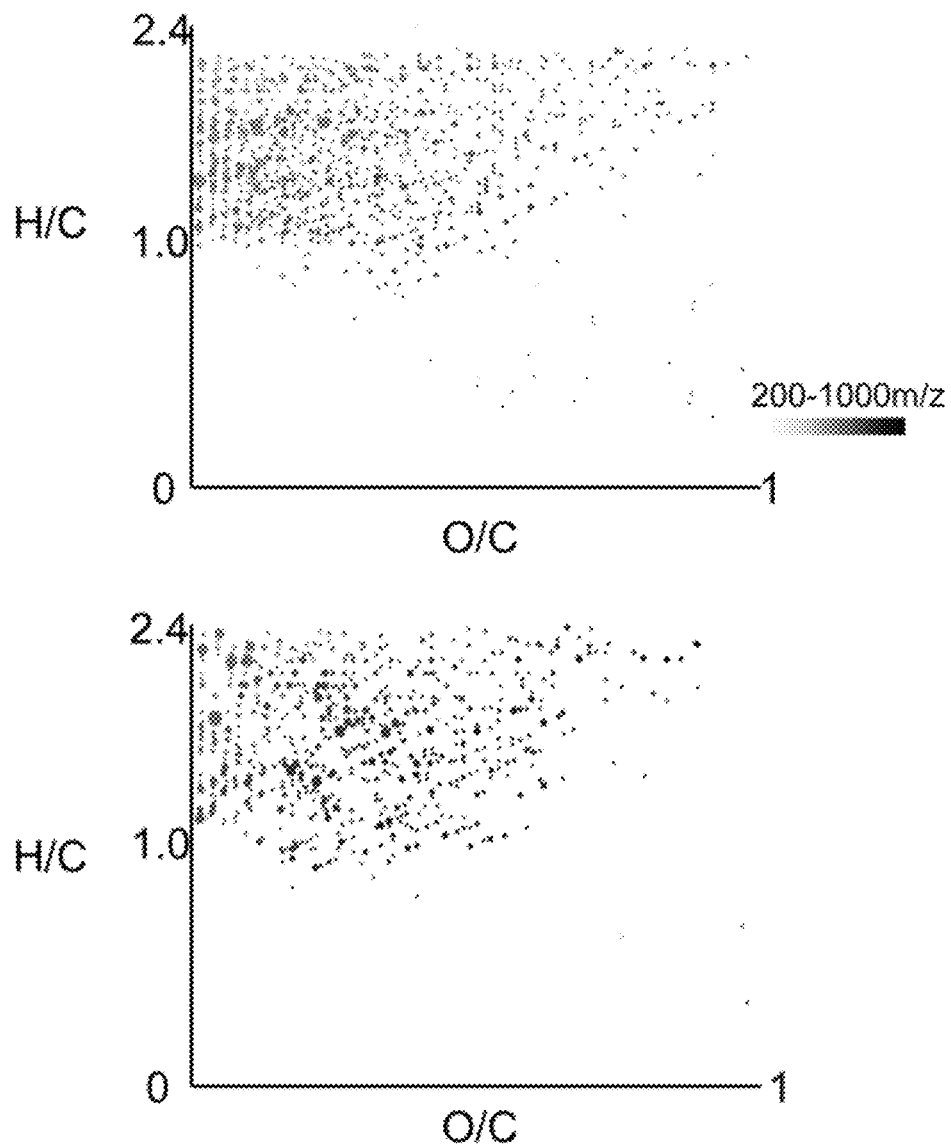

FIG. 36 shows van Krevelen diagrams of phytoplankton-derived DOM from *Chlorella* grown at 16:8 h (top) in comparison to 20:4 h (bottom) light:dark cycles according to examples of the present application. Darker shades correspond to molecules with greater m/z and larger point sizes correspond to greater peak intensity.

Figure 37:
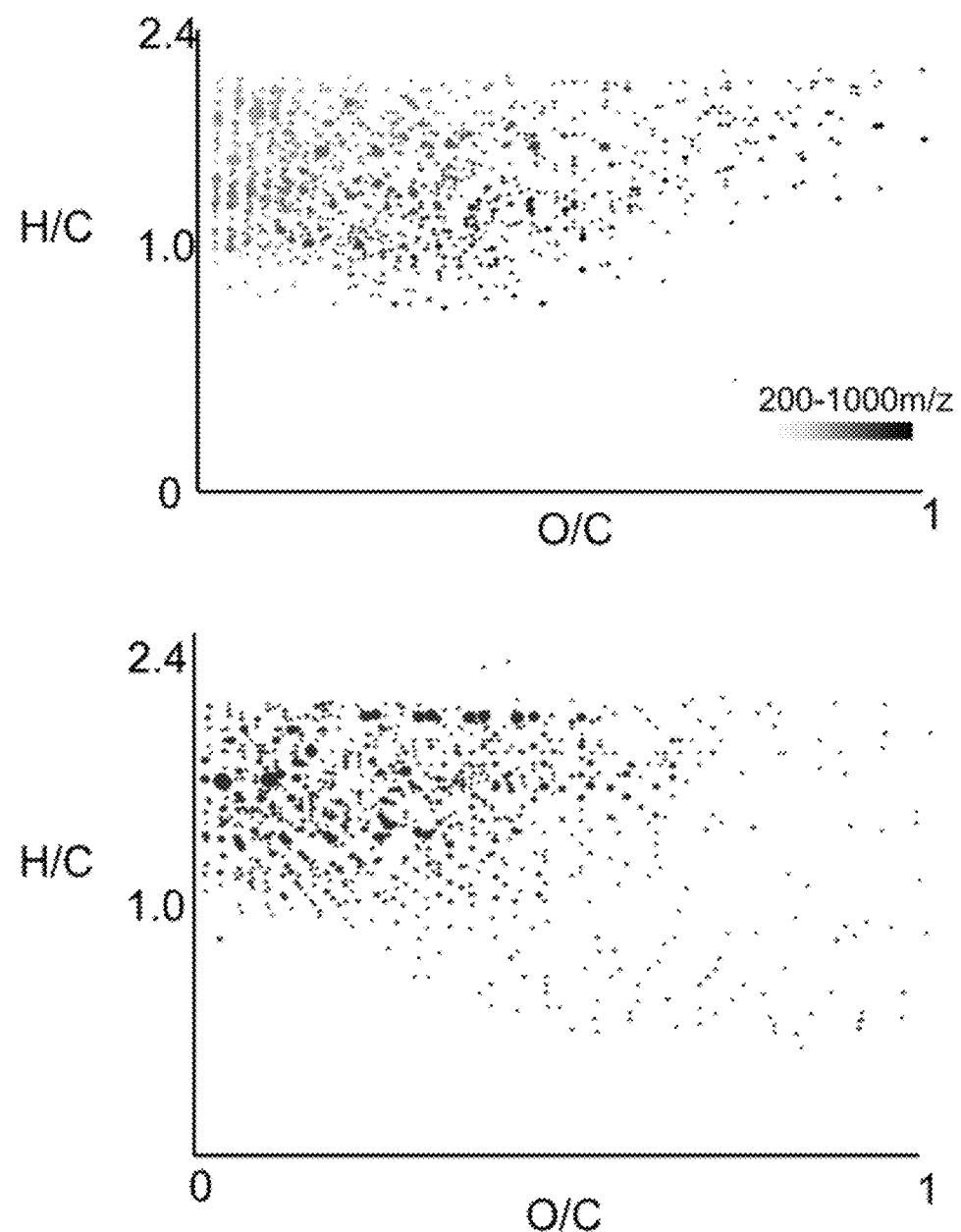

FIG. 37 shows van Krevelen diagrams of phytoplankton-derived DOM from *Chlamydomonas* grown at 16:8 h (top) in comparison to 20:4 h (bottom) light:dark cycles according to examples of the present application. Darker shades correspond to molecules with greater m/z and larger point sizes correspond to greater peak intensity.

Figure 38:
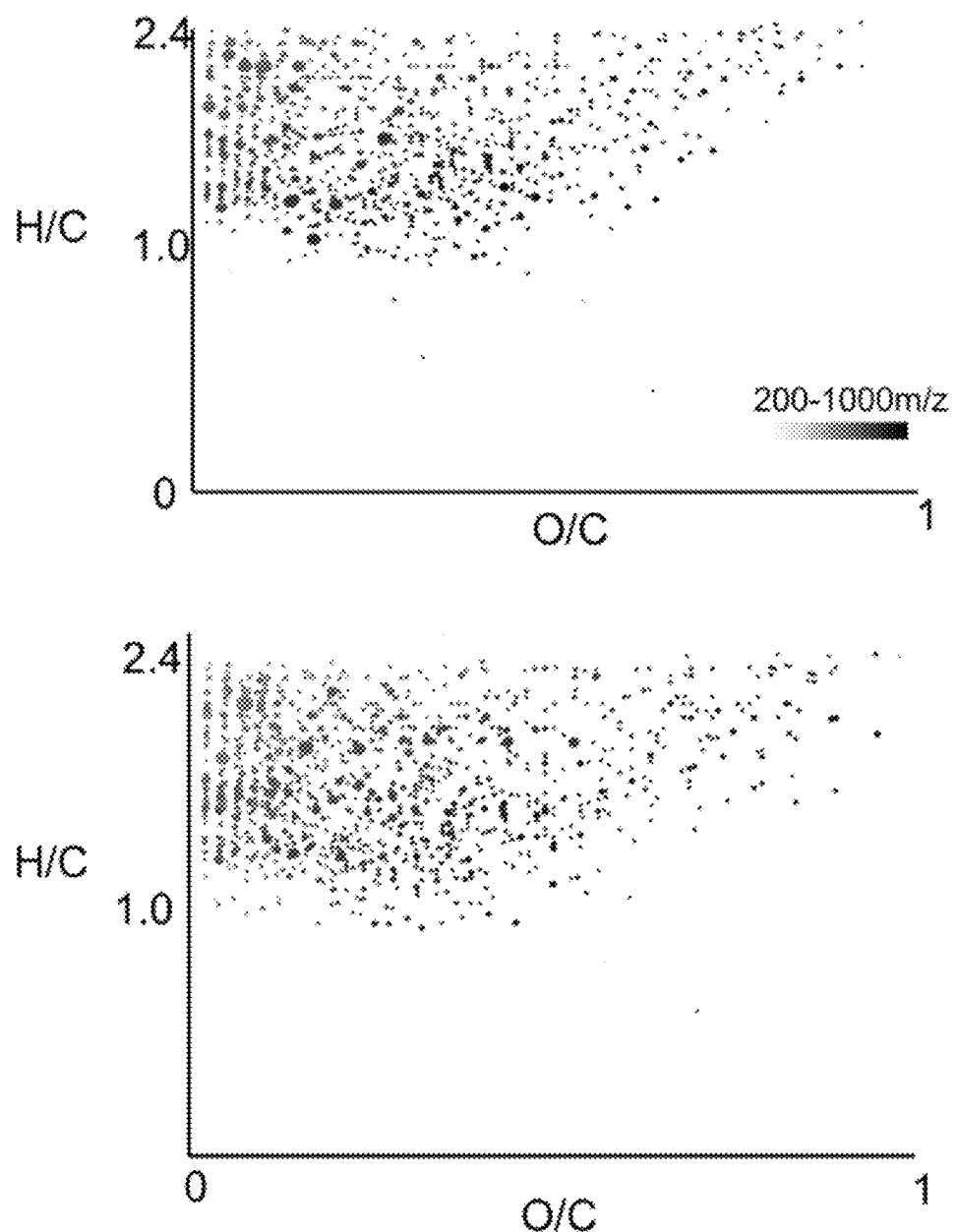

FIG. 38 shows van Krevelen diagrams of phytoplankton-derived DOM from *Scenedesmus* grown at 16:8 h (top) in comparison to 20:4 h (bottom) light:dark cycles according to examples of the present application. Darker shades correspond to molecules with greater m/z and larger point sizes correspond to greater peak intensity.

Figure 39:
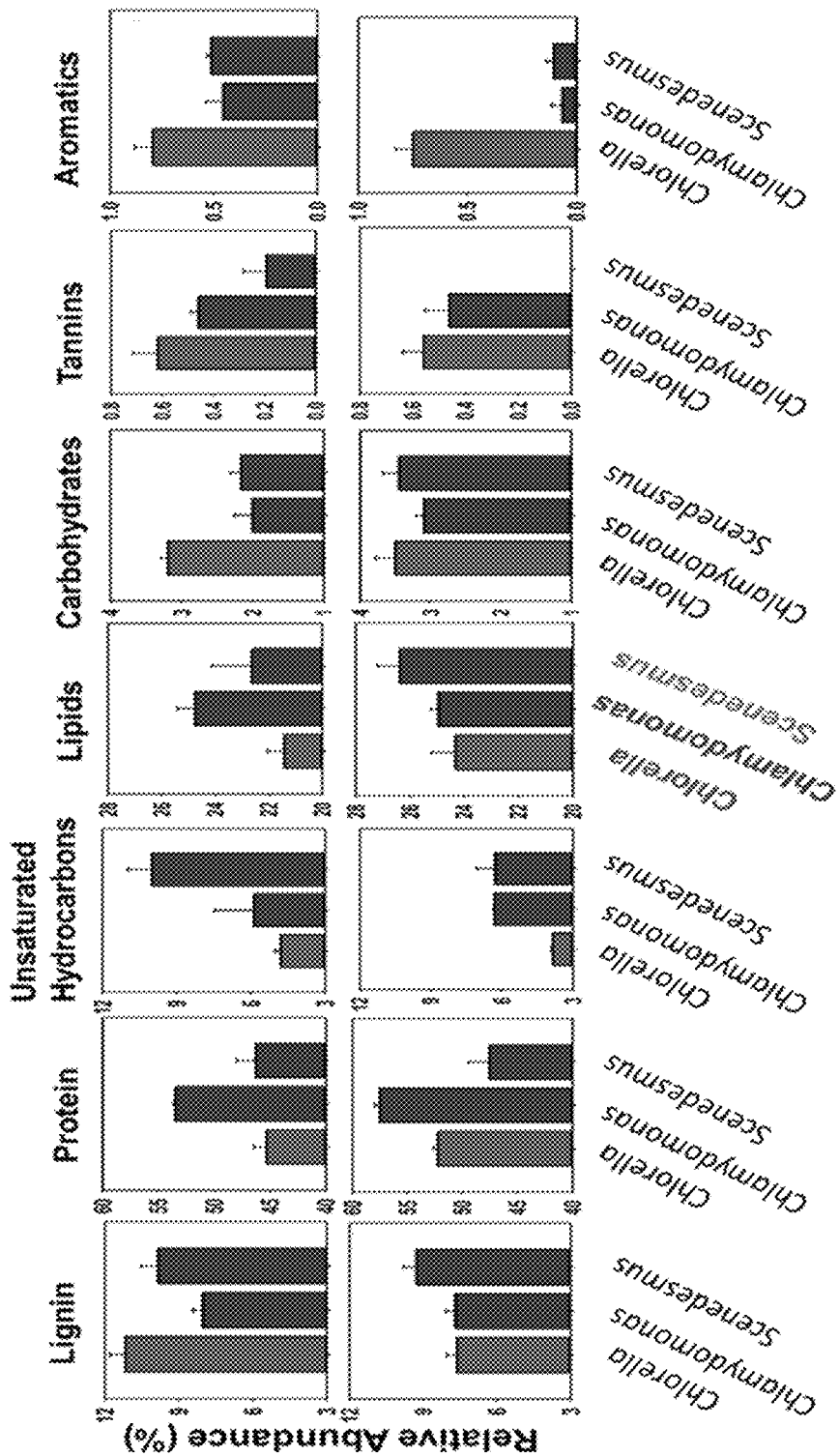

FIG. 39 shows compound classes based on van Krevelen diagrams portraying the relative abundance (%) of from left to right: lignin, protein, unsaturated hydrocarbons, lipids, carbohydrates, tannins and aromatic structures released by *Chlorella* (left), *Chlamydomonas* (middle) and *Scenedesmus* (right) grown at 16:8 h (top) in comparison to 20:4 h (bottom) light:dark cycles according to examples of the present application. Error bars for both 16:8 h and 20:4 h light:dark cycles are based on biological duplicates (n=2).

Figure 40:
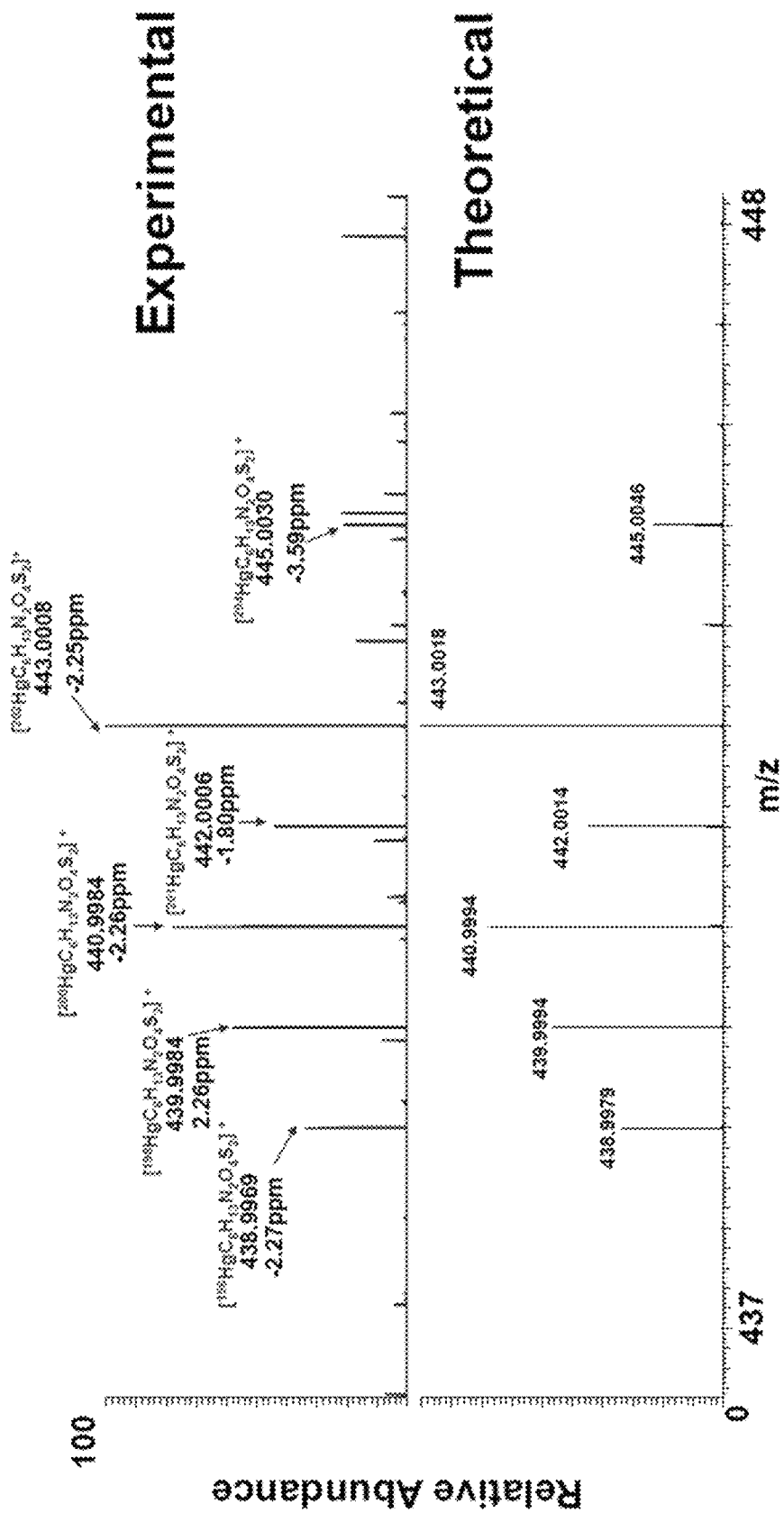

FIG. 40 shows detection of a Hg:Cysteine [$HgC_6H_{13}N_2O_4S_2$] complex at a 1:2 molar ratio and six detected Hg isotopologues ($^{204}$Hg, $^{202}$Hg, $^{201}$Hg, $^{200}$Hg, $^{198}$Hg, and $^{196}$Hg) (top) according to examples of the present application in comparison to the theoretical isotopic distribution (bottom); relative abundances of each isotope agree. Exact mass comparison also revealed mass accuracy of ±5 ppm for Hg isotopes.

Figure 41:
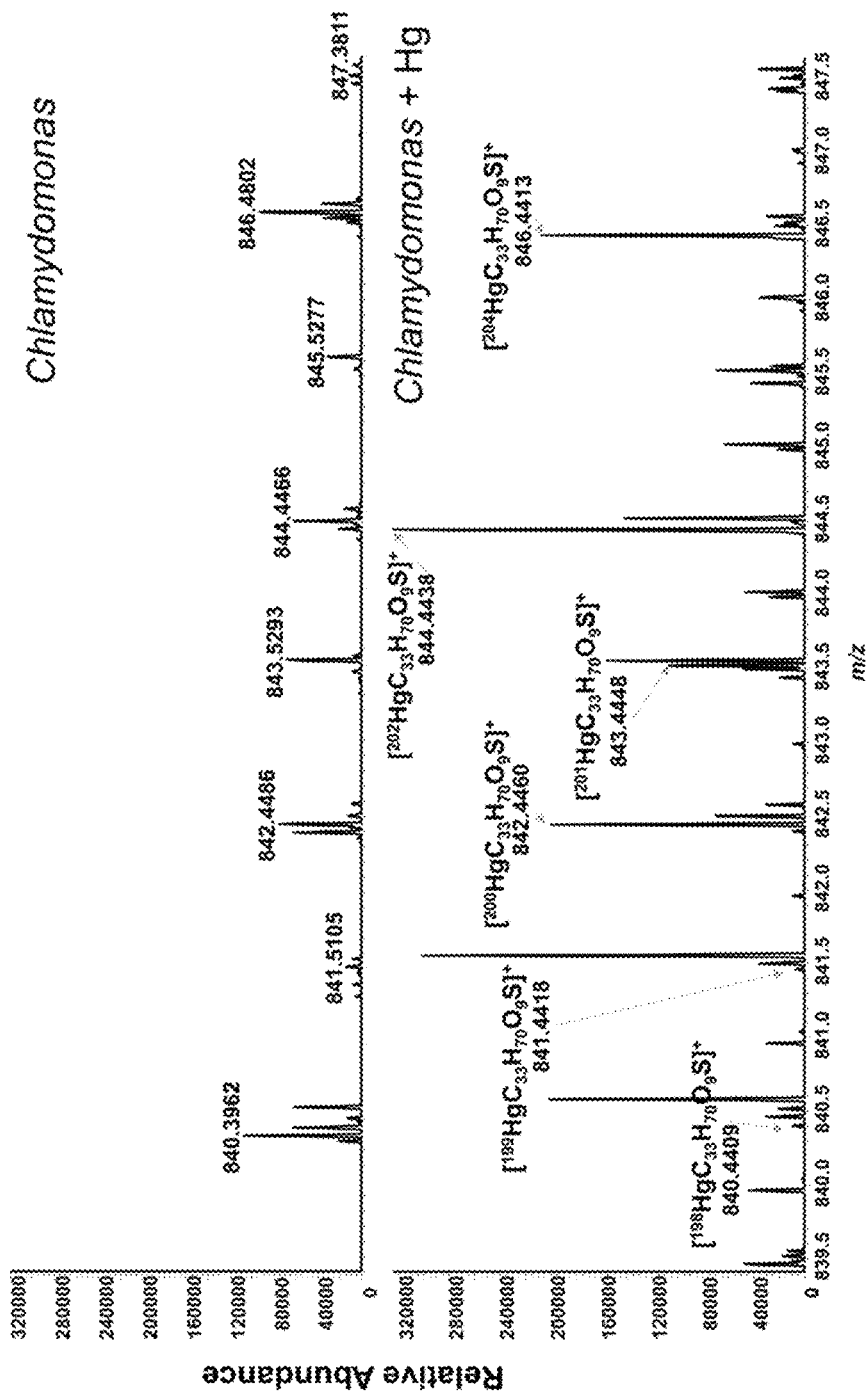

FIG. 41 shows mass spectra of DOM from *Chlamydomonas* in the absence (top) and presence (bottom) of Hg indicating the presence of Hg isotopologues after the Hg addition.

Figure 42:
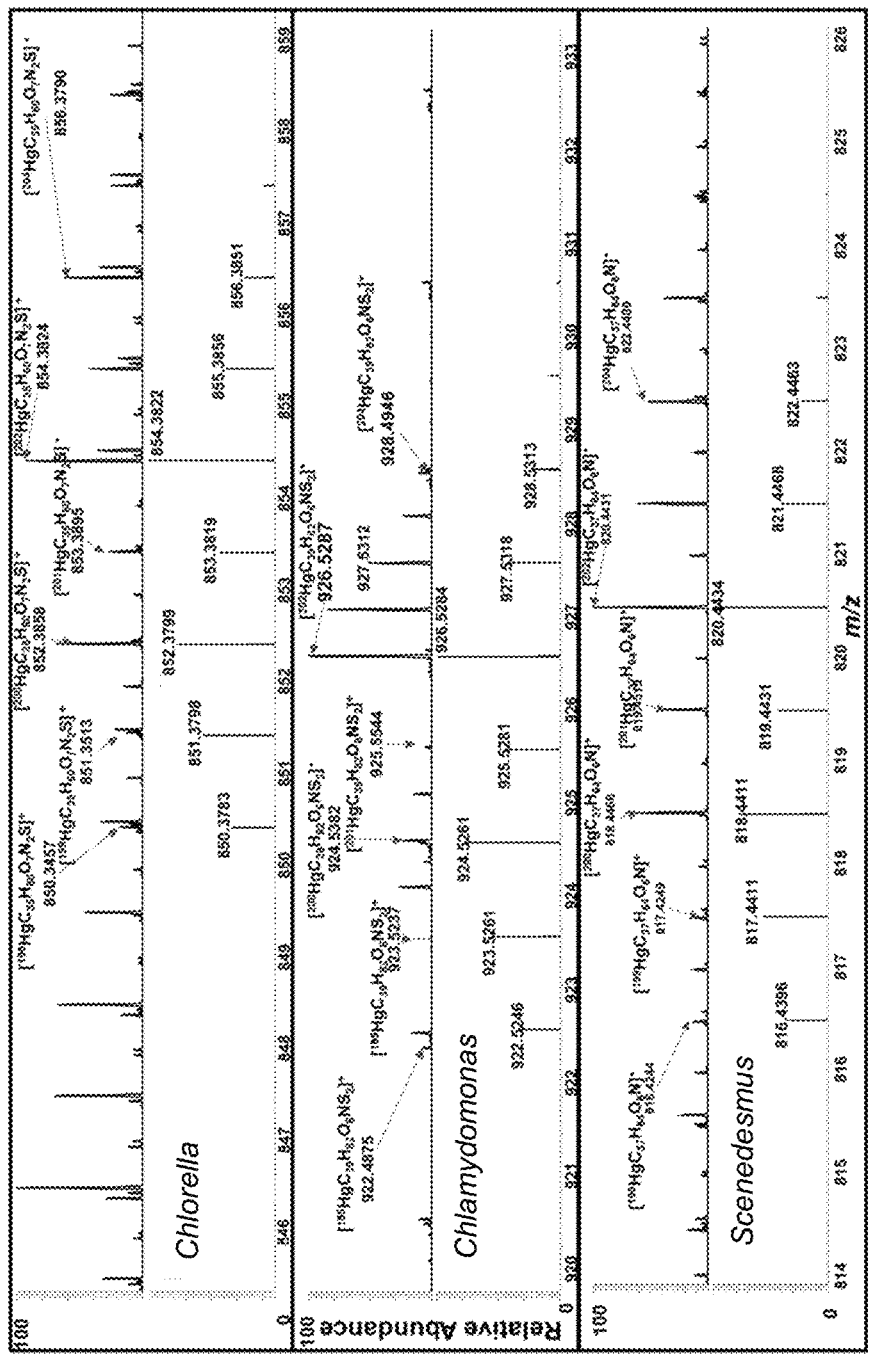

FIG. 42 shows identified Hg containing DOM for *Chlorella*, (top) *Chlamydomonas* (third from top) and *Scenedesmus* (second from bottom) according to examples of the present application, in comparison to corresponding spectra of the theoretical isotopic distribution (second from top, third from bottom and bottom, respectively).

Figure 43:
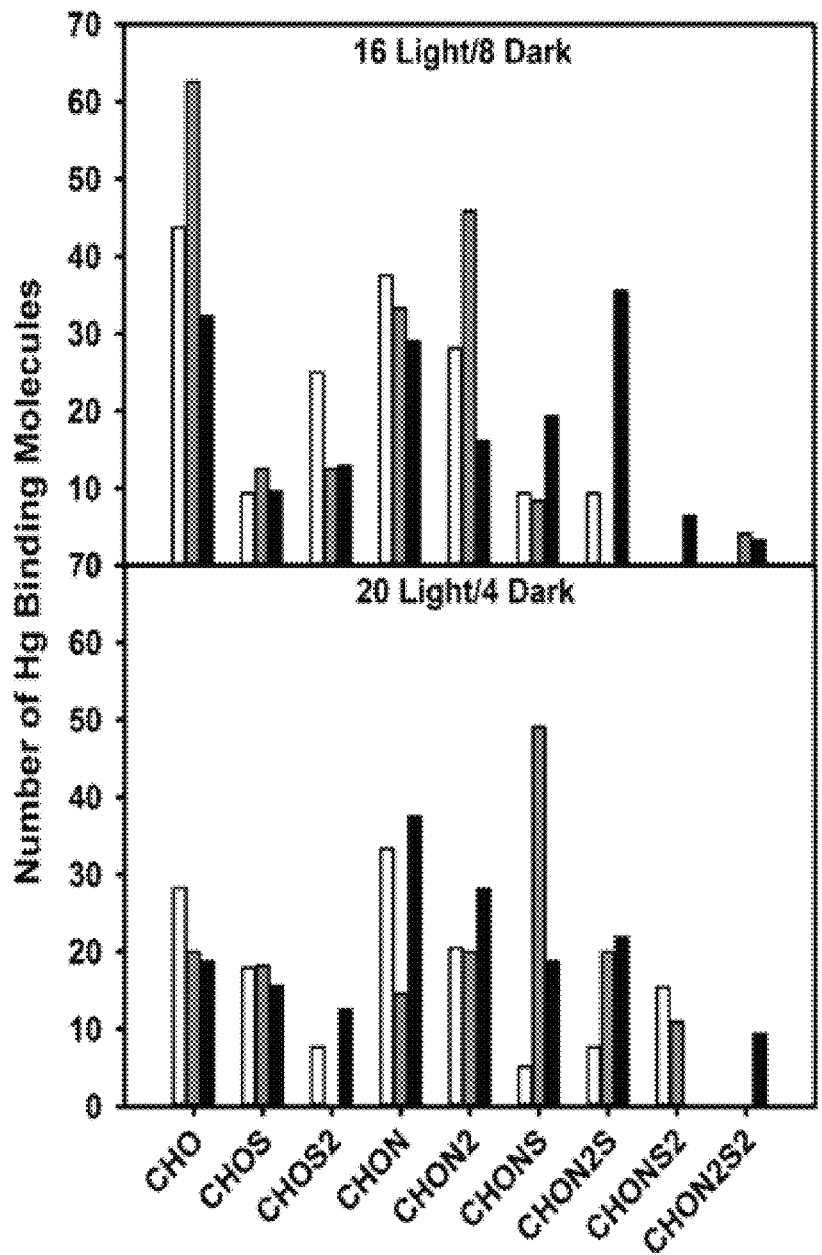

FIG. 43 shows plots wherein based on exact mass and isotopic conformation, the abundance of Hg binding DOM at 16:8 h (top) and 20:4 h (bottom) according to examples of the present application were grouped based on generic molecular formula. White bars: *Chlorella*, grey bars: *Chlamydomonas*, and black bars: *Scenedesmus*.

Figure 44:
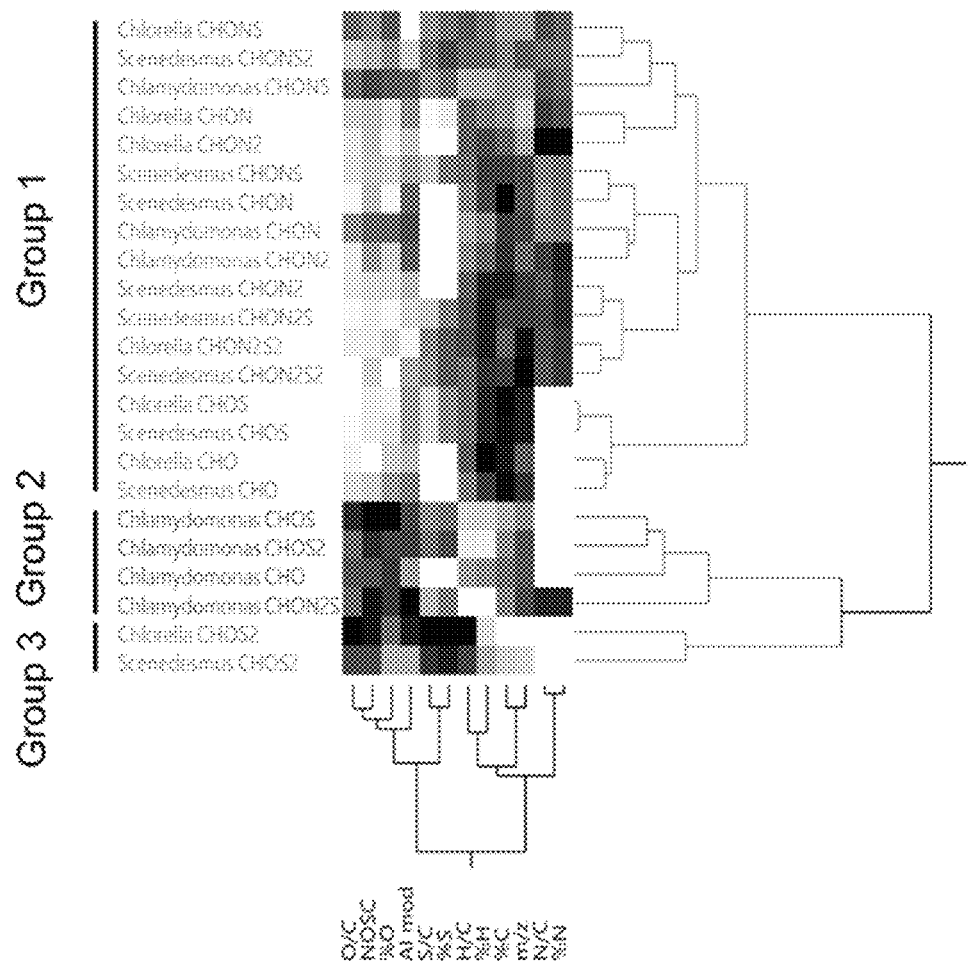

FIG. 44 shows two-way hierarchical cluster analysis based on structural properties of Hg binding DOM at a 16:8 h light cycle according to an example of the present application. A Spearman's correlation matrix also portrays the overall weight of each molecular group to a structural property where darker colorations indicate a stronger correlation.

Figure 45:
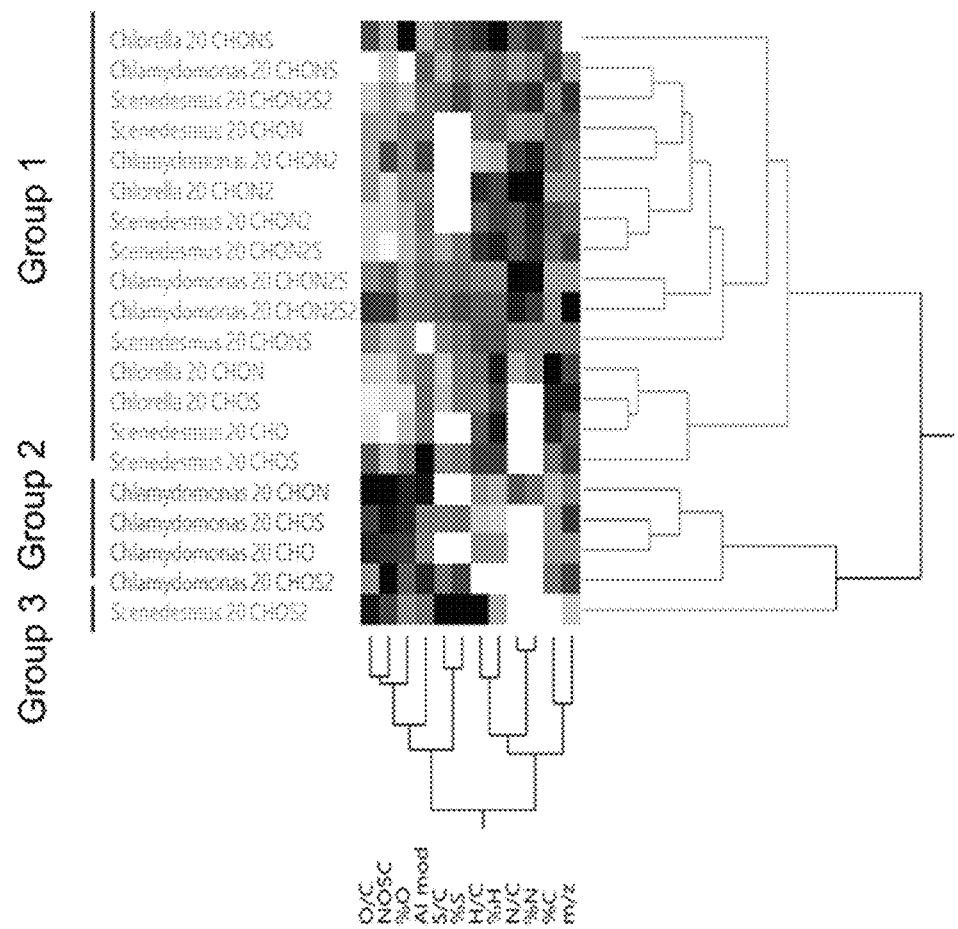

FIG. 45 shows two-way hierarchical cluster analysis based on structural properties of Hg binding DOM at a 20:4 h light cycle according to examples of the present application. A Spearman's correlation matrix also portrays the overall weight of each molecular group to a structural property where darker colorations indicate a stronger correlation.

Figure 46:
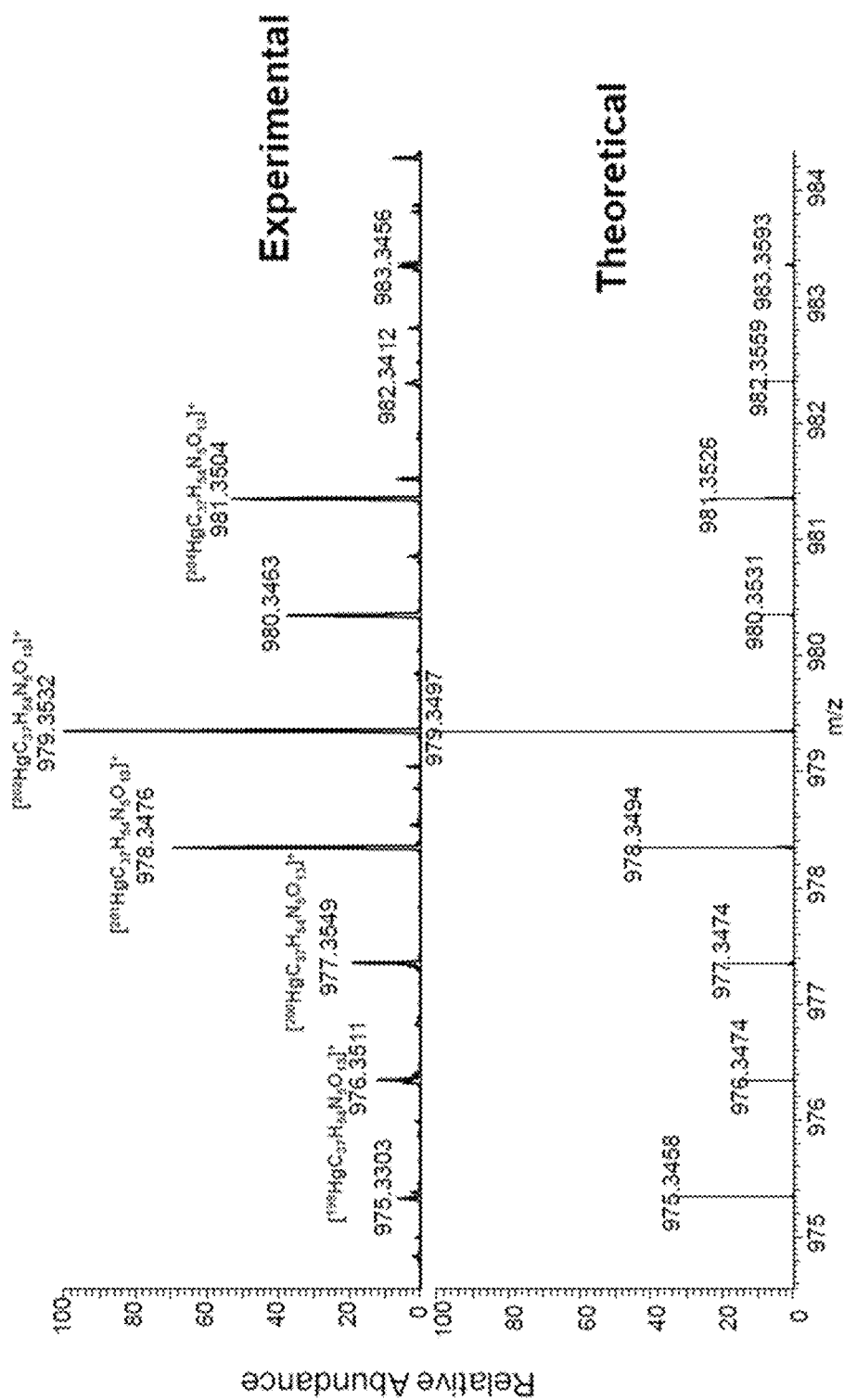

FIG. 46 shows an experimental mass spectrum (top) compared to the corresponding theoretical mass spectrum (bottom) for the identification of a putative isomer of the bacterial siderophore carboxymycobactins with an empirical formula of $HgC_{37}H_{54}N_5O_{13}$ found in *Chlorella* 20:4 h cultures according to an example of the present application.

Figure 47:
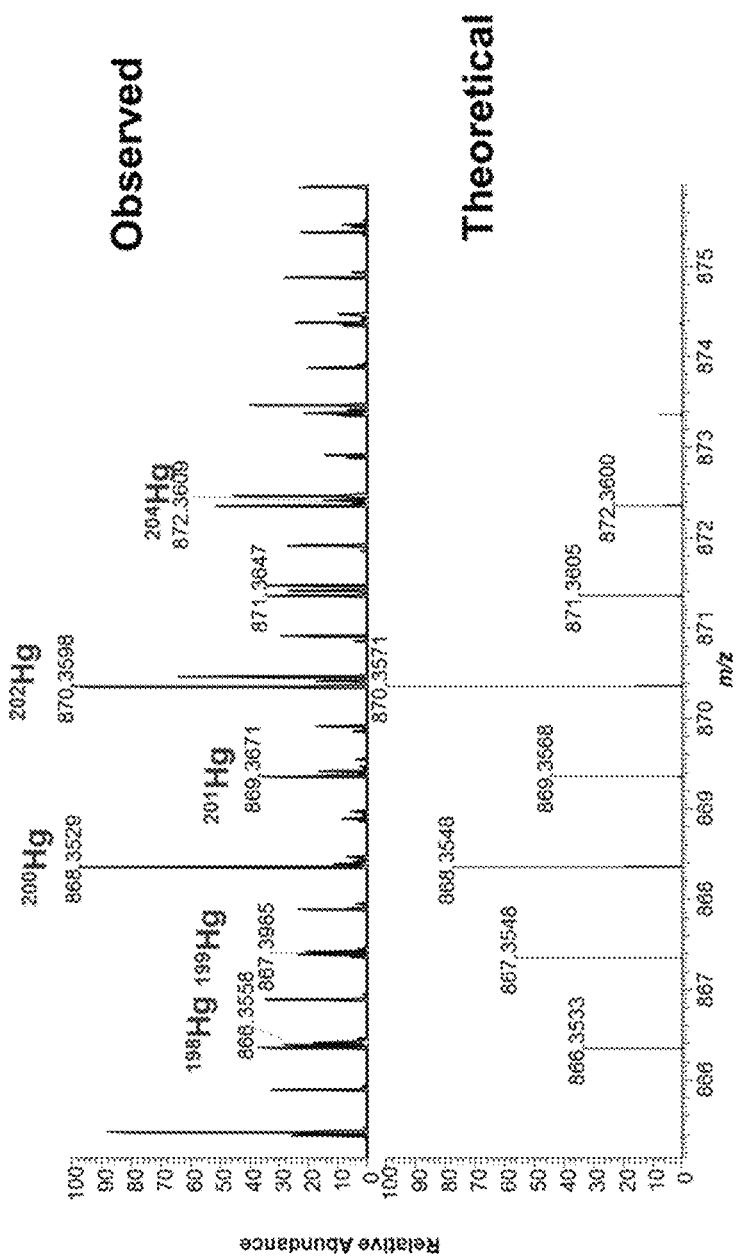

FIG. 47 shows an observed mass spectrum (top) compared to the corresponding theoretical mass spectrum (bottom) for possible isomers of Hg binding ligands based on exact mass and Hg isotopic distributions of acinetoferrin with an empirical formula of $C_{32}H_{54}N_5O_{10}Hg$ according to an example of the present application.

Figure 48:
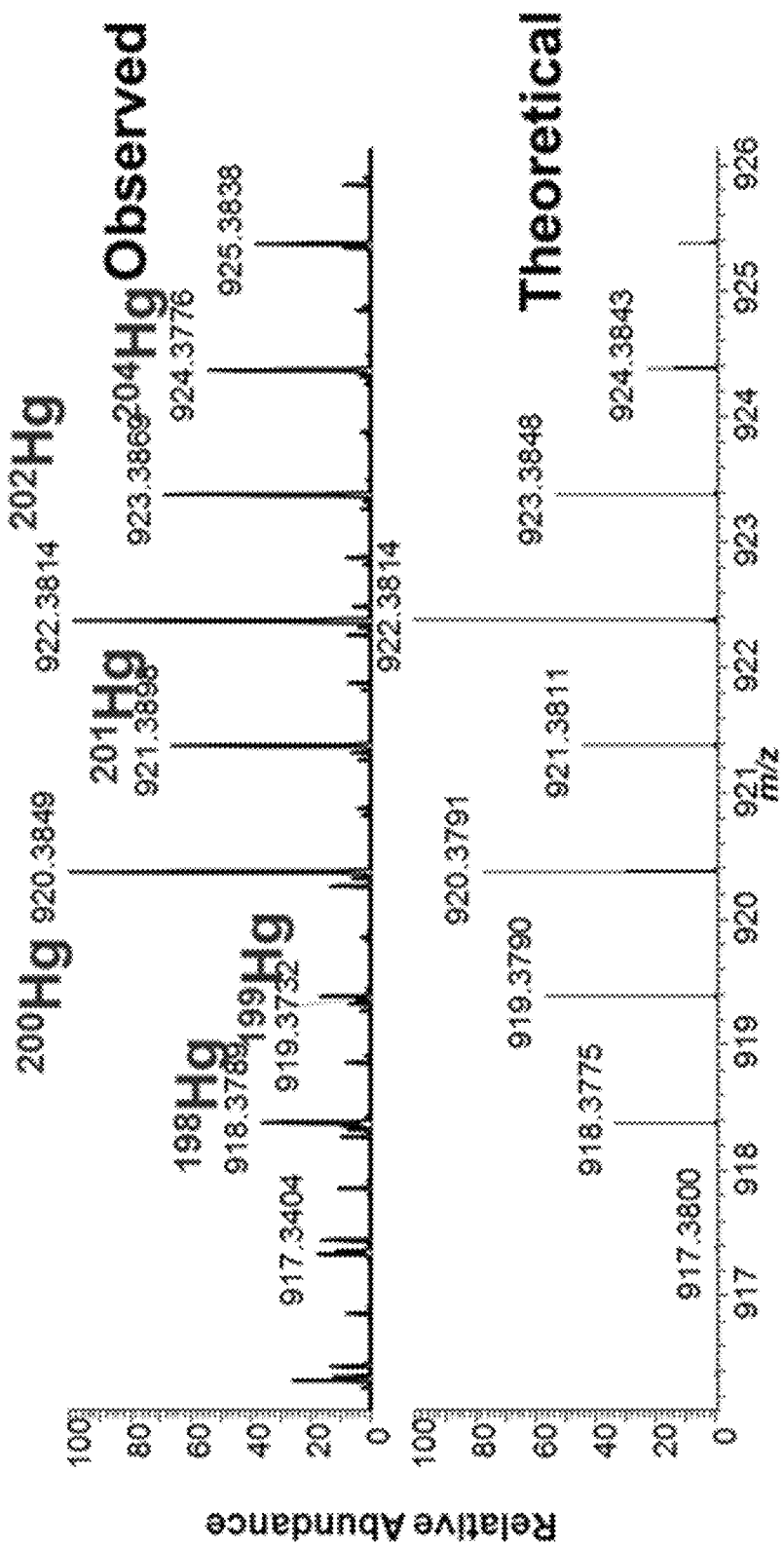

FIG. 48 shows an observed mass spectrum (top) compared to the corresponding theoretical mass spectrum (bottom) for possible isomers of Hg binding ligands based on exact mass and Hg isotopic distributions of desferrioxamine G1 with an empirical formula of $C_{27}H_{49}N_6O_{10}Hg+ C_4H_7NO+H_2O+Hg$ according to an example of the present application.

Figure 49:
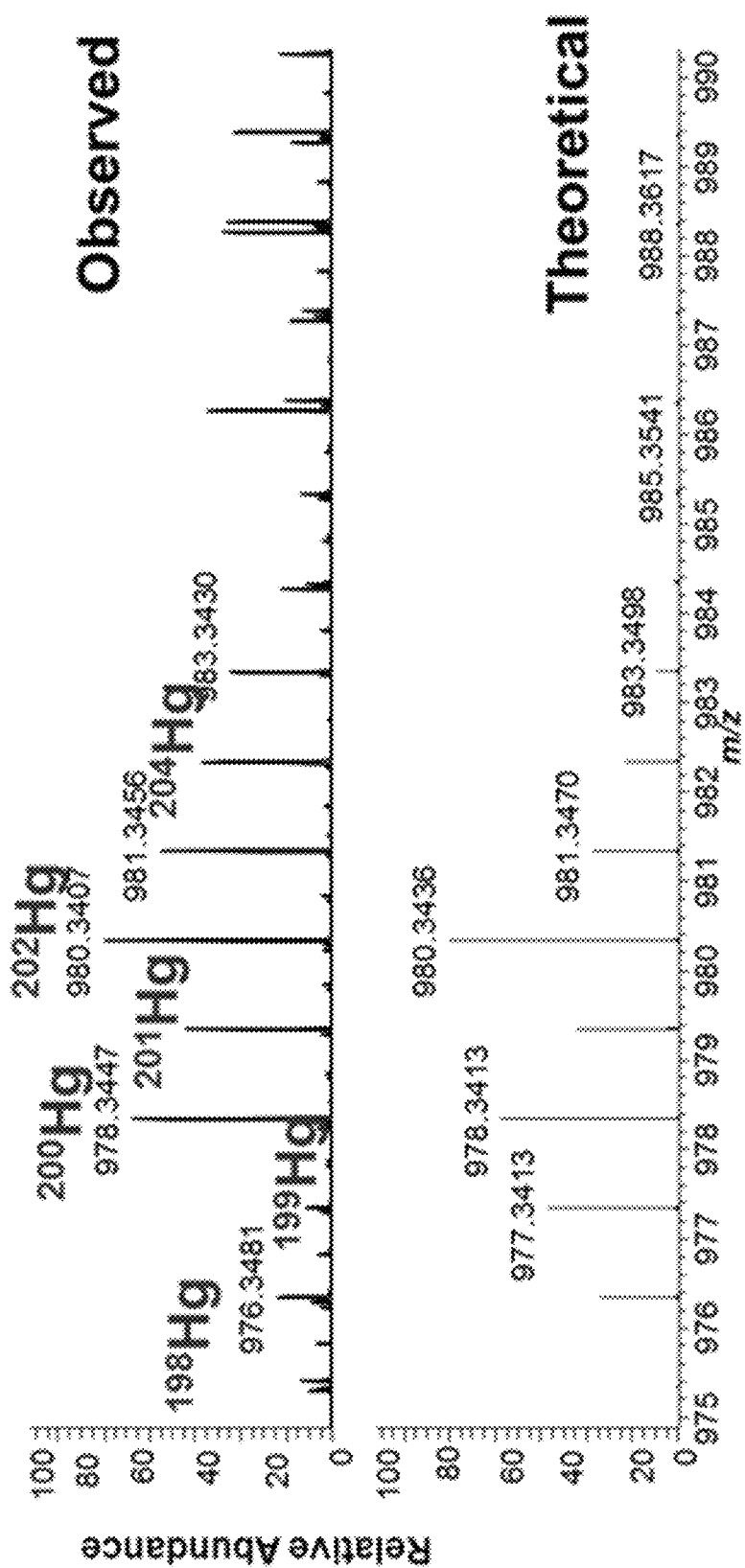

FIG. 49 shows an observed mass spectrum (top) compared to the corresponding theoretical mass spectrum (bottom) for possible isomers of Hg binding ligands based on exact mass and Hg isotopic distributions of cyclic trichirsobactin with an empirical formula of $C_{41}H_{57}N_9O_{12}+Hg$ according to an example of the present application.

Figure 50:
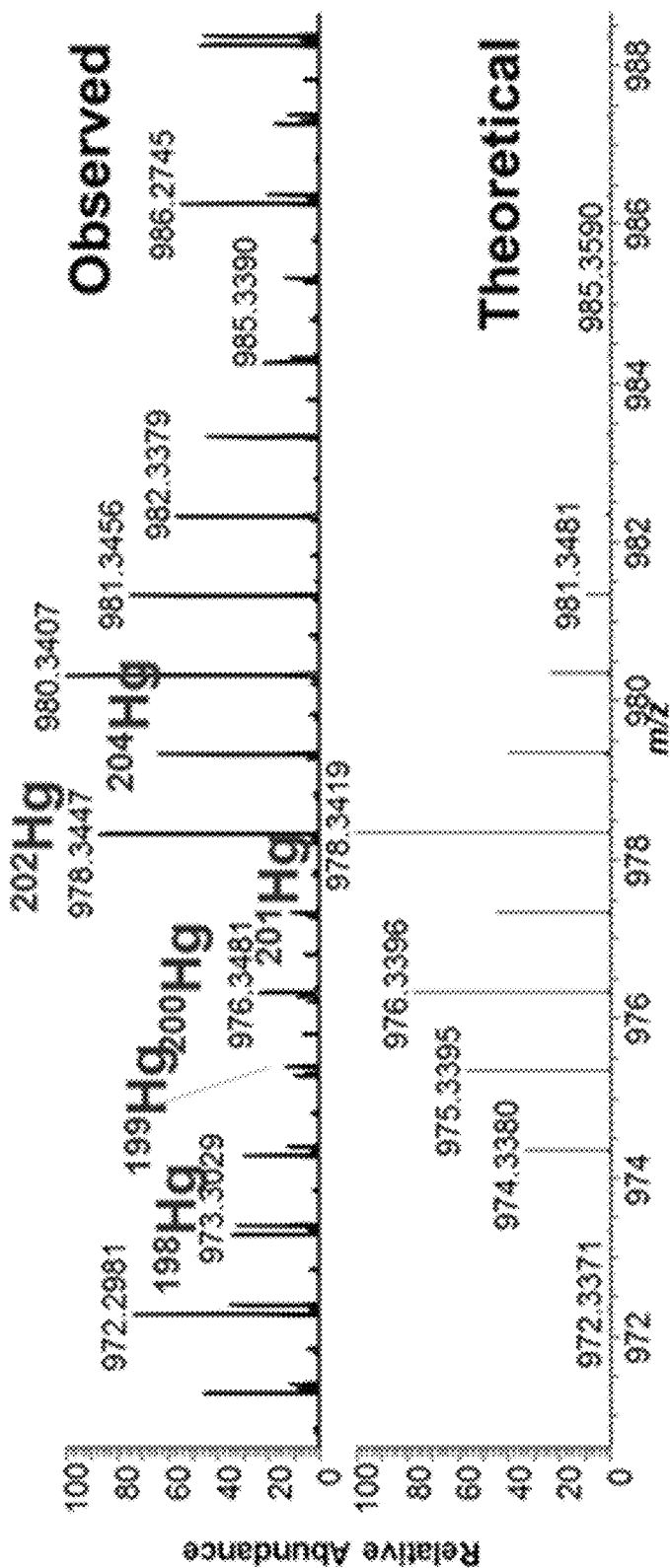

FIG. 50 shows an observed mass spectrum (top) compared to the corresponding theoretical mass spectrum (bottom) for possible isomers of Hg binding ligands based on exact mass and Hg isotopic distributions of carboxymycobactin with an empirical formula of $C_{29}H_{32}N_5O_{13}+Hg$ according to an example of the present application.

Figure 51:
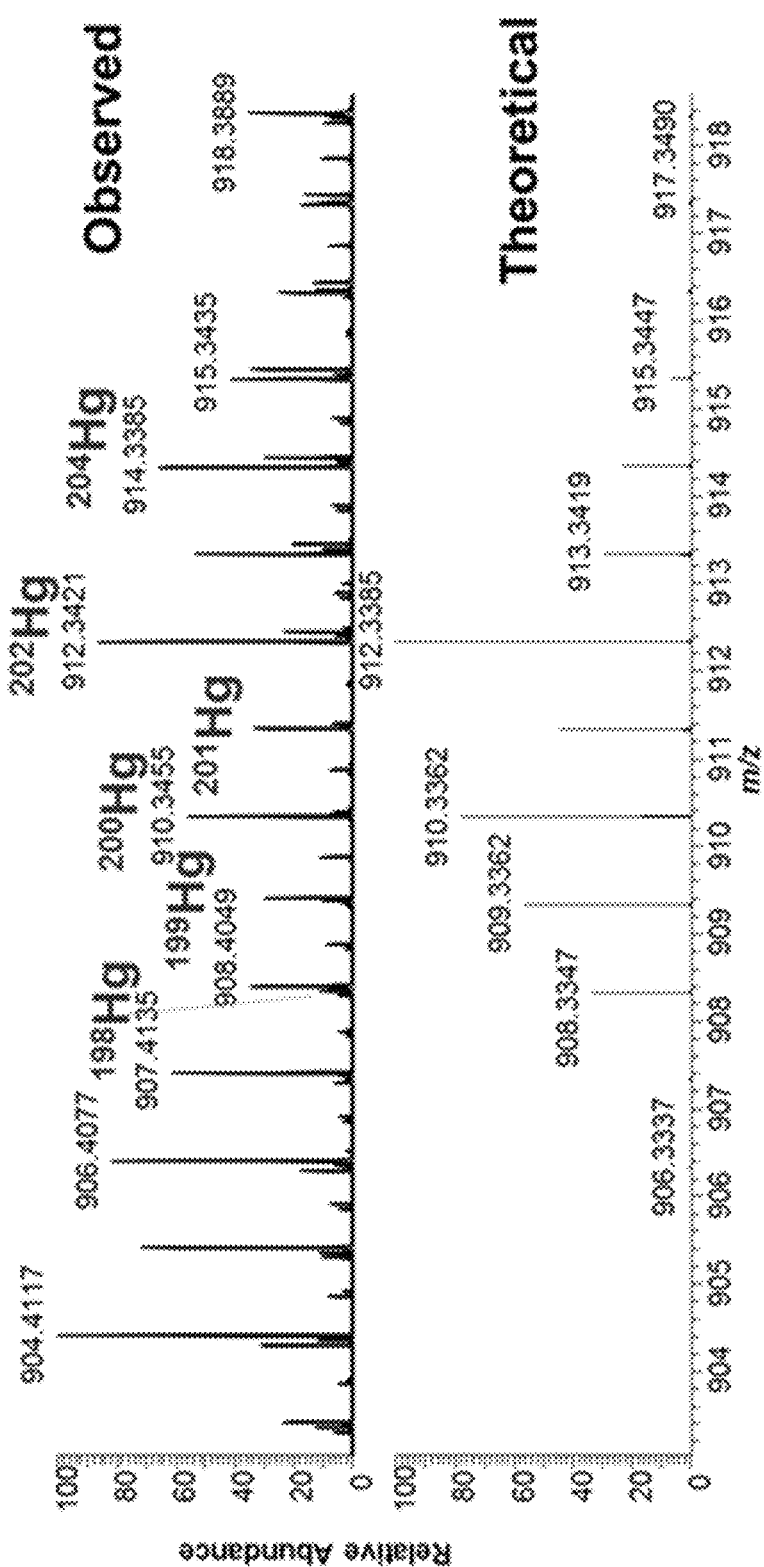

FIG. 51 shows an observed mass spectrum (top) compared to the corresponding theoretical mass spectrum (bottom) for possible isomers of Hg binding ligands based on exact mass and Hg isotopic distributions of exochelin with an empirical formula of $C_{27}H_{53}N_{10}O_{12}+Hg$ according to an example of the present application.

Figure 52:
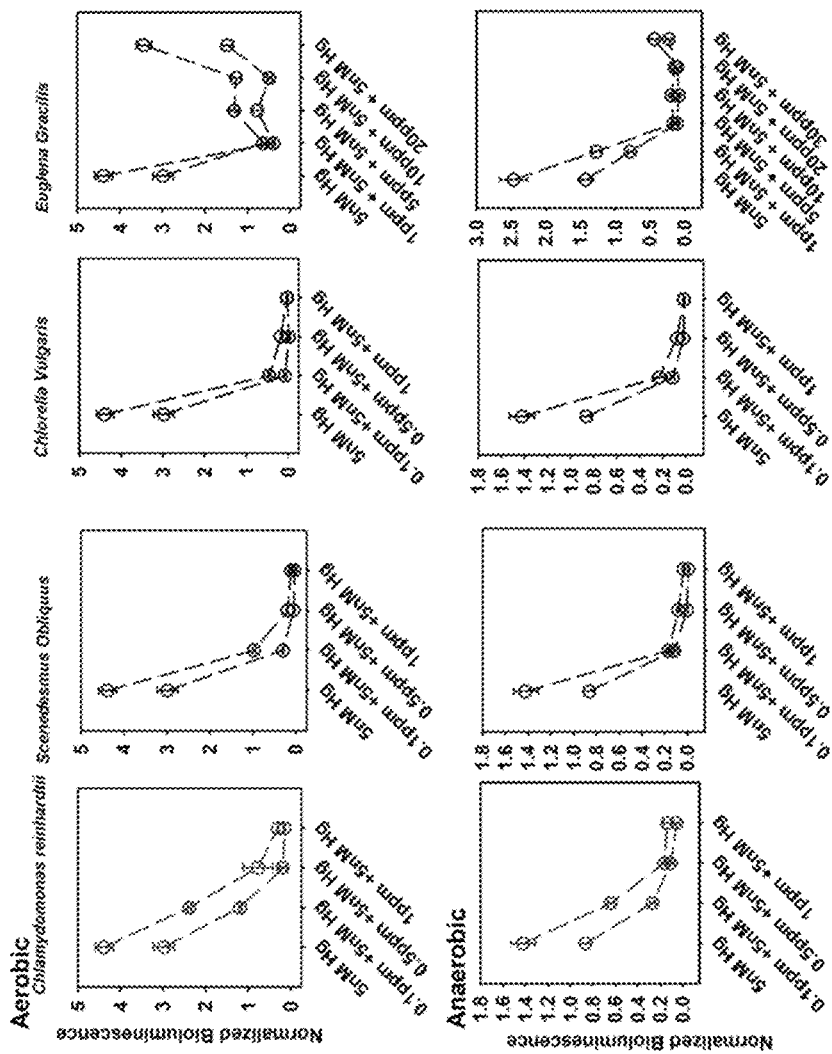

FIG. 52 shows the effect of DOM concentration on Hg mobility for from left to right: *Chlamydomonas reinhardttii, Scenedesmus obliguus, Chlorella vulgaris* and *Euglena gracilis* according to examples of the present application under aerobic (top) and anaerobic (bottom) conditions.

Figure 53:
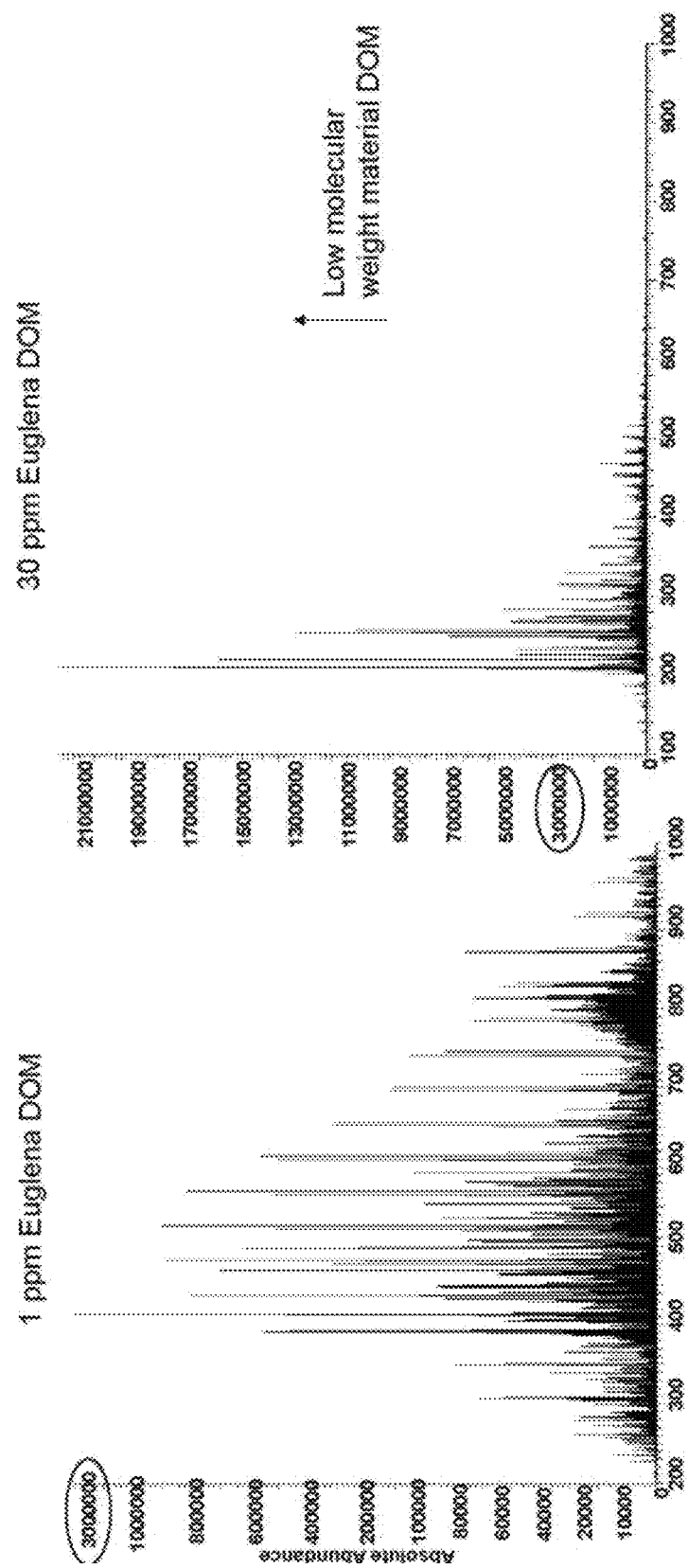

FIG. 53 shows the effect of a DOM concentration of 1 ppm (left) compared to a DOM concentration of 30 ppm (right) according to examples of the present application on the production and release of DOM molecules of various molecular weights by *Euglena gracilis*.

Figure 54:
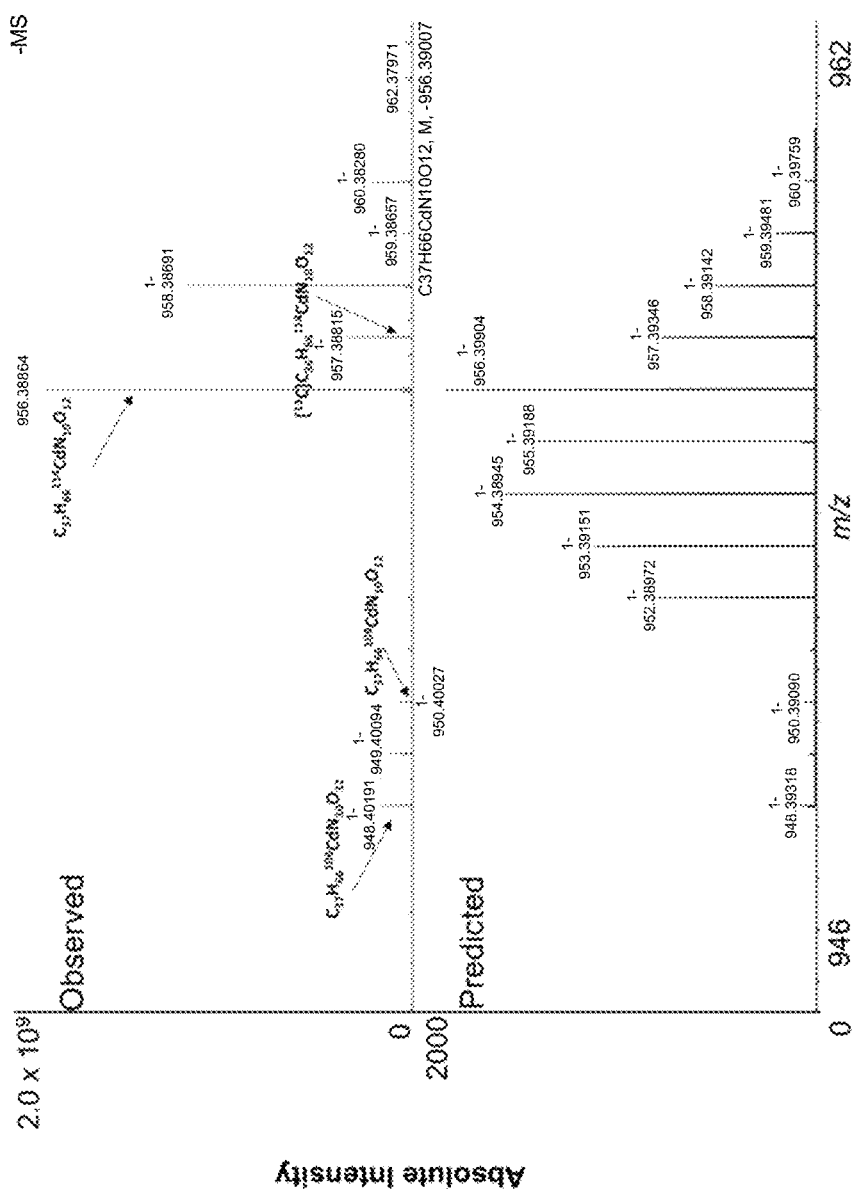

FIG. 54 shows an observed mass spectrum (top) compared to the corresponding predicted mass spectrum (bottom) for oligopeptides—Cd complex according to an example of the present application.

Figure 55:
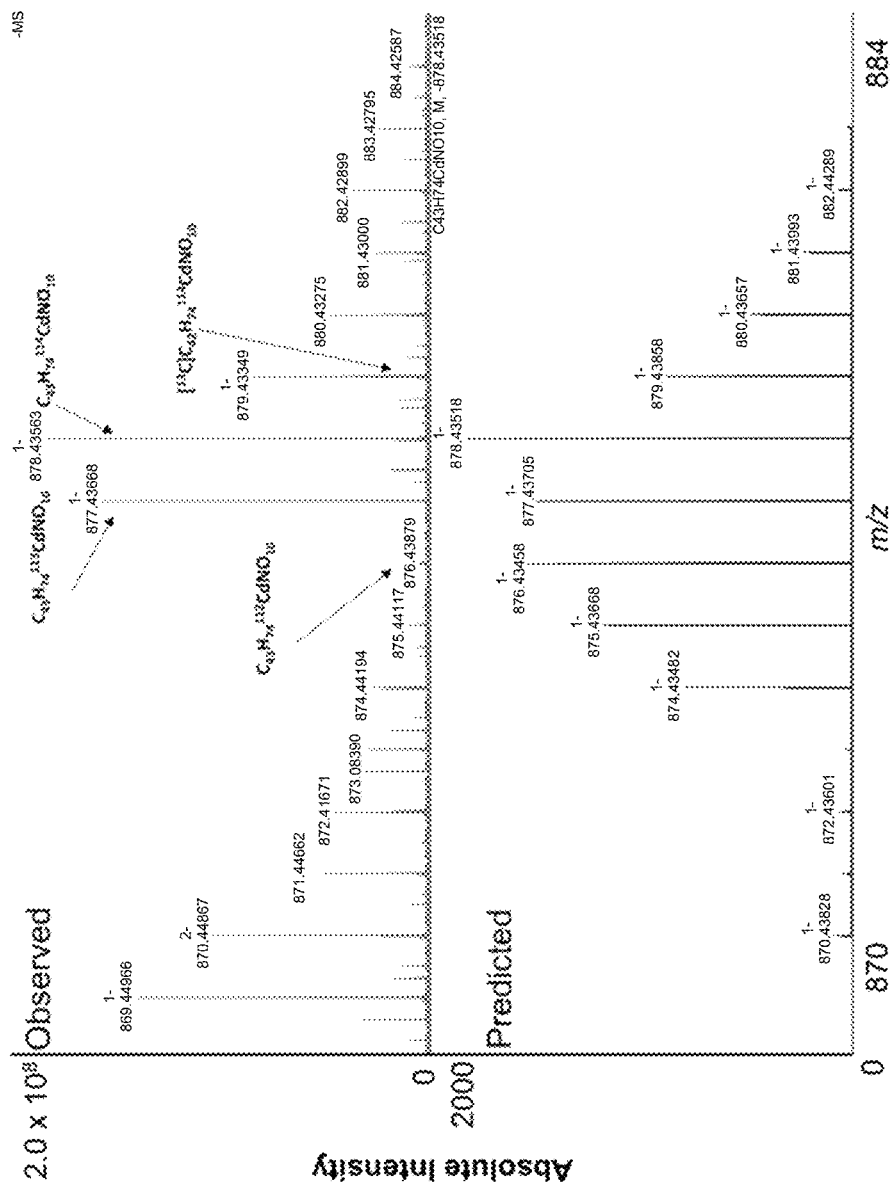

FIG. 55 shows an observed mass spectrum (top) compared to the corresponding predicted mass spectrum (bottom) for bacteriohopanetetrol cyclitol ether—Cd complex according to an example of the present application.

Figure 56:
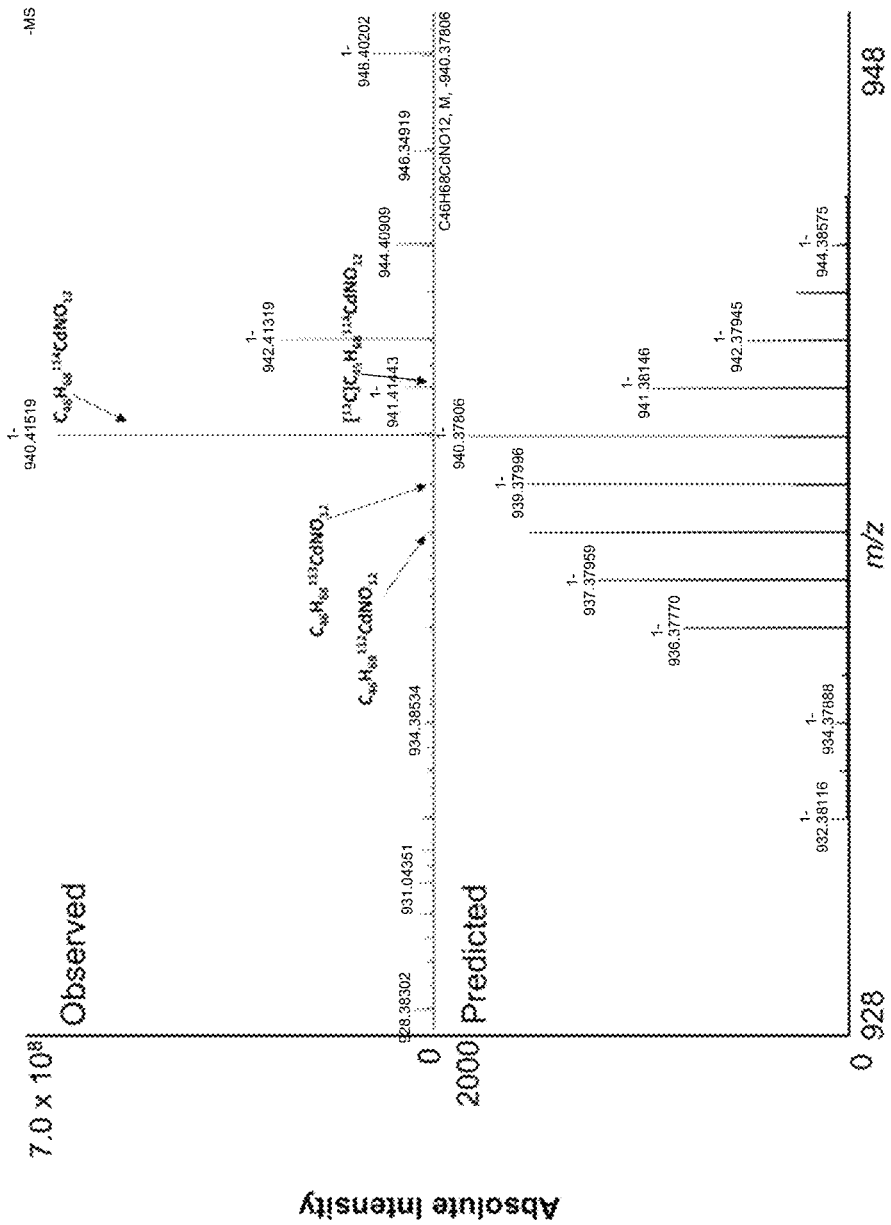

FIG. 56 shows an observed mass spectrum (top) compared to the corresponding predicted mass spectrum (bottom) for Azaspiracid-3-Cd complex according to an example of the present application.

Figure 57:
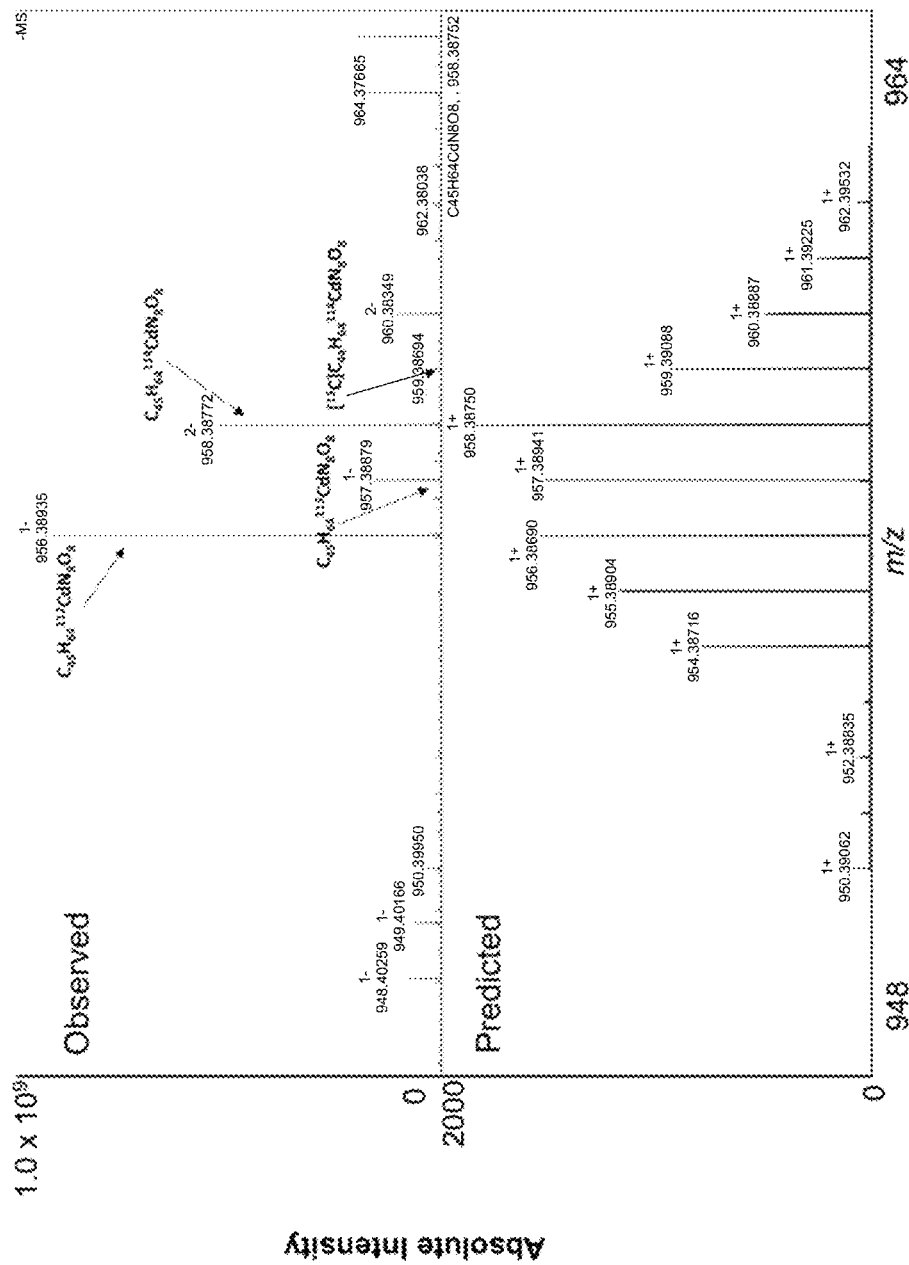

FIG. 57 shows an observed mass spectrum (top) compared to the corresponding predicted mass spectrum (bottom) for Brunsvicamide A—Cd complex according to an example of the present application.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

As used in this application, the singular forms "a", "an" and "the" include plural references unless the content clearly dictates otherwise.

In embodiments comprising an "additional" or "second" component, the second component as used herein is different from the other components or first component. A "third" component is different from the other, first, and second components, and further enumerated or "additional" components are similarly different.

II. Methods and Uses

Dissolved organic matter (DOM) is a dynamic ligand with properties that can govern the fate of mercury in natural systems. Whereas the production of monomethylmercury occurs under anoxic conditions, $Hg^{II}$ first interacts with DOM under oxic conditions upon deposition from the atmosphere but studies investigating such interactions have been scarce. The present examples investigated the role of DOM (Suwannee River (SRFA) and Pony Lake (PLFA) fulvic acids), on Hg bioavailability using a multi-pronged approach relying on asymmetrical flow field-flow fractionation for DOM molecular weight separation, high resolution mass spectrometry for resolved compositional assessment, coupled to a whole-cell biosensor designed to quantify $Hg^{II}$ uptake. It was shown that size fraction affects $Hg^{II}$ bioavailability wherein lower molecular weight (MW) size fractions of SRFA abundant in small aliphatic material favors $Hg^{II}$ uptake, while not wishing to be limited by theory, supporting the role for low molecular weight (LMW) compounds of DOM acting as an shuttle to microorganisms. High molecular weight (HMW: 1800-3500 Da) fractions made up of larger aromatic material significantly reduced Hg bioavailability for both SRFA and PLFA ($p<0.05$). The present examples demonstrated the usefulness of LMW aliphatic DOM enhancing $Hg^{II}$ bioavailability in oxic environments suggesting, while not limited by theory, that differences in $Hg^{II}$ bioavailability are not solely driven by nitrogen and sulfur content, but also by MW and aromaticity characteristics.

Accordingly, the present application includes a method of binding a metal ion (or species) in water, the method comprising:
  contacting the water with a fraction of dissolved organic material (DOM) to form a complex between the DOM fraction and the metal ion; and
  optionally separating the complex from the water.

The term "water" as used herein includes water in the form of a solution, suspension or slurry.

The term "hydrate form" as used herein refers to a substance that contains water in its solid form optionally its crystalline form.

The fraction of DOM can be any suitable fraction of DOM. For example, in the studies of the present disclosure, a significant increase in cellular mercury mobilization was observed when microorganisms were exposed to a low molecular weight organic compound fraction of the DOM. Accordingly, in an embodiment, the fraction of DOM is a low molecular weight organic compound fraction of the DOM (LMW-DOM). In another embodiment, the LMW-DOM contains molecular weights ranging from 150-900 or 300-900 Da. In another embodiment, the LMW-DOM contains molecular weights from at least 100, 150, 200, 250, 300, 350 or 400 Da. In another embodiment, the LMW-DOM contains molecular weights to at most 700, 750, 800, 850 or 900 Da. In an embodiment, the LMW-DOM contains a compound that is 3-methyldioxyindole, bellendine, linoleoyl, gluconapin, N-acetylleucyl-leucyl-methionianal, aminopentol, momordicilin, sulfanilamide, dihydroxypentatriaconta-2,4-dienoic acid, an oligo peptide (e.g. Ala-Thr-Leu-His; L-leucyl-L-asparaginylglycyl-L-lysyl-L-alanyl-L-leucyl-L-valyl-L-glutamic acid; L-leucyl-L-asparaginylglycyl-L-lysyl-L-alanyl-L-leucyl-L-valyl-L-glutamic acid; and/or L-valyl-L-asparaginyl-L-isoleucyl-L-glutam inyl-L-lysyl-L-α-glutam yl-L-isoleucine), 2-hydroxyheptanoic acid, (E)-penta-1,3-dien-2-ol, a diglyceride, glycerol triaprylate, 5,7,3',4'-tetrahydroxy-3,6,5'-trimethoxyflavone, 9-octadecenoic acid, 1,2,3,4-tetrakis-o-(4-nitrobenzoyl)pentopyranose, ceramide, cefsulodin monobactam, 2,7,9-tricarboxypyrrolo(2,3-f)quinoline-4-ol-5-one, tetradecane-1,1-(O-alpha-D-glucopyranosyl)-3-keto-(1,25R,27R)-octacosanetriol, 2,4-bis[4,5-bis(pentylam ino)isoquinolin-1-yl]cyclobutane-1,3-dione, bacteriohopanetetrol cyclitol ether, azaspiracid-3, brunsvicamide A, siderochelin A, benarthin, chrysobactin, dihydroxybenzoic acid, rhizobactin, schizokinen, desferrioxamine, cyclic trichrisobactin, carboxymycobactin, exochelin, vibrioferrin, acinetoferrin, ferrioxamine or mixtures thereof. In an embodiment, the LMW-DOM contains a compound that is siderochelin A, benarthin, chrysobactin, dihydroxybenzoic acid, rhizobactin, schizokinen, desferrioxamine, cyclic trichrisobactin, carboxymycobactin, exochelin, vibrioferrin, acinetoferrin, ferrioxamine or mixtures thereof. In some embodiments, the solid form of the compound is a hydrate form thereof. It will be appreciated by a person skilled in the art that the identity of the compounds in the DOM may depend, for example, on the source of (e.g. the species of a microorganism producing) the DOM and therefore the embodiments of the present application may be varied accordingly.

Alternatively, by using a high molecular weight organic compound fraction of the DOM (HMW-DOM), the resulting non-labile complexes of the metal and the HMW-DOM are less bioavailable and can be separated through methods which make use of this property. A person skilled in the art could readily select such a method with reference to the present application and in light of common general knowledge such as known methods. Accordingly, in another embodiment of the present application, the fraction of DOM is a high molecular weight organic compound fraction of the DOM (HMW-DOM). In a further embodiment, the HMW-DOM contains molecular weights ranging from 1800-3500 Da or up to 1 µm.

In another embodiment of the present application, the fraction of DOM is a medium molecular weight organic compound fraction of the DOM (MMW-DOM). In a further embodiment, the MMW-DOM contains molecular weights ranging from 900-1800 Da.

Using a technique such as the high resolution mass spectrometry (HRMS) used in the examples of the present application can provide structural information such as mass to charge ratio about DOM compounds that readily bind metal ions such as $Hg^{2+}$. Fractionation can optionally subsequently be applied, for example, to separate homologous groups of metal-ion complexing DOM fractions.

The methods of binding metal ions in water can be used for any suitable use wherein it is desired to bind a metal ion in water. For example, the methods may be used for the remediation of wastewater as well as for other water treatment and water purification applications. In an embodiment, the method is for remediation of wastewater having a metal ion to be removed and the water is wastewater. The wastewater can be any suitable wastewater. For example, the wastewater can be domestic wastewater, urban wastewater, industrial wastewater or combinations thereof. The term "industrial wastewater" includes any suitable water that contains metal ions and is waste from industry. For example, the industrial wastewater can comprise metal processing effluent or wastewater from electroplating processes. For example, wastewater stemming from the grinding of mineral and sediment can include dissolved metals such as divalent metals, for example, mercury which can be bound in the methods of the present application. Accordingly, in an embodiment, the industrial wastewater comprises effluent from a mining operation. The methods of the present application can also be used to capture a metal ion of interest from the water. For example, so that the metal ion can be converted into the metal.

In an embodiment, the complex is separated from the water. The method of separation can involve any suitable means of separation and will depend, for example, on the method by which the water is contacted with the DOM fraction. In an embodiment, the separation comprises contacting the complex with a microorganism to sequester the complex. The microorganism can be any suitable microorganism that can uptake (sequester) the complex. For example, the studies of the present application have tested the gram-negative bacteria *E. coli* but any other suitable microorganism can be used.

A person skilled in the art can select a suitable means for contacting the water with the DOM fraction in the methods of the present application.

The terms "dissolved organic matter" or DOM as used herein refer to a ubiquitous mixture of complex organic molecules that can be operationally defined as material that passes filter pores (e.g. of 1.0, 0.7, 0.45 or 0.2 µm pore sizes). DOM can include biomolecules such as lipids, peptides, proteins, amino acids, amino sugars, carbohydrates, lignin, tannins, condensed aromatics and saturated or unsaturated hydrocarbons. The composition of a particular DOM will depend, for example, on the source of the DOM. For example, any living or dead organism found in water or on land produces DOM. Such organisms include all phytoplankton, microbes and fungi. Living organisms can, for example, produce DOM as a result of metabolic waste. The decomposition of dead materials such as plants and trees (or parts thereof such as leaves) and terrestrial and aquatic organisms also produces DOM. The terms "dissolved organic matter" or "DOM" as used herein include DOM produced by all such natural sources as well as DOM or components thereof (i.e. one or more compounds found in DOM) that has been chemically synthesized. DOM from natural sources includes DOM collected from the environment as well as DOM which has been obtained from cultured organisms or parts thereof.

Accordingly, in an embodiment, the DOM is from phytoplankton. In another embodiment, the phytoplankton is a *Chlorella* sp., a *Chlamydomonas* sp., a *Euglena* sp., a diatom, a cyanobacteria, a protist or mixtures thereof. In a further embodiment, the phytoplankton is a *Euglena* sp. It is an embodiment that the phytoplankton is *Chlorella vulgaris, Chlamydomonas reinhardtii, Euglena gracilis, Euglena mutabilis, Scenedesmus obliquus, Thalassiosira* weissflogii or combinations thereof. In an embodiment, the phytoplankton is *Chlorella* (e.g. *Chlorella vulgaris*). In another embodiment, the phytoplankton is *Chlamydomonas* (e.g. *Chlamydomonas reinhardtii*). In a further embodiment, the phytoplankton is *Euglena* (e.g. *Euglena gracilis* or *Euglena mutabilis*). In another embodiment, the phytoplankton is *Scenedesmus* (e.g. *Scenedesmus obliquus*). In a further embodiment, the phytoplankton is *Thalassiosira* (e.g. *Thalassiosira weissflogii*). In another embodiment, the phytoplankton is *Euglena gracilis, Euglena mutabilis* or combinations thereof. In a further embodiment, the phytoplankton comprises, consists essentially of or consists of *Euglena gracilis*.

In another embodiment of the present application, the DOM (or the fraction thereof) is chemically synthesized. The chemically synthesized DOM can be synthesized by known methods or obtained from a commercial source.

In a further embodiment, the DOM fraction comprises, consists essentially of or consists of hydrogenated nitrogen containing compounds, wherein the hydrogen to carbon elemental ratio (H/C) of the compounds is greater than 1.65 (i.e. the cut-off for lipid and protein material). In the studies of the present disclosure, it was observed that hydrogenated DOM preferentially facilitates uptake as opposed to highly oxygenated DOM components. Accordingly, use of a DOM fraction that comprises, consists essentially of or consists of (e.g. that is enriched in) such compounds may facilitate uptake by microorganisms in embodiments wherein the separation is carried out by such a means.

In some embodiments, the DOM fraction is isolated from DOM. The DOM fraction can be isolated from DOM by any suitable means. In an embodiment, the DOM fraction is isolated from DOM by field-flow filtration, ultrafiltration or ultracentrifugation. In another embodiment, the DOM fraction is isolated from DOM by a method comprising field-flow filtration.

The DOM can optionally be produced under conditions suitable to obtain an increased percentage of one or more desired metal ion-binding compounds in the DOM fraction. For example, the conditions can comprise growing a culture of phytoplankton under conditions suitable to obtain the increased percentage of one or more desired metal ion-binding compounds in the DOM fraction. Such enhanced production can be influenced by culture conditions such as but not limited to medium, temperature, light, pH, ionic strength and metal concentrations. Accordingly, in an embodiment, the conditions comprise one or more of a desired medium, temperature, light, pH, ionic strength and metal concentration. For example, the generation of reactive oxygen species (ROS) and metabolic stress can induce an increase of antioxidants such as cysteine (Cys) and glutathione (GSH). Therefore, an increase in culturing metals, temperatures and/or light intensity or duration (within ranges tolerable to the phytoplankton) induces LMW compounds. The increase in light could also cause photodegradation of larger molecular weight compounds into smaller molecular weight compounds. Similarly, a decrease in culture pH could also cause degradation of larger molecular weight DOM compounds into smaller subunits. The exposure of phytoplankton cultures to non-lethal metal concentrations can act as a selective pressure wherein tolerant cells exhibit changes in peptide and amino acid composition and concentration. In another embodiment of the present application, the conditions comprise varying the light regime. In a further embodiment, the light regime is 16:8 h light:dark. In another embodiment of the present application, the light regime is 20:4 h light:dark.

The metal ion can be any suitable metal ion which forms a complex with the DOM fraction. The expressions "form a complex between the DOM fraction and the metal ion" and "metal ion which forms a complex with the DOM fraction" as used herein refers to forming a complex between the metal ion and at least one compound that is a component of the DOM fraction. The metal ion can be an anionic or cationic metal such as arsenic, rare earth elements, uranium and radionuclides. It will be appreciated by a person skilled in the art that the DOM fraction can include compounds with heteroatoms such as nitrogen (N), oxygen (O) and sulfur (S) that are capable of binding suitable metal ions. A DOM fraction can be selected for binding a particular metal or class thereof. For example, type A metals typically form more stable complexes with O- and N-containing ligands whereas Type-B metals typically form more stable complexes with S-containing ligands and metals are known to exhibit behaviour intermediate between Type A and Type B metals. In some embodiments, the metal is a transition metal. In some embodiments, the metal is a metal ion (i.e. $M^{2+}$) and optionally $Hg^{2+}$ or another metal that shows similar binding to heteroatoms (e.g. N, O and S) such as $Cd^{2+}$, $Zn^{2+}$, $Co^{2+}$, $Ni^{2+}$ or $Pb^{2+}$. In another embodiment, the metal ion is a rare earth element, a divalent metal, a transition metal, or a divalent transition metal. In another embodiment, the metal ion is $Hg^{2+}$. In another embodiment, of the present application, the metal ion is $Cd^{2+}$.

The present application also includes a use of a fraction of dissolved organic material for binding a metal ion in water.

It will be appreciated by a person skilled in the art that embodiments of the uses of the present disclosure can be varied as described herein for the methods of the present disclosure.

The following non-limiting examples are illustrative of the present application:

EXAMPLES

Example 1: The Role of Dissolved Organic Matter Size Fractions and Composition on Aerobic Mercury Uptake To evaluate the role that DOM molecular weight (MW) and composition have on Hg bioavailability, a multi-pronged approach was developed, which relied on the use of asymmetrical flow field-flow fractionation (AF4) to separate DOM based on molecular weight, Fourier transform ion cyclotron mass spectrometry (FT ICR-MS) for resolved compositional assessment of MW fractions, and a whole-cell biosensor to investigate how size and composition of organic ligands influence $Hg^{II}$ bioavailability under oxic conditions. Using these techniques in a multi-pronged approach, two fulvic acid reference standards from the Suwannee River (dominated by allochthonous inputs) and from Pony Lake (microbially based Antarctic aquatic ecosystem) were compared to study how DOM size fractions and composition influence $Hg^{II}$ bioavailability.

I. Materials and Methods (a) Standards and Asymmetrical Flow Field-Flow Fractionation SRFA and PLFA were obtained from International Humic Substances Society, dissolved in ultrapure water (MQW; 18 mΩ), and filtered through a 0.7 μm glass fiber filter. Whereas SRFA and PLFA were subject to a variety of purification treatments, these standards served as a suitable DOM source for initial investigations into the role of DOM MW and structure influencing Hg bioavailability and used widely as reference materials to study metal bioavailability[20]. The AF2000 Focus fractionation system (Postnova Analytics) with an on-line UV-visible spectrophotometer (Shimadzu SPD-M20A) and fraction collector (Varian ProStar 701) were used to isolate DOM size fractions. A 300 Da polyethersulfonate (PES, Postnova Analytics) with flow setting of 0.25, 2.2 and 2.45 mL min$^{-1}$ for axial, focus and cross flows, respectively. A calibration solution of macromolecular proteins was utilized to calibrate molecular weight of SRFA and PLFA[21-23]. Approximately 2 mL of 200 ppm-C SRFA and PLFA were injected into the 300 μL sample loop and fractions were collected during the elution stage at 1 min intervals. Dissolved organic carbon (DOC) concentrations of each size fraction were determined using a UV-Visible absorbance at 254 nm where a calibration curve of known SRFA and PLFA concentrations and corresponding UV-Visible absorbance values were determined. Low (LMW 300-900 Da), medium (MMW 900-1800 Da) and high MW (HMW 1800-3500 Da) molecular weight fractions were collected for further analyses. LMW and MMW fractions coincided with the peak maxima in the AF4 fractogram for both SRFA and PLFA, respectively.

(b) Bioreporter Assay

An *E. coli* whole-cell biosensor was used to evaluate $Hg^{II}$ bioavailability[24] where assay conditions were described in Chiasson-Gould et al. (2014)[25]. Cultures were obtained from a single plate colony and inoculated in 5 mL of lysogeny broth (LB) in the presence of kanamycin at 37° C. for 6-7 h until log phase. Fifty microliters of the culture were transferred to a 25 mL serum bottle containing 5 mL of glucose minimal media (GMM) and incubated overnight. In the morning, 20 mL of fresh GMM was added and the cells were incubated for 2 h with shaking. 4 mL of the culture was then centrifuged at 10,000 rpm for 90 seconds and then was resuspended in 67 mM phosphate buffer. Final cell density, measured as the optical density at 600 nm ($OD_{600}$), was set to 0.4 ($3.0 \times 10^8$ cells/mL) and 1/10 dilution was used for assays.

Figure 1:
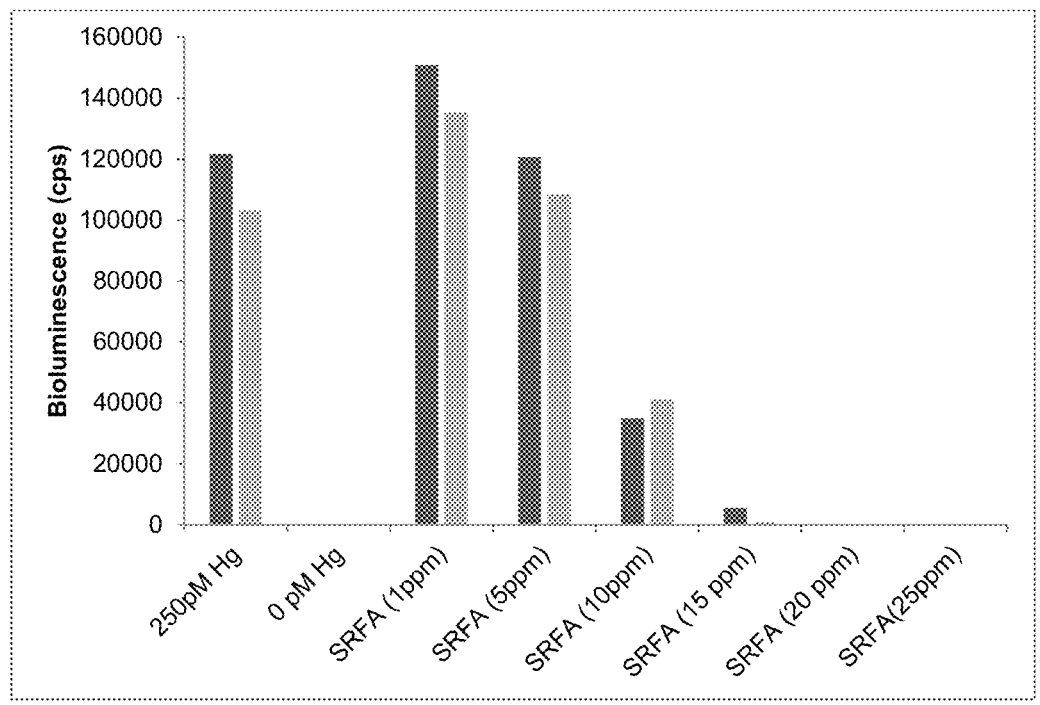
FIG. 1 is a plot showing bioassay response in bioluminescence (cps) for various embodiments of an example of the present application based on glass (dark grey) and Teflon (light grey) scintillation vials.

Assays were prepared in both Teflon and borosilicate scintillation vials (FIG. 1) filled with 1.8 mL assay medium, 200 µL cells, variable DOM concentration (final concentration: 1, 5, 10, 15 and 20 ppm-C) and a concentration of 250 pM $Hg^{II}$ supplied as $Hg(NO_3)_2$ in 0.2 M $HNO_3$. For fraction assays, similar volumes of assay media, cells and Hg were used with 1 ppm-C DOC for each fraction to minimize the influence of DOC concentration while maximizing biosensor response. Hg was allowed to equilibrate in the scintillation vials with each treatment for one hour prior to the addition of the cells. Immediately after cell addition, 200 µL of assay solutions were transferred to a 96-well Teflon plate (PFA) and bioluminescence was measured on a multimode plate reader (Tecan F200 Pro) for 4 h (every 5 min). Luminescence of negative controls (no DOM, no Hg) and positive controls (no DOM, 250 pM Hg) were conducted. A control strain (E. coli HMS174 pRB27) that continuously emits light was used to test for variations in light production that were unrelated to the presence of Hg. Two independent bacterial cultures technical triplicates were performed on all concentration regimes as well as all size fractions. Induced luminescence data (expressed as relative light units, RLU) resulting from the presence of intracellular Hg were corrected for the luminescence (RLU) produced by the control strains under the same conditions; as such, bioavailable Hg data are presented as unitless.

(c) FT ICR MS and Statistical Analyses

Ultrahigh resolution mass spectra were obtained using a 7T Bruker SolariX XR FT ICR-MS (Billerica, Mass.) equipped with an electrospray ionization (ESI) ion source and a ParaCell ion cyclotron resonance (ICR) cell. SRFA and PLFA bulk samples and fractions were diluted to 1 ppm-C at pH 2. A methanol to water/sample ratio (40:60) was injected in the FT ICR-MS for blanks and samples, respectively. FT ICR-MS was externally calibrated with a NaTFA tuning mix (Thermo Scientific) prior to sample injection, and internally calibrated with three lock masses (i.e. 248.9603, 656.8848 and 928.8344 m/z). Samples were run in negative ESI with a capillary voltage of 4500V, continuous injection rate of 120 µL/h, and a 2 s ion accumulation time to accumulate 200 scans in adsorption mode[26].

Peak assignments were analyzed using Bruker Compass DataAnalysis (v4.2) where elemental constraints for formula assignment were: $^{12}C$ (0-50), $^1H$ (0-100), $^{16}O$ (0-30), $^{14}N$ (0-2), $^{32}S$ (0-2), $^{13}C$ (0-1)[27-26], and an error tolerance of ±2 ppm was used. Elemental formulas were exported and an in house Matlab (7.10) script was utilized for van Krevelen diagrams synthesis and percent composition calculations[29]. Aromaticity index (AI) was calculated based on Koch and Dittmar, 2006[30] to determine the average aromaticity of the sample compound[31] (Equation 1).

$$AI = \frac{1 + C - O - S - 0.5H}{C - O - S - N} \quad \text{(Equation 1)}$$

Analysis of variance (ANOVA) tests were conducted in Excel 2011 to test for significance based on biological duplicates. Principal component analyses (PCA) were generated in R (3.22) using the FactoMineR package and multivariable statistics from the software PAST (2.17)[31] to examine relationships between fraction corn positions.

II. Results and Discussion (a) Effect of DOC Concentration on Hg Bioavailability $Hg^{II}$ bioavailability was first tested in the presence of a bulk fraction of SRFA (FIG. 2) and PLFA (FIG. 3) at concentrations ranging from 1 to 20 ppm-C. $Hg^{II}$ uptake increased significantly in the presence of 1 ppm-C SRFA when compared to the DOM-free sample (one-way AVONA, p<0.05) but decreased at [DOC]>5 ppm. In the presence of PLFA, $Hg^{II}$ bioavailability decreased from 1 ppm-C to 20 ppm-C. These data are in line with what was previously observed under equilibrium conditions for which DOM concentration affects Hg uptake[25,32].

(b) Influence of Molecular Weight of DOM on Hg Bioavailability

Figure 2:
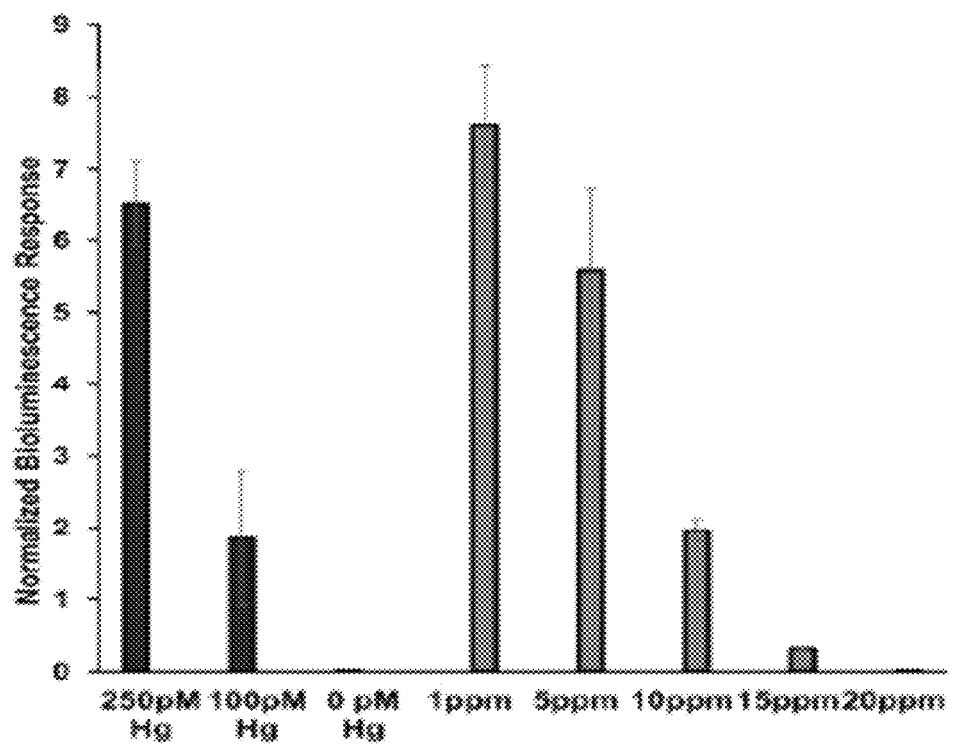
FIG. 2 is a plot showing normalized bioluminescence response from 1-20 ppm dissolved organic carbon (DOC) for Suwannee River (SRFA) samples. The first through third bars from the left indicate 250 pM, 100 pM and 0 pM, respectively of $HgNO_3$ added in the absence of ligands.
Figure 3:
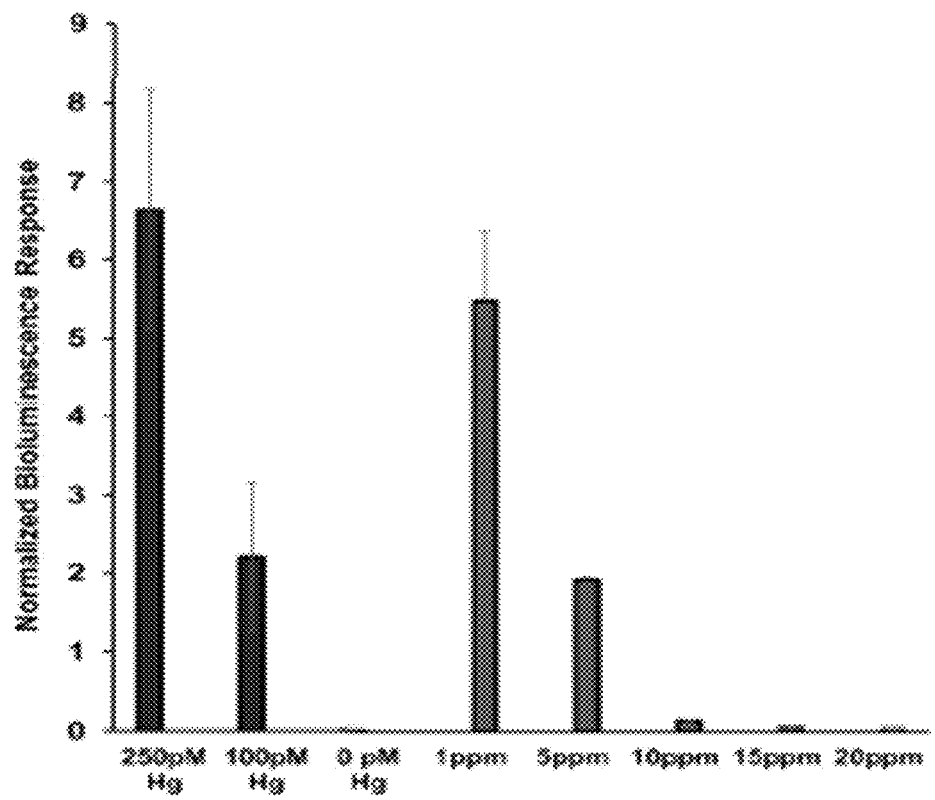
FIG. 3 is a plot showing normalized bioluminescence response from 1-20 ppm DOC for Pony Lake (PLFA) samples. The first through third bars from the left indicate 250 pM, 100 pM and 0 pM, respectively of $HgNO_3$ added in the absence of ligands.
Figure 4:
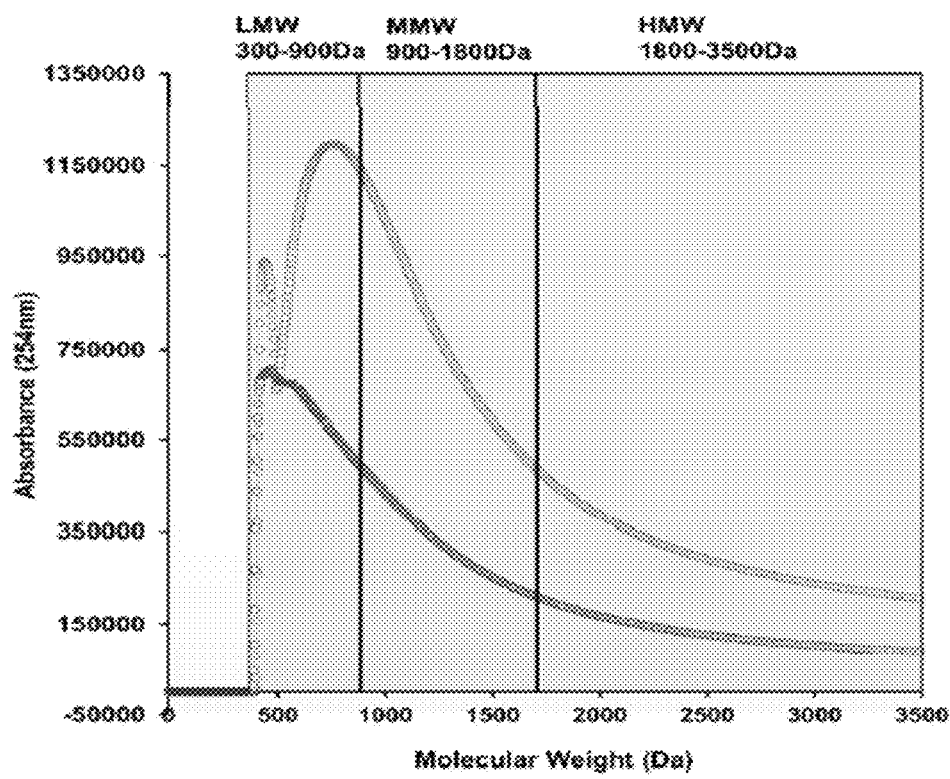
FIG. 4 shows an asymmetrical flow field-flow fractionation (AF4) fractogram at 254 nm of SRFA (light grey) and PLFA (darker grey) with vertical bars indicating the boundaries between low molecular weight (LMW; 300-900 Da); medium molecular weight (MMW; 900-1800 Da) and high molecular weight (HMW; 1800-3500 Da) fractions.
Figure 5:
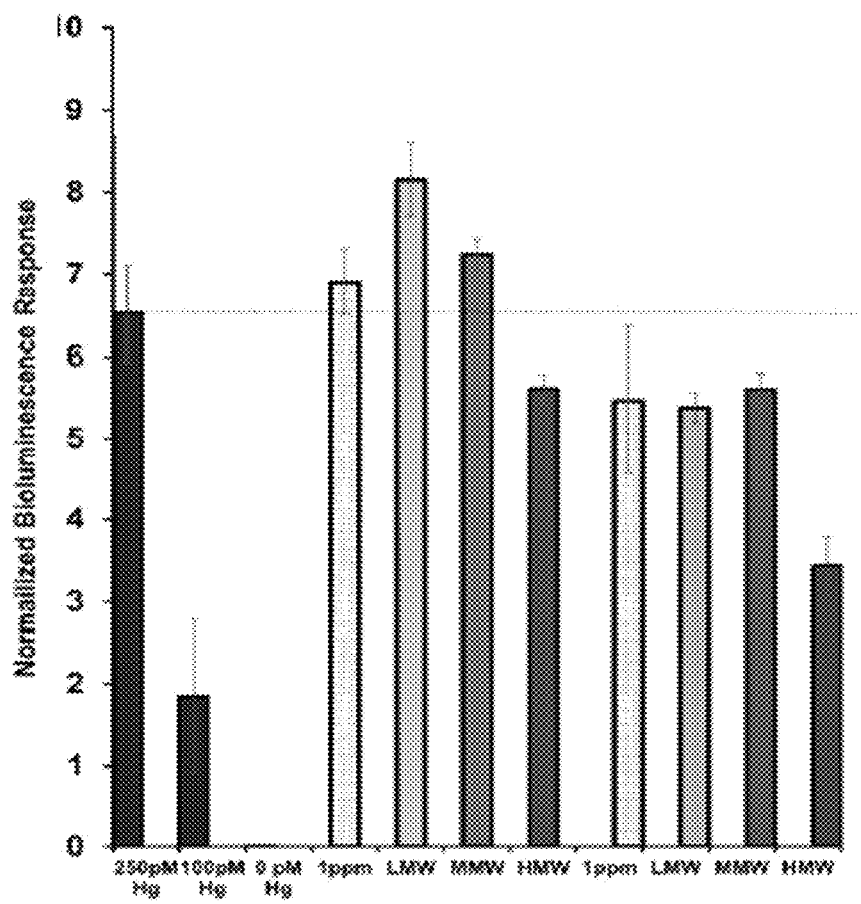
FIG. 5 is a plot showing the response of the fractions in FIG. 4 to 250 pM of $HgNO_3$ (fifth to seventh bars from the left; SRFA and ninth to eleventh bars from the left; PLFA) in comparison to the bioassay response to 1 ppm unfractionated SRFA and PLFA (fourth and eighth bars from the left, respectively). The first through third bars from the left indicate 250 pM, 100 pM and 0 pM, respectively of $HgNO_3$ added in the absence of ligands.
Figure 6:
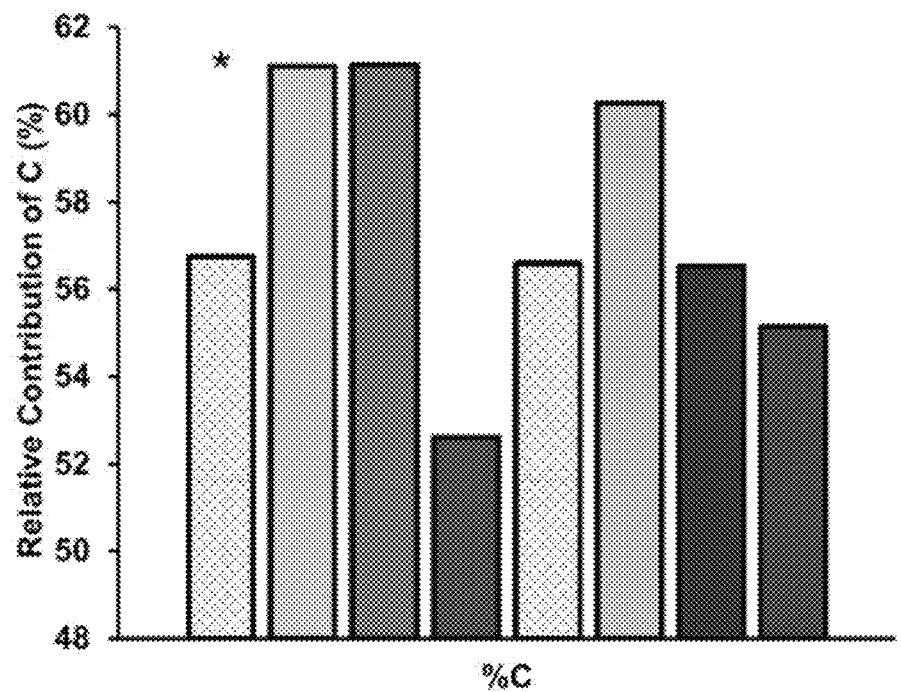
FIG. 6 shows Fourier-transform ion cyclotron resonance mass spectrometry (FT ICR-MS) weighted elemental contribution within bulk (dotted) and AF4 size fractions of SRFA (left four bars) and PLFA (right four bars) for carbon. Asterisk represents a significant difference (p<0.05) in composition between LMW and HMW fractions for both SRFA and PLFA.
Figure 7:
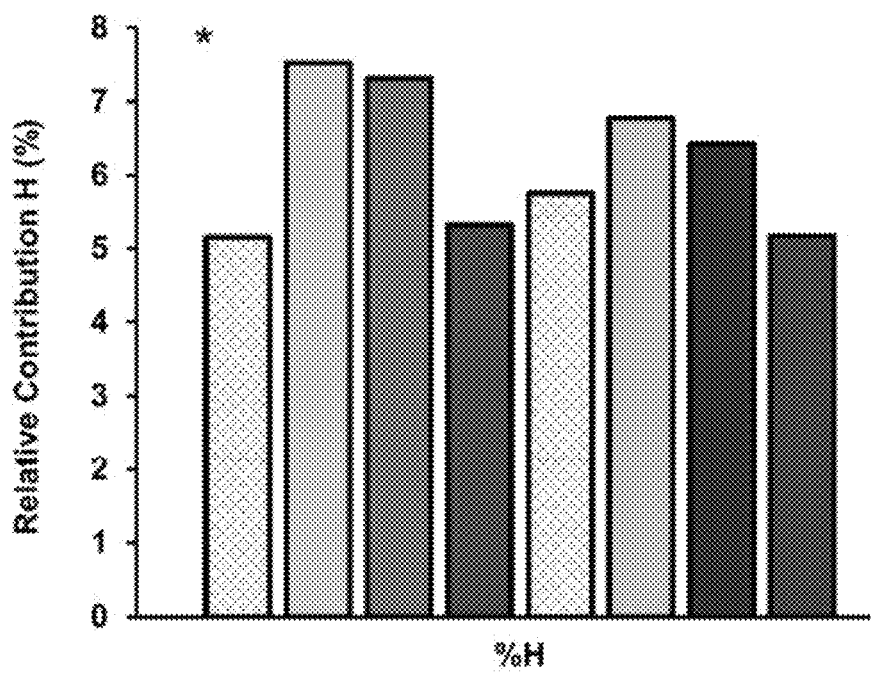
FIG. 7 shows FT ICR-MS weighted elemental contribution within bulk (dotted) and AF4 size fractions of SRFA (left four bars) and PLFA (right four bars) for hydrogen.

The AF4 fractogram revealed a peak maximum at UV 254 nm in the LMW fraction for both SRFA and PLFA (FIG. 4), followed by a decrease in UV response as size ranges increased (FIG. 2). $Hg^{II}$ uptake increased 18.1% and 4.95% in the presence of LMW and MMW from SRFA, respectively (FIG. 5); all PLFA fractions inhibited $Hg^{II}$ uptake, suggesting, while not wishing to be limited by theory, that compounds likely to facilitate Hg uptake are present in SRFA LMW and MMW but absent in PLFA (FIG. 2). In all cases, the HMW fraction was most effective at decreasing $Hg^{II}$ bioavailability leading to a significant (p<0.05 one-way ANOVA) reduction of 18.6% and 37.1% in bioavailable $Hg^{II}$ for SRFA and PLFA when compared to LMW fractions.

(c) Compositional Differences of DOM fractions

The increase in $Hg^{II}$ uptake in the presence of SRFA LMW and MMW fractions, while not wishing to be limited by theory, may be due to the greater H content and lower O content of SRFA compared to the PLFA LMW and MMW fractions (FIGS. 6-11; Tables 1 and 2; FIG. 12). These results suggest, while not wishing to be limited by theory, that hydrogenated DOM preferentially facilitates uptake as opposed to highly oxygenated DOM components[33]. Furthermore, the aromaticity index (AI) for LMW and MMW SRFA fractions was lower than for LMW PLFA fractions (FIG. 11). This inverse relationship between AI and bioavailability was observed for both SRFA ($r^2=0.97$) and PLFA ($r^2=0.99$), suggesting that AI may be a useful predictive tool for $Hg^{II}$ bioavailability (FIG. 11)[2,34]. Increasing AI in HMW fractions suggests an increased presence of aromatic phenyl functional groups that are highly polarizable ligands involved in Hg binding[35]. HMW fractions also had significantly lower C content (p<0.05), H content (p<0.05), higher O content (p<0.01) and largest AI values (p<0.05) indicative of more oxygenated, aromatic DOM than LMW and MMW fractions for both SRFA and PLFA. No significant difference in N and S content was observed within SRFA and PLFA samples (p>0.05; FIGS. 9-10), suggesting, while not wishing to be limited by theory, differences in $Hg^{II}$ bioavailability were not solely driven by N and S content but also by MW and aromaticity characteristics.

Table 1 shows SRFA average atomic ratios and weighted percentage composition for size fractions and unfractionated bulk material based on FT ICR-MS. Table 2 shows PLFA average atomic ratios and weighted percentage composition for size fractions and unfractionated bulk material based on FT ICR-MS. LMW fraction for both SRFA and PLFA have significantly (p<0.05) different % C, % H, and % O compositions than HMW fractions.

TABLE 1

SRFA average atomic ratios and weighted percentage composition.

| | LMW | MMW | HMW | Bulk |
|---|---|---|---|---|
| O/C | 0.400647 | 0.596396 | 0.641104 | 0.427424 |
| H/C | 1.459999 | 1.375874 | 1.215925 | 1.183298 |
| N/C | 0.034593 | 0.055732 | 0.079141 | 0.022384 |
| S/C | 0.031918 | 0.053885 | 0.111108 | 0.013898 |
| % C | 61.11187 | 61.13751 | 52.61252 | 56.73032 |
| % H | 7.529443 | 7.314263 | 5.318466 | 5.155639 |
| % O | 25.05265 | 24.26459 | 34.33336 | 34.63011 |
| % N | 1.928881 | 2.185305 | 2.247054 | 1.906295 |
| % S | 4.396346 | 5.119319 | 5.513155 | 2.160173 |
| AI | −0.04537 | 0.093152 | 0.243362 | 0.095427 |

TABLE 2

PLFA average atomic ratios and weighted percentage composition.

| | LMW | MMW | HMW | Bulk |
|---|---|---|---|---|
| O/C | 0.458838 | 0.644221 | 0.746329 | 0.477634 |
| H/C | 1.311547 | 1.268617 | 1.12748 | 1.242199 |
| N/C | 0.063807 | 0.027545 | 0.037222 | 0.029395 |
| S/C | 0.032973 | 0.039495 | 0.040227 | 0.038781 |
| % C | 60.27021 | 56.5063 | 55.12842 | 56.58204 |
| % H | 6.781622 | 6.428213 | 5.172363 | 5.756577 |
| % O | 25.89777 | 31.02867 | 33.14295 | 31.22263 |
| % N | 2.629135 | 1.672934 | 1.976618 | 1.879492 |
| % S | 4.440544 | 4.384524 | 4.601309 | 5.488923 |
| AI | 0.132058 | 0.035148 | 0.554714 | 0.016656 |

(d) Composition, Size and Hg (II) Bioavailability

To examine the relationships between fraction and compositional differences, principal component analysis (PCA) of percent composition and AI were conducted (FIG. 13). Principal component 1 (PC1) explained 52.6% of the overall variance with negative values indicative of aliphatic material and positive values of enhanced aromatic character whereas principal component 2 (PC2) explained 31.5% of the variance with correlations to N/C and S/C ratios. High H/C ratios indicative of aliphatic material[9] contributed to the LMW fractions of both SRFA (H/C=1.46) and PLFA (H/C=1.31). While larger MW fractions correlate to AI, these contributions cannot be delineated as they are intrinsically related[36].

PLFA fractions displayed a significant (p<0.05) increase in AI from LMW fractions to HMW fractions; however, no change in S content was observed. PC1 eigenvalues showed a strong negative relationship to $Hg^{II}$ bioavailability for both SRFA and PLFA ($r^2$=0.85 and 0.94, respectively) (FIG. 14) suggesting, while not wishing to be limited by theory, a linear relationship between increasing AI and decreasing $Hg^{II}$ bioavailability.

Previous studies have shown that DOM with higher O/C ratios was less bioavailable to microorganisms than DOM exhibiting higher H/C ratios[9]. Together with this new data, this suggests, while not wishing to be limited by theory that $Hg^{II}$ uptake can also be an active process coupled to the use of DOM components as a nutrient source. Furthermore, laboratory studies have shown that LMW S-containing amino acids such as cysteine favor Hg uptake over larger sulfur-containing peptides (e.g. glutathione, GSH)[37]. Similarly, field experiments[3,38] suggested that $Hg^{II}$ bioavailability is favored in the presence of small protein-like LMW substances[2-3, 37-38]. In contrast, larger molecular weight fractions favor $Hg^{II}$ stabilization through polydendate interactions and steric shielding of the complex reducing $Hg^{II}$ bioavailability[7,36-40].

Studies investigating the role of DOM on $Hg^{II}$ bioavailability have revealed the complexity of DOM where organic ligands can both enhance and inhibit Hg Uptake[2,7,25,32]. This duality has also been linked to DOM source and composition. For instance, marine DOM rich in microbial processed material increased Hg bioavailability compared to larger, aromatic terrestrial DOM[39]. Terrestrial DOM undergoes photochemical and microbial transformations leading to the hydrolysis of large molecules into smaller, hydrogenated fragments and ultimately enhancing microbial carbon consumption[17,41]. The increased uptake of $Hg^{II}$ in the presence of LMW and MMW SRFA suggests, while not wishing to be limited by theory, that the active uptake of $Hg^{II}$ is facilitated by the presence of smaller hydrogenated compounds such as monomeric amino acids and carbohydrates[42-43].

Aerobic $Hg^{II}$ uptake may, while not wishing to be limited by theory, represent a missing piece in the understanding of how Hg is transferred from the atmosphere to anoxic zones. The present data show that upon $Hg^{II}$ deposition, $Hg^{II}$ bioavailability is enhanced due to its binding to small, hydrogenated biologically labile DOM. Accordingly, while not wishing to be limited by theory, a bioavailable pool of $Hg^{II}$ may temporary be stored in aerobic microbial biomass before settling to anoxic environment where it can be delivered to methylation sites. This temporary storage of $Hg^{II}$ in microbial biomass may limit its interaction with large DOM components that may otherwise limit its transfer to (micro) biota. The present study underscores the need to characterize DOM at a molecular level to evaluate its role on Hg bioavailability; and shows that a multi-pronged approach combining state-of-the-art analytical and microbiology approaches is useful to the study of Hg transformations and key biogeochemical processes.

Example 2: Detection of Mercury-Dissolved Organic Matter Complexes Using High Resolution Mass Spectrometry Mercury is a toxic metal that has the potential to disrupt natural enzymatic processes and causes cellular stress in its inorganic form ($Hg^{II}$). Recent anthropomorphic processes have led to increased mercury concentrations in aquatic systems and have prompted further investigation to the current understanding of Hg speciation. Upon $Hg^{II}$ deposition from the atmosphere into aquatic systems, immediate interactions with complex dissolved organic matter (DOM) produced by phytoplankton influence the complexation, mobility and bioavailability of resulting complex[25]. DOM is a ubiquitous mixture of complex organic molecules that can be operationally defined as material <0.45 µm. Understanding the interactions between Hg and DOM in freshwater environments is useful for understanding mobility and toxicity to aquatic biota. The present study relates to the use of Orbitrap mass spectrometry to detect Hg phytoplankton DOM complexes. While a few known studies have previously utilized HRMS to examine Hg interactions with known ligands, this is the first study that examines Hg-DOM interactions using HRMS. The premise of conducting HRMS on bulk phytoplankton DOM and studying Hg interactions was to validate the fractionation method.

I. Materials and Methods

High resolution mass spectrometry (HRMS) has allowed for the accurate characterization of complex heterogeneous mixtures. The present study utilized HRMS to examine DOM produced by phytoplankton in freshwater settings and how it interacts with environmentally relevant concentrations of Hg (II). By identifying common Hg isotopic shifts, Hg peaks can be identified and corresponding organic ligands and functional groups bound to Hg can be simultaneously identified. Phytoplankton DOM from *Chlamydomonas reinhardtii*, *Chlorella vulgaris* and *Euglena gracilis* was obtained by filtering cultures through a 0.2 µm filter. L-Cysteine (ThermoScientific) was utilized at a 2:1 molar ratio to Hg to detect Hg in the presence of known bound ligands.

$2.5 \times 10^{-6}$ M of Hg was added to DOM samples, and diluted with ultrapure MeOH (50:50). The resulting solution was brought to pH 6.8 with NaOH and injected into an Orbitrap Q-Exactive (ThermoFisher) at an injection volume of 50 µl/min and a minimum of 200 scans were acquired in ESI positive mode. Molecular formulas were assigned for peaks with a mass accuracy window ≤2 ppm. Elemental constrains for formula assignment were $^{12}C$ (0-50), $^{1}H$ (0-100), $^{16}O$ (0-30), $^{14}N$ (0-2), $^{32}S$ (0-2), $^{13}C$ (0-1), $^{202}Hg$ (0-1) using the odd nitrogen rule[44]. Thermo Qualbrowser (Xcalibur 3.0.63) isotope simulation was utilized to reinforce isotopic patterns for observed compounds and their theoretical isotopic shifts. To further reinforce observed isotopic patterns, the computer program "Winnow" was used to detect isotopic patterns of specific Hg containing compounds[45].

II. Results and Discussion (a) Mercury-Cysteine Interactions

As can be seen from the results presented in FIG. 15, in a 2:1 molar solution of cysteine and Hg, Hg(Cys)$_2$ complexes were detected (top) and were comparable to the theoretical isotopic distribution (bottom) with a 94% similarity in a 50:50 MeOH to water matrix.

(b) Phytoplankton-Derived DOM

FIG. 16 shows results relating to phytoplankton derived DOM from *Chlorella* (left), *Chlamydomonas* (middle) and *Euglena* (right) in the absence of Hg. Spectra are a normal distribution with $CH_2$ Kendrick mass shifts. Weighted average m/z of phytoplankton DOM are 394, 267 and 298, respectively. Inner van Krevelen plots show relatively larger contributions of lipid material in *Chlorella*, unsaturated hydrocarbons in *Chlamydomonas*, and proteins produced by *Euglena*[44,28]. This was based on O/C and H/C ratios depicted by van Krevelen diagrams. The abundance of low molecular weight material (<900 Da) present in phytoplankton-derived DOM suggests, while not wishing to be limited by theory, highly labile compounds being produced. At environmentally relevant concentrations and ratios of DOM to Hg, a large proportion of Hg was found bound to nitrogen and sulfur containing heteroatoms in phytoplankton DOM. Examining Hg-DOM interactions and both equilibrium and pseudo-equilibrium conditions displayed an overall change in Hg location. Understanding the interactions with phytoplankton-derived DOM upon immediate atmospheric deposition of Hg can aid, for example, in predicting Hg mobility and bioavailability in freshwater systems.

(c) Phytoplankton-Derived DOM Hg Complexes

FIG. 17 shows spectra depicting measured complexes (top) and a comparison to the theoretical isotopic distribution below. For observed spectra, a ±5 ppm difference in observed vs predicted m/z was found. The deconvolution of the peak by Winnow further reinforced the presence of 7 isotopic patterns of Hg. For example, a complex with the formula $C_{37}H_{66}OHg$ (from *Chlorella*) had a 72% similarity, a complex with the formula $C_{38}H_{62}ONHgS_2$ (from *Chlamydomonas*) had a 69% similarity and a complex with the formula $C_4H_{11}O_4HgS_2$ (from *Euglena*) had a 62% similarity with the theoretical isotopic distribution.

(d) Hg Bioavailability and Significance

FIG. 18 shows mass spectra and boxes associated with detected organic ligands found complexed to Hg, namely $C_{37}H_{66}OHg$ (from *Chlorella*; left), $C_{38}H_{62}ONHgS_2$ (from *Chlamydomonas*; middle) and $C_4H_{11}O_4HgS_2$ (from *Euglena*; right). Other studies can examine how differences in DOM sources may influence Hg uptake and bioavailability (see, e.g. Example 1). Based on comparison to structures in ChemSpider, proposed structures for these formulae are, shown, respectively, in Scheme 1:

Scheme 1

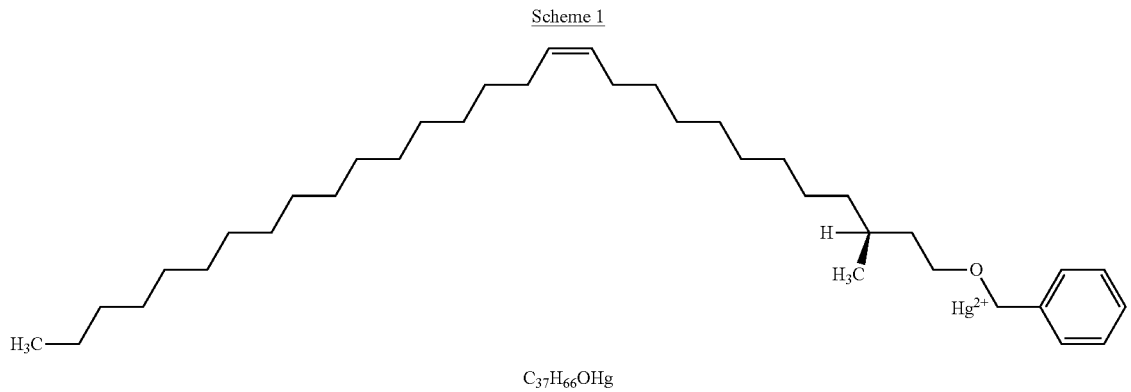

$C_{37}H_{66}OHg$

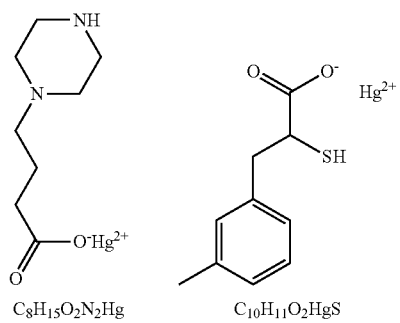

$C_8H_{15}O_2N_2Hg$  $C_{10}H_{11}O_2HgS$

III. Summary

High resolution mass spectrometry can be utilized to identify organic ligands bound to Hg. Based on bioassays results, size of DOM is an important variable when determining variability. Therefore, the relative abundance and m/z of the HRMS Hg—DOM complexes detected can be used to predict the bioavailability. The subsequent fractionation of the Hg-DOM complexes can be facilitated. While previous methods provide minimal speciation information, the present methods can provide elemental and structural information of organic ligands produced by phytoplankton for Hg binding.

Example 3: Fractionated LMW Compounds for Mobilization of Mercury

Asymmetrical flow field-flow fractionation (AF4) was used to separate dissolved organic matter from Suwannee River Fulvic Acid (SRFA), *Chlorella vulgaris*, *Chlamydomonas reinhardtii*, and *Euglena gracilis* into three separate fractions based molecular weights (FIG. 19). Low molecular weight (LMW: 300-900 Da), medium molecular weight (MMW: 900-1800 Da) and high molecular weight (HMW: 1800-3500 Da) fractions were collected and exposed to 250 pM of $Hg(NO_3)_2$. Bar graph results are shown in (FIG. 20). These findings show, for example, fractionated LMW organic compounds may be utilized for controlling the mobilization of mercury in contaminated bodies of water.

Example 4: Identification of Mercury-Binding LMW Compounds: Molecular Interactions Between Phytoplankton Based DOM and Mercury Revealed by High Resolution Mass Spectrometry The composition of phytoplankton DOM and its interactions with Hg are fundamental steps to understand how inorganic Hg is internalized by methylating organisms. High resolution mass spectrometry (HRMS) has been used to provide compound level information for international humic society standard (IHSS) standards, algae and DOM. The objectives of this work are, for example, to: (1) assess phytoplankton DOM-Hg interactions using HRMS and (2) investigate structural properties of Hg binding DOM during different light cycles. The sensitivity and resolution of Orbitrap mass spectrometry allows for the detection of DOM-Hg complexes.

I. Materials and Methods
(a) Algal Growth and DOC Concentrations

*Euglena gracilis* Klebs were obtained from Boreal Laboratory Supplies Ltd (St. Catharines, ON, Canada). *Euglena gracilis* was grown under 16:8 h light to dark cycle using bold basal media (BBM) at pH 5.65. Cells were harvested at approximately $1.0 \times 10^6$ cells/mL for DOM analyses. Laboratory grown cultures of *Chlamydomonas reinhardtii*, *Chlorella vulgaris* and *Scenedesmus obliquus* were obtained from the Canadian Phycological Culture Center (CPCC) in Waterloo, Ontario and grown using a high salt media (HSM) for *Chlamydomonas* and a BBM for *Chlorella* and *Scenedesmus*. Growth conditions included photoperiods of standard and high light regimes (16:8 h and 20:4 h light to dark, respectively) at a fixed light intensity of 90-100 μmol photons $m^{-1}$ $s^{-1}$ and a fixed temperature of 21° C. Cultures were harvested at mid exponential growth phase where the cell density was $1 \times 10^6$ cells/mL and filtered through a pre-combusted 0.7 μm glass fiber filter (GF/F Whatman) into acid washed and pre-combusted glassware. Biological duplicates of phytoplankton-derived DOM were collected at both light regimes. Filtered phytoplankton-derived DOC concentrations were measured using a total organic carbon (TOC) analyzer and fixed to 1 mg C. $L^{-1}$ for further analyses (Table 3).

TABLE 3

DOC Concentrations (mg/L) for *Chlorella*, *Chlamdyomonas* and *Scenedesmus* exudates at different light regime growth conditions of 16:8 h and 20:4 h (light:dark; n = 2).

|  | 16:8 h | 20:4 h |
| --- | --- | --- |
| *Chlorella* | 7.3 ± 1.2 | 9.6 ± 0.9 |
| *Chlamydomonas* | 6.1 ± 0.8 | 10.3 ± 1.5 |
| *Scenedesmus* | 3.7 ± 0.4 | 5.2 ± 0.6 |

(b) qBBr Titration

Fresh stock solution of 0.001 M qBBr (SigmaAldrich) was prepared daily in an amber glass bottle covered in aluminum foil. A series of qBBr standard addition solutions was prepared by mixing 5 mL of DOM samples with different volumes of qBBr (0, 25, 50, 100, 250, 400, 500, 600, 750, 900 μL), resulting in corresponding final qBBR concentrations of 0, 4.98, 9.90. 19.61, 47.62, 74.07, 90.91, 107.14, 130.43, 152.54 μM. Mixtures were covered with aluminum foil and mixed for an hour at room temperature. qBBr-equivalent thiol concentration was determined with this standard addition using a Fluoromax4 spectrophotometer (Horiba Jobin Yvon) equipped with a 1 cm quartz cuvette. The excitation wavelength of 380 nm was used and the sample emission was monitored from 400 to 500 nm. Maximum emission at 470 nm ($A_{470}$) was measured after correcting for qBBr emission background. To obtain background fluorescence of qBBr solution, a series of solutions were examined similarly, with milliQ in place of DOM samples. As the qBBr tag binds to thiols in a 1:1 molar ratio, the level of qBBr saturation in samples corresponded to thiol concentration. Total thiol concentration was determined using non-linear piece-wise regression (SigmaPlot, v10) ($0.97<R^2<0.99$; $p<0.05$)[21].

(c) High Resolution Mass Spectrometry

The molecular composition of phytoplankton-derived DOM was determined using the Orbitrap Q Exactive (Thermo Fisher Scientific, Bremen, Germany) equipped with a heated electrospray ionization (HESI) source. Prior to injection, samples were diluted to a 50:50 sample to MeOH ratio with ultrapure MeOH (99.9% HPLC grade; Sigma Aldrich) and the pH adjusted to 6.8 with ultrapure NaOH (Sigma Aldrich). Positive ionization mode $[M+H]^+$ was utilized and samples were injected at a consistent flow rate of 50 µL/minute with an electrospray needle voltage of 4 kV and a heated capillary temperature of 300° C. Positive ionization for ESI was utilized as no Hg containing compounds were detected in negative mode by Chen et al., 2017 when using high resolution mass spectrometry while positive ESI has been utilized when examining bacterial derived DOM[53]. A resolving power of 140,000 (full width half maximum @ m/z 200) was found and sodium trifluoroacetate (NaTFA, Sigma-Aldrich 98%) was added as an internal standard in each sample to ensure exact mass accuracy between a mass range of 200-1000 m/z. Samples were acquired for a minimum of 5 minutes to allow for 200 scans to be co-added in the data post analysis stage of the Thermo Xcalibur Qual Browser (3.0.63) software. Background subtractions were conducted for phytoplankton growth media and MeOH: ultrapure mixtures prior to formula assignment. Elemental constraints for formula assignment were: $^{12}C$ (0-50), $^{1}H$ (0-100), $^{16}O$ (0-30), $^{14}N$ (0-2), $^{32}S$ (0-2), $^{13}C$ (0-1), $^{34}S$ (0-1) and $^{23}Na$ (0-1) using the odd nitrogen rule. Molecular formulas were validated based on homologous series Kendrick mass defect shifts ($CH_2$), carbon and sulfur isotopes ($^{13}C$ and $^{34}S$) to formulas where the signal to noise ratio was ≥4 within ±2 ppm exact mass error (FIGS. 21 and 22, respectively)[28, 49]. Molecular formulae with a modified aromaticity index ($AI_{mod}$) >0.67 were omitted from further analyses[30]. A MatLab script was used to determine the number of high resolution mass spectrometry compound classes based on van Krevelen diagrams. Briefly, lipid material can be found ($0.01 \leq O/C \leq 0.1$; $1.5 \leq H/C \leq 2.0$), unsaturated hydrocarbons ($0.01 \leq O/C \leq 0.1$; $0.75 \leq H/C \leq 1.5$), condensed aromatic structures ($0.01 \leq O/C \leq 0.65$; $0.25 \leq H/C \leq 0.75$), protein ($0.1 \leq O/C \leq 0.65$; $1.5 \leq H/C \leq 2.3$; $N \geq 1$), lignin ($0.1 \leq O/C \leq 0.65$; $0.75 \leq H/C \leq 1.5$) with no heteroatoms (only CHO), tannins ($0.65 \leq O/C \leq 0.85$); ($0.75 \leq H/C \leq 1.5$) and carbohydrate ($0.65 \leq O/C \leq 1.0$; $1.5 \leq H/C \leq 2.5$)[28,29,49]. Intensity weighted averages of $O/C_{wa}$, $H/C_{wa}$, $S/C_{wa}$, $\%C_{wa}$, $\%H_{wa}$, $\%O_{wa}$, $\%N_{wa}$, $\%S_{wa}$, $m/z_{wa}$, modified aromaticity index ($AI_{mod}$) and the nominal oxidation state of carbon (NOSC) were also calculated for phytoplankton derived DOM at both light regimes[50-52].

(d) Mercury Detection

Hg solutions were prepared by mixing $2.5 \times 10^{-6}$ mol $L^{-1}$ of Hg ($NO_3$) (AAS grade) and 1 ppm of organic ligand (i.e. phytoplankton DOM or L-Cysteine) and kept in the dark for at least 24 h prior to analysis. A comparable Hg concentration was utilized in a previous study examining Hg-sulfur interactions using Orbitrap mass spectrometry[47]. The pH solution was fixed to pH 6.8 with ultrapure NaOH. After the addition of Hg to L-Cysteine (SigmaAldrich) or DOM, samples were analyzed on the Orbitrap mass spectrometer after 24 hours of contact time. To detect Hg containing compounds, $^{202}Hg$ and $^{200}Hg$ isotopes were added to the elemental constraints for formula assignment, similar to previous ESI high resolution mass spectrometry Hg studies[46]. The software Winnow[45] was used to detect 7 isotopologues of Hg ($^{196}Hg$, $^{198}Hg$, $^{200}Hg$, $^{201}Hg$, $^{202}Hg$ and $^{204}Hg$). Only the peaks with a Winnow score of greater than 70% were validated based on $^{202}Hg$ and $^{200}Hg$ natural Hg isotope abundances to confidently identify Hg containing DOM compounds using Xcalibur Isotope simulation (3.0.63). To compare structural differences between Hg binding DOM, a two-way hierarchal cluster analyses and non-parametric Spearman's correlations were conducted based on weighted averages of O/C, H/C, N/C, S/C atomic ratios, elemental percentage compositions for % C, % H, % N, % O, % S and $AI_{mod}$, NOSC and m/z at 16:8 h and 20:4 h cycles using JMP (version 11). Clusters were based on Bray-Curtis similarity measure at a 95% confidence interval. A one-way analysis of variance (ANOVA) was also conducted for biological duplicates to compare weighted averages, changes in m/z distribution and compounds class differences.

(e) Putative Molecule Identification

In order to identify putative ligand-Hg complexes, organic ligands complexed to Hg were further compared to a database of known bacterial siderophores, ligands from the Kyoto Encyclopedia of Genes and Genomes (KEGG) database and Metlin Metabolite database based on m/z comparisons with an error ≤2 ppm and isotope pattern comparisons[45,54-58]. A similar approach has been conducted for metabolomics work incorporating FT ICR-MS to allow for a high-throughput detection of metabolites with a high degree of accuracy[59]. The $^{14}N$ range was increased from <3 to <7 when comparing structures to databases to allow for the potential exact mass identifications of siderophores and ligands. The structure of these compounds may, for example, be confirmed by conducting tandem MS/MS analyses. Theoretical isotopic distributions of these putative isomers were examined to allow for both exact mass and isotopic confirmation of Hg-binding compounds.

II. Results and Discussion (a) Changes in DOM Composition with Increased Light Exposure FIGS. 23-26 show changes in DOM composition with increased light exposure from *Chlorella* in the absence (FIGS. 23 and 25) and presence (FIGS. 24 and 26) of Hg. FIGS. 27-30 show changes in DOM composition with increased light exposure from *Chlamydomonas* in the absence (FIGS. 27 and 29) and presence (FIGS. 28 and 30) of Hg. FIGS. 31-34 show changes in DOM composition with increased light exposure from *Scenedesmus* in the absence (FIGS. 31 and 33) and presence (FIGS. 32 and 34) of Hg. A total of 482-1541 mass peaks was assigned between these three taxa during the two photoperiods. The mass peaks were mainly made up of singly charged peaks (FIGS. 23-34) and $CH_2$ homologous series validated shifts (FIGS. 23-34; inner graphs). At a 16:8 h light:dark photoperiod duration, each of these three phytoplankton taxa exhibited compositional differences in produced DOM. Firstly, *Chlorella* displayed a lower average $m/z_{wa}$ than *Scenedesmus* and *Chlamydomonas* (643 vs 731 and 676; FIG. 35; second plot from right on the top row). *Chlorella* displayed larger $H/C_{wa}$, $N/C_{wa}$ and $S/C_{wa}$ when compared to other taxa suggesting while not wishing to be limited by theory the release of smaller aliphatic sulfur containing proteins (FIG. 35; 2-4 plots from the left on the top row)[60]. *Chlamydomonas* DOM had the largest % $C_w$, (70.8%), followed by *Scenedesmus* (68.7%) and *Chlorella* (67.7%) (FIG. 35; far left plot on bottom row). After increasing the photoperiod duration to 20 h, the average elemental ratios of phytoplankton DOM shifted to higher $H/C_{wa}$ and lower $AI_{mod}$ for all phytoplankton, consistent with more aliphatic, hydrogenated material being secreted (FIG. 35; second plot from left on top row and far right plot on top row, respectively). % $N_{wa}$ did not significantly change for *Chlorella* (2.89±0.08% vs 2.32±0.14%), *Scenedesmus* (2.08±0.13% vs 1.98±0.02%) and *Chlamydomonas* derived DOM (1.79±0.07% vs 1.97±0.28%) (FIG. 35; third plot from left on bottom row). The % S significantly increased for *Chlorella* (3.33±0.06% vs 3.81±0.17%) and *Chlamydomonas* (3.37±0.02% vs 4.05±0.22%) whereas no significant change in % S was found for *Scenedesmus* (3.21±0.07% vs 3.45±0.11%; ANOVA p>0.05). qBBr titrations revealed significant increases in qBBr active thiol concentrations for *Chlorella* and Chlamdyomonas, (ANOVA; p<0.05) but these trends were not observed for *Scenedesmus*, comparable to HRMS results (Table 4). $NOSC_{wa}$ values increased for all phytoplankton DOM suggesting, while not wishing to be limited by theory, a shift from nonpolar to more polar compounds as light durations increased (FIG. 35; far right plot on bottom row). Although photo-oxidative stress was not explicitly measured, a higher degree in photorespiration caused by photo-oxidative stress has, while not wishing to be limited by theory, been proposed as a mechanism of increased carbon loss in phytoplankton, congruent with the increasing DOC concentrations measured in higher light cultures (Table 3)[61].

TABLE 4 qBBr-equivalent thiol concentrations (μmol/$g_{algae}$) of phytoplankton exudates grown at different light regime growth conditions of 16:8 h and 20:4 h (light:dark, n = 2).

|  | 16:8 h | 20:4 h |
|---|---|---|
| Chlorella | 32.39 ± 0.406 | 1846 ± 594.3 |
| Chlamydomonas | 856.0 ± 168.7 | 4225 ± 1379 |
| Scenedesmus | 2201 ± 595.1 | 2127 ± 728.8 |

Van Krevelen diagrams (FIGS. 36-38) indicated that the higher light duration (bottom) impacted the compound classes of DOM excreted by phytoplankton in comparison to the standard light duration (top). Significant increases in protein (45.3%-57.5%), lipids (21.4-26.3%) and unsaturated hydrocarbons (3.85-10.1%) (ANOVA; p<0.05) compound groups were observed across all phytoplankton taxa, consistent with the abundance of amino acids, fatty acids and monosaccharides released by algae (FIG. 39)[21,60-62]. Although making up a very small proportion of compounds, the aromatic structures decreased from 0.45% to 0.06% in *Chlamydomonas* and 0.51% to 0.11% for *Scenedesmus* with increasing light exposure, while not wishing to be limited by theory, likely due to photodegradation of the π structures[63] (FIG. 39). The lipid and protein abundances increased by 14-15% in *Chlorella*, whereas only lipid DOM increased for *Scenedesmus* (17%; ANOVA p<0.05). While *Chlamydomonas, Chlorella* and *Scenedesmus* have been known to have high intracellular proteins and lipid content[64-66], the higher light duration may not have been enough to induce a significant change in the relative abundance of proteins and lipids released by *Scenedesmus*, while not wishing to be limited by theory, likely due to its high tolerance to prolonged light exposure[67]. Many sulfur containing amino acids and proteins such as cysteine and GSH have been shown to increase in concentration when marine phytoplankton are exposed to increased light[68]; however, *Scenedesmus* may be resistant to the light cycles used. *Scenedesmus* was the only organism to display a significant decrease in unsaturated hydrocarbons (10.1%-6.28%; ANOVA p<0.05) with higher light exposure (FIG. 39; third plot from left on the top row). While not wishing to be limited by theory, higher light exposures can cause the conversion of unsaturated odd chain-hydrocarbons into smaller saturated lipids in algae[69]. Carbohydrate content did significantly increase with light exposure for *Chlamydomonas* and *Scenedesmus* (p<0.05), while not wishing to be limited by theory, likely due to the degradation of phytoplankton cell walls during periods of oxidative stress induced by light (FIG. 39; third plot from the right on the top row and third plot from the right on the bottom row, respectively)[70].

Upon increasing photoperiod duration, a 51% increase in lignin (11.5%-7.61%; ANOVA p<0.05), and a 14% decrease in protein material (45.3-52.2%; ANOVA p<0.05) DOM were observed in *Chlorella* DOM exudates (FIG. 39; first and second plots from the left on the top and bottom rows, respectively); no other DOM compound class showed significant changes for *Chlorella* at higher light regimes (FIGS. 23-34 and 39). While lignin is known to provide cell wall support[71], active secretion of these compounds has been reported as a possible source of a non-vascular plant derived lignin source[72]. Proteinaceous material in the form of amino acids and larger peptides as well as cyclic carbohydrates serve as advantageous components of the total dissolved organic nitrogen (DON) and are the predominant compound class accounting for more than 50% of the material released by phytoplankton[61,73,74], congruent with high protein abundances found in this study (FIG. 39 second plot from the left on the top and bottom rows). *Chlamydomonas* did not vary significantly for the majority of compound classes (p>0.05) apart from a significant decrease in aromatic species at higher light exposure (0.51 vs 0.10%; p<0.05). While DOM released varied based on phytoplankton taxa, a higher light exposure led to an overall increase in smaller molecules that are generally more aliphatic and polar in structure. This suggests, while not wishing to be limited by theory, a shift towards a more protein- and lipid-rich environment as phytoplankton blooms progress in sub-Arctic environments.

(b) Hg-Cysteine

Hg complexation was observed in the presence of model ligands, i.e. cysteine where the exact mass was less than ±5 ppm for all Hg isotopes in a simple MeOH: $H_2O$ matrix[46]. Among the 6 Hg-containing formulas, $^{202}HgC_6H_{13}N_2O_4S_2^+$ was identified in the Hg-cysteine sample (1:2 molar ratio) in positive mode (FIG. 4O; top). The overall distribution of Hg isotopes was consistent with the theoretical isotopic distribution natural abundances[46] (FIG. 4O; bottom). The experimentally derived spectra revealed the $^{202}$Hg and $^{200}$Hg isotopes differing by -2.25 ppm and -2.26 ppm from the theoretical distribution, respectively as most abundant peaks. The peak intensity ratio between $^{202}$Hg and $^{200}$Hg was 0.81:1 for the detected Hg-Cys complex, comparable to the natural isotopic ratio (0.77:1)[46]. While the exact mass of Hg isotopes in other studies incorporating a 15T Fourier transform ion cyclotron mass spectrometry (FT ICR MS) achieved ±1 ppm, these results show that Hg isotopes can be usefully identified using Orbitrap mass spectrometry in complex mixtures[75]. While FT ICR-MS has become the stand alone method of choice for DOM characterization, Orbitrap mass spectrometry can be utilized for the accurate determination of molecular composition of DOM while providing confident information about dominant Hg isotopes[75].

(c) Changes in Hg Ligand Composition with Light

Entire spectra of phytoplankton-derived DOM were similar before and after Hg addition suggesting, while not limited by theory, limited ion suppression during ESI Orbitrap HRMS (FIGS. 23-34). A total of 44, 61 and 52 Hg-DOM complexes were detected at the 16:8 h light regime and increased to 85, 121 and 53 in the 20 h light cultures of Chlorella, Chlamydomonas, and Scenedesmus, respectively. Detected Hg-DOM complexes accounted for approximately 1.6-2.6% of the total assigned peaks across all samples. The addition of Hg to phytoplankton DOM allowed for the identification of Hg isotopologues while retaining similar peaks in the metal free sample (FIG. 41). Experimentally detected elemental formulas of $[^{202}HgC_{35}H^{60}O^7N^2S]^+$, $[^{202}HgC_{39}H_{82}O_6NS_2]^+$ and $[^{202}HgC_{37}H_{64}O_6N]^+$ were validated based on exact mass and theoretical Hg isotopic distribution in Chlorella, Chlamydomonas and Scenedesmus, respectively (FIG. 42; second from top, third from bottom, bottom, respectively). While $^{200}Hg$ and $^{202}Hg$ isotopes were checked for the isotopic confirmation of Hg, the presence of lower abundance Hg isotopes (i.e. $^{196}Hg$, $^{198}Hg$, $^{201}Hg$, and $^{204}Hg$) was also observed (FIG. 42) but at much lower relative intensities compared to a 15T FT ICR-MS[46].

At the 16:8 h light cycle, most DOM complexed to Hg were CHO in composition for Chlorella (15 formulas), Chlamydomonas (14 formulas) and Scenedesmus (10 formulas) (FIG. 43, top). The importance of Hg:DOM ratios when determining binding constants for Hg and DOM ligands has been demonstrated[76] and in natural conditions, Hg to DOM ratios are approximately 5 nM Hg/mg DOM where speciation is largely defined by reduced thiols functional groups[76]. In this study, Hg DOM ratios are 250 nM Hg/mg of DOM, suggesting, while not wishing to be limited by theory, that many Hg binding sites are dominated by oxygen functional groups[46, 61, 76]. However, at higher light regimes 20:4 (FIG. 43, bottom), compound classes containing both oxygen and nitrogen atoms composed of the vast majority of Hg bound DOM for Chlamydomonas and Scenedesmus due to the enhanced production and abundance of CHON coupled with high Hg:DOM ratios[61, 74]. Sulfur heteroatoms are an important variable to consider at lower Hg:DOM ratios and sulfur containing DOM content varied between taxa (5.15-5.89%). A total of eight $CHOS_2$ formulas produced by Chlamydomonas were bound to Hg, making it the most abundant sulfur containing class that binds to Hg at 16:8 h photoperiod duration (FIG. 43, top). Detected Hg binding DOM classes that contain at least one sulfur atom (CHOS, $CHOS_2$) increased from 9 to 54, 17 to 21 for Chlorella and Chlamydomonas, respectively but no significant change was observed for Scenedesmus (27 to 25 16:8-20:4 h), consistent with the overall trends in % $S_{wa}$ at higher light regimes (FIG. 35, second plot from right on bottom row). These results highlight that the increased light exposure prompted a 2.13-fold increase in the number of S-containing ligands Hg in Chlorella vulgaris mainly in the form of Hg bound CHONS compounds.

The proportion of Hg binding DOM also changed from 16 to 20 h light exposure. The most notable difference was the reduction in Hg bound CHO species in all taxa (15 to 11 molecules for Chlorella, 14 to 11 molecules for Chlamydomonas and 10 to 6 molecules for Scenedesmus) (FIG. 43, bottom). Increasing the light duration prompted a spike in CHONS compounds produced by Chlorella from 3 to 27 of all compounds complexed to Hg, consistent with the overall increase in protein material at higher light intensities (FIG. 39, second plot from left on top and bottom rows). Detected CHOS compounds complexed to Hg increased with light exposure across all taxa (3 to 10 for Chlorella, 3 to 7 for Chlamydomonas and 3 to 5 for Scenedesmus).

(d) Structural Properties of Hg Binding DOM

To assess how structural properties of Hg binding DOM vary between taxa and with light exposure, a two-way hierarchal cluster analysis with correlation heatmaps was conducted (FIGS. 44-45). Three clusters were found for each light regime based on 95% Bray-Curtis similarity measure (FIGS. 44-45). Group 1 included 70% of the molecular formula compound classes at the 16:8 h light regime, mainly from Scenedesmus and Chlorella, linked by similarities between % $N_{wa}$, $N/C_{wa}$, $m/z_{wa}$, % $H_{wa}$, $H/C_{wa}$ and % $C_{wa}$ of secreted Hg binding DOM. Chlamydomonas CHOS, $CHOS_2$, CHO and $CHON_2S$ Hg binding DOM compounds were clustered in Group 2, largely due to the strong influence of % $O_{wa}$, $O/C_{wa}$, $NOSC_{wa}$ and $AI_{mod}$. Group 3 included Chlorella and Scenedesmus $CHOS_2$ compounds, predominantly influenced by high % $S_{wa}$, $S/C_{wa}$, $O/C_{wa}$ and $NOSC_{wa}$. Chlorella and Scenedesmus produced smaller, N-rich and polar Hg binding ligands when compared to the larger more aromatic and oxygenated DOM released by Chlamydomonas. While changes in photoperiod duration yielded changes in the number and proportion of Hg-binding molecules, the overall structural properties $AI_{mod}$, % $C_{wa}$, % $H_{wa}$, % $O_{wa}$) of Hg-binding DOM did not significantly change. A significant change (p<0.05) in the proportion of CHO and CHONS at 16:8 to 20:4 was observed, but the overall structural properties of Hg binding DOM ($AI_{mod}$, $O/C_{wa}$, $N/C_{wa}$) did not significantly change between light regimes.

Higher light exposure increased % $S_{wa}$ and the number of Hg-sulfur interactions increased, the structural properties of the sulfur containing molecules did not significantly vary. The influence of phytoplankton taxa was more important on Hg binding DOM than the compositional changes caused by higher light exposure. As photoperiods increased, a shift from Hg complexed by CHO to CHONS, CHON and $CHON_2S$ ligands were observed indicating a shift from Hg binding to aromatic DOM towards Hg binding to protein-rich DOM[41,77]. With the availability of more sulfhydryl binding sites at increased photoperiods, a shift from amine and carboxyl functional groups to thiols may be observed, even at higher DOM:Hg ratios (Table 4)[78]. Structural properties of released DOM are largely governed by phytoplankton species and while assessing present thiol and sulfhydryl binding sites allows for predicting of Hg complexation, the structure of the side chain attached to the sulfur containing group has advantageous implications for the bioavailability of the complex[78,79]. While certain phytoplankton DOM abundant in low molecular weight thiols may act as a shuttle for Hg to bacteria, larger sinking phytoplankton DOM may facilitate Hg mobility to larger colloidal organic matter fractions where Hg methylation also occurs[41, 79, 80].

(e) Identification of Hg-Phytoplankton Derived DOM Complexes

The present research incorporates Orbitrap high resolution mass spectrometry to allow for the confident identification of Hg-phytoplankton derived DOM complexes. The low molecular weight DOM were identified to include at least desferrioxamine, cyclic trichrisobactin, carboxymycobactin monohydrate, exochelin from Chlorella; ferrioxamine from Chlamydomonas; desferrioxamine, desferrioxamine monohydrate, vibrioferrin and acinetoferrin from Scenedesmus; and siderochelin A, benarthin, chrysobactin, dihydroxybenzoic acid, rhizobactin, and schizokinen from Euglena. Table 5 shows the identities of LMW DOM compounds from Chlorella, Chlamydomonas, Scenedesmus and Euglena gracilis.

TABLE 5

Complexes identified in *Chlorella* (20:4); *Scenedesmus* (16:8) and (20:4); *Chlamydomonas* (16:8) and *Euglena*.

| Mass Details | Structure/Name |
|---|---|

*Chlorella* (20:4)

Theo Mass [H+]: 922.3844396
Observed: 922.38139
Error ppm: −3.306
Intensity: 32460.6
Relative: 0.34
Resolution: 55354.92
Formula: C31H57N7O12Hg

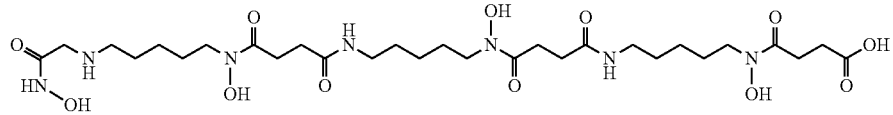

Desferrioxamine

Theo Mass [H+]: 980.3436366
Observed: 980.34074
Error ppm: −2.955
Intensity: 25337.9
Relative: 0.26
Resolution: 53989.57
Formula: C34H51N9O12Hg

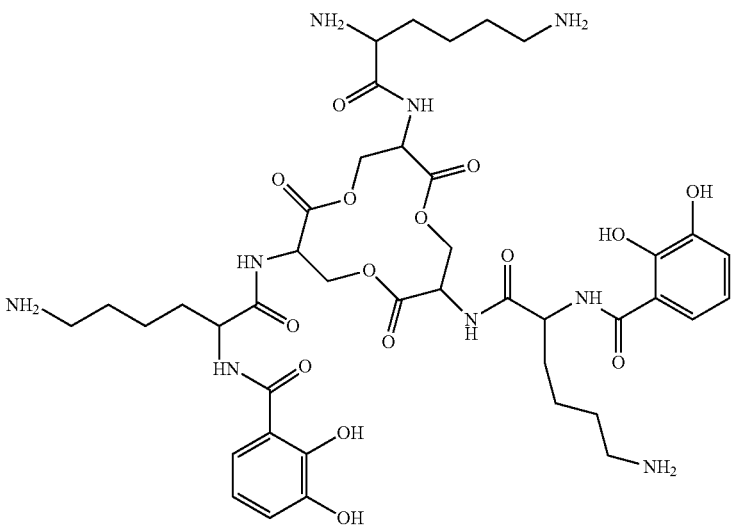

Cyclic trichrisobactin

Theo Mass [H+]: 978.3419056
Observed: 978.34468
Error ppm: 2.8358
Intensity: 22118.2
Relative: 0.23
Resolution: 57523.44
Formula: C37H54N5O13Hg

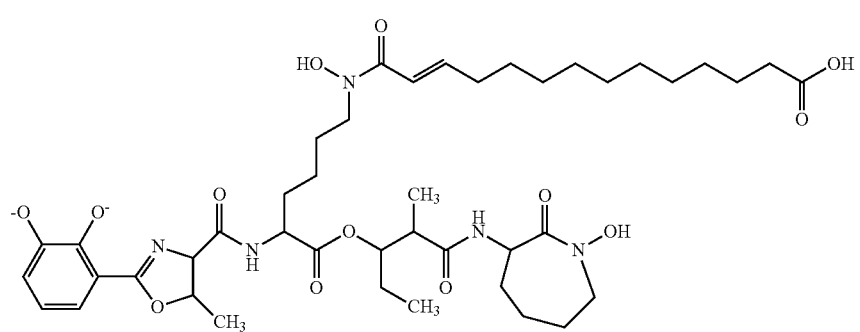

Carboxymycobactins (monohydrate)

TABLE 5-continued

Complexes identified in *Chlorella* (20:4); *Scenedesmus* (16:8) and (20:4); *Chlamydomonas* (16:8) and *Euglena*.

Theo Mass [H+]: 912.3385516
Observed: 912.34205
Error ppm: 3.8345
Intensity: 29098.5
Relative: 0.3
Resolution: 59399.79
Formula: C27H51N9O13Hg

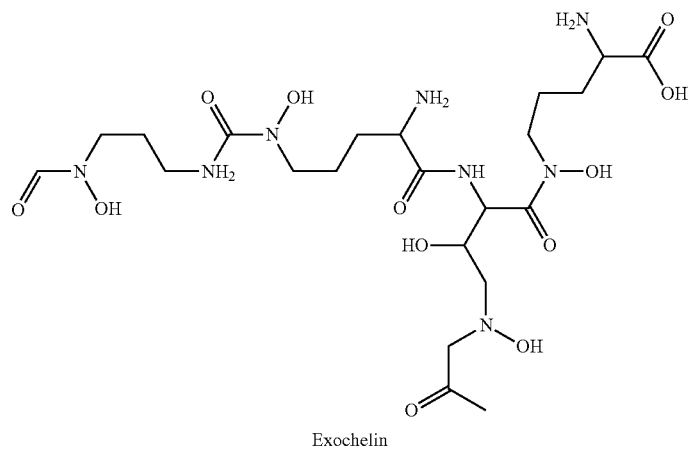 [SMILES: CC(=O)CN(O)CC(O)C(NC(=O)C(N)CCCN(O)C(=O)NCCCN(O)C=O)C(=O)N(O)CCCC(N)C(=O)O]

Exochelin

| Details | Structure/Name |
| --- | --- |

*Scenedesmus* (16:8)

Theo Mass [H+]: 870.3571616
Observed: 870.35989
Error ppm: 3.1348
Intensity: 74765.4
Relative: 0.13
Resolution: 65932.81
Formula: C32H53N5O10Hg

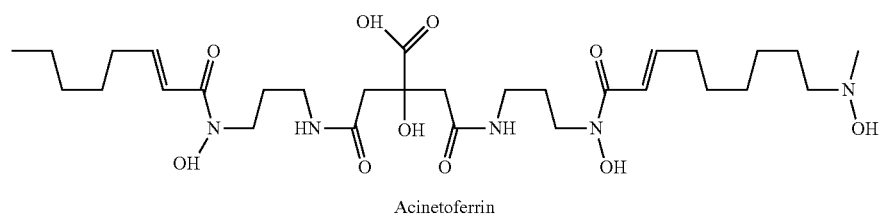

Acinetoferrin

Theo Mass [H+]: 918.3895246
Observed: 918.39265
Error ppm: 3.40312
Intensity: 102490.5
Relative: 0.18
Resolution: 64258.09
Formula: C32H57N7O11Hg

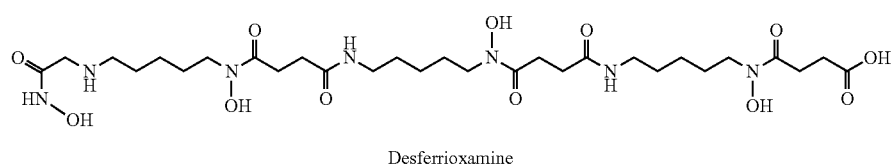 [SMILES: O=C(O)CCC(=O)N(O)CCCCCNC(=O)CCC(=O)N(O)CCCCCNC(=O)CCC(=O)N(O)CCCCCNCC(=O)NO]

Desferrioxamine

*Scenedesmus* (20:4)

Theo Mass [H+]: 633.0649906
Observed: 633.06433
Error ppm: −1.0435
Intensity: 44317.8
Relative: 0.1
Resolution: 71400.33
Formula: C16H18N2O12Hg

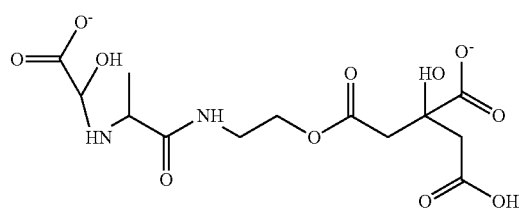

Vibrioferrin

Theo Mass [H+]: 870.3571616
Observed: 870.35982
Error ppm: 3.05437
Intensity: 58580.8
Relative: 0.13
Resolution: 63902.28
Formula: C32H53N5O10Hg

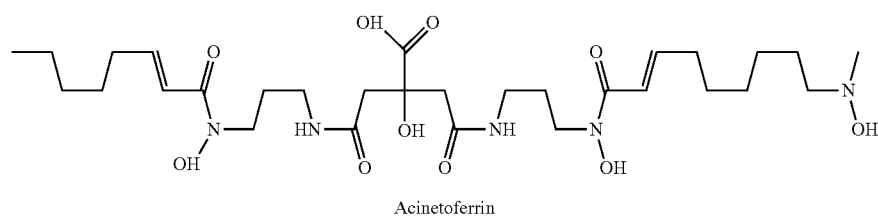 [SMILES: CCCCC/C=C/C(=O)N(O)CCCNC(=O)CC(O)(CC(=O)NCCCN(O)C(=O)/C=C/CCCCCCN(C)O)C(=O)O]

Acinetoferrin

TABLE 5-continued

Complexes identified in *Chlorella* (20:4); *Scenedesmus* (16:8) and (20:4); *Chlamydomonas* (16:8) and *Euglena*.

Theo Mass [H+]: 918.3895246
Observed: 918.39269
Error ppm: 3.44668
Intensity: 56188.2
Relative: 0.13
Resolution: 60213.31
Formula: C32H57N7O11Hg

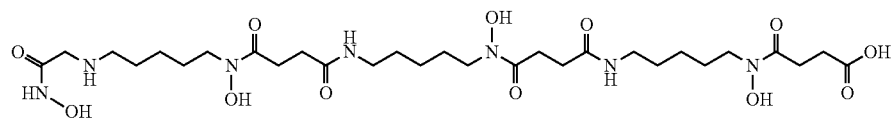

Desferrioxamine (monohydrate)

*Chlamydomonas* (16:8)

Theo Mass [H+]: 952.3864506
Observed: 952.38897
Error ppm: 2.645
Intensity: 20786.4
Relative: 0.15
Resolution: 56545.67
Formula: C36H57N6O11Hg

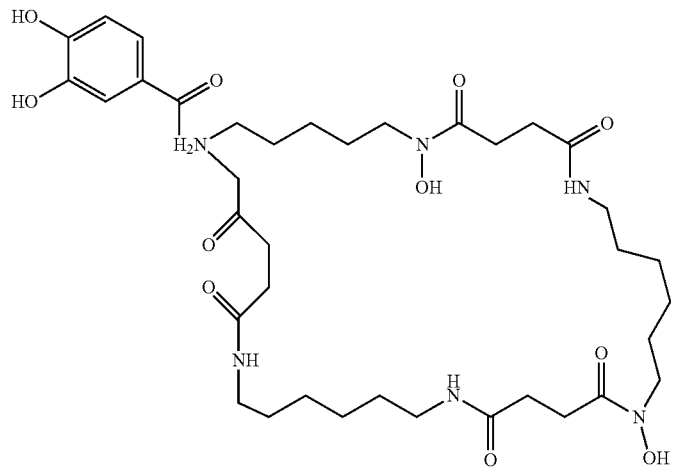

Ferrioxamine

*Euglena gracilis* Hg Binding DOM

Theo. Mass: 436.0653
Hg: 436.0658
No Hg: 234.1044
Intensity: 31598.2
Relative: 0.13
Delta (ppm): 1.05
RBE: 6.5
Composition: C12H14N2O3Hg
Composition-Hg: C12H14N2O3
Theo Mass no Hg: 234.1001
Error (ppm): 4.343

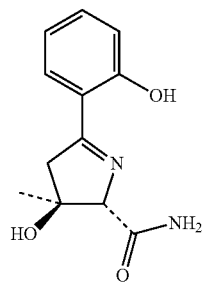

Siderochelin A

Theo. Mass: 614.1977
Hg: 613.1474
No Hg: 411.1768
Intensity: 69622.3
Relative: 0.3
Delta (ppm): −0.5
RBE: 14.5
Composition: C17H25N5O7Hg
Composition-Hg: C17H25N5O7
Theo Mass no Hg: 411.1748
Error (ppm): 1.983

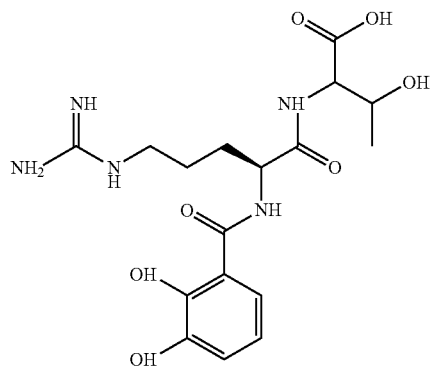

Benarthin

TABLE 5-continued

Complexes identified in *Chlorella* (20:4); *Scenedesmus* (16:8) and (20:4); *Chlamydomonas* (16:8) and *Euglena*.

Theo. Mass: 571.1191
Hg: 571.119
No Hg: 369.1546
Intensity: 37318.3
Relative: 0.16
Delta (ppm): −0.25
RBE: 15.5
Composition: C16H23N3O7Hg
Composition-Hg: C16H23N3O7
Theo Mass no Hg: 369.153
Error (ppm): 1.602

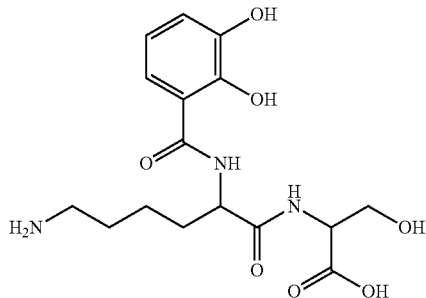

Chrysobactin

Theo. Mass: 355.9994
Hg: 355.999
No Hg: 154.02661
Intensity: 52415.8
Relative: 0.22
Delta (ppm): −1.12
RBE: 9.5
Composition: C7H6O4Hg
Composition-Hg: C7H6O4
Theo Mass no Hg: 154.0264
Error (ppm): 0.21

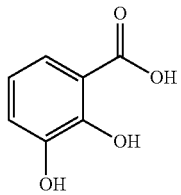

Dihydrobenzoic acid

Theo. Mass: 580.2134
Hg: 579.1473
No Hg: 377.17728
Intensity: 102489.9
Relative: 0.44
Delta (ppm): −0.18
RBE: 10.5
Composition: C15H27N3O8Hg
Composition-Hg: C15H27N3O8
Theo Mass no Hg: 377.1791
Error (ppm): −1.817

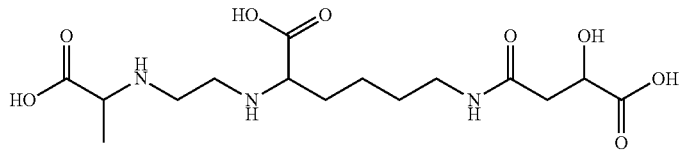

Rhizobactin

Theo. Mass: 621.9708
Hg: 622.1507
No Hg: 420.18008
Intensity: 24838.9
Relative: 0.11
Delta (ppm): −0.18
RBE: 4.5
Composition: C16H28N4O9Hg
Composition-Hg: C16H28N4O9
Theo Mass no Hg: 420.1849
Error (ppm): −4.817

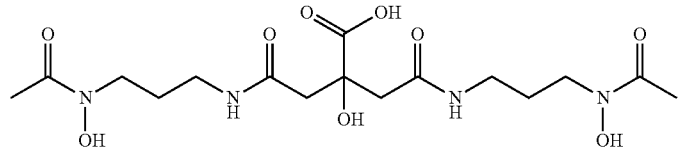

Schizokinen

By incorporating a top-down shotgun based approach, previously devised bacterial siderophores, KEGG ligand databases, and Metlin were searched to identify putative Hg binding metabolites present in phytoplankton exudates. While bacterial siderophores are traditionally produced to sequester iron required for metal homeostasis, these ligands have been known to interact with a wide range of soft metals, including Hg[81]. Based on siderophore databases[56], and comparing experimental and theoretical isotopic patterns, empirical formulas of seven potential Hg binding siderophores were identified (FIGS. 46-51). The putative compounds included desferrioxamine, cyclic trichrisobactin, carboxymycobactins, and exochelin in *Chlorella*, and acinetoferrin and desferrioxamine in *Scenedesmus*. While Hg-DOM complexes were detected for *Chlamydomonas*, none of these detected compounds were found in the siderophore database[56].

Using the KEGG ligand database, additional putative ligands were found based on exact mass and molecular composition (Table 6).

TABLE 6
KEGG Database Matches-Phytoplankton Exudates.
| Phytoplankton Exudate Sample | Molecular Formula (m/z) | Structure/Name |
|---|---|---|
| *Chlorella* 16:8 | C9H9O2N (163.0633) | 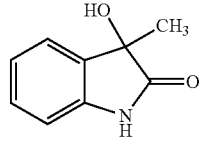<br>C05834<br>3-Methyldioxyindole |
| *Chlorella* 16:8 | C12H15O2N (205.1103) | 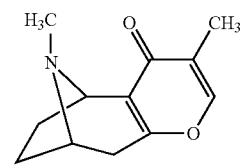<br>C10846<br>Bellendine |
| *Chlorella* 16:8 | C18H31O (264.244693) | 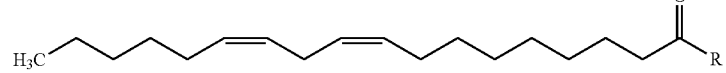<br>C21529<br>Linoleoyl (glycerolipid) |
| *Chlorella* 20:4 | C11H19O9NS (373.0501) | 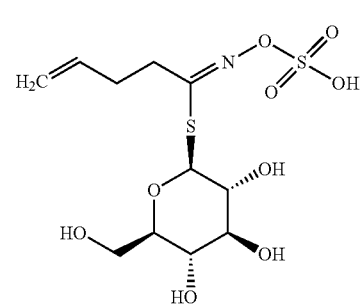<br>C08415<br>Gluconapin |
| *Chlorella* 20:4 | C19H35O4N3S (401.2348) | 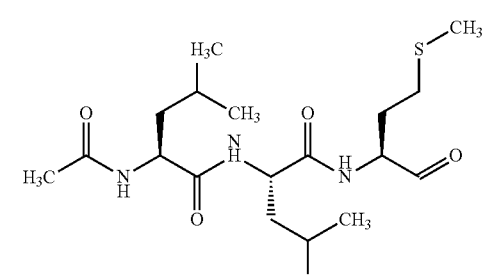<br>C11292<br>N-Acetylleucyl-leucyl-methionianal |

TABLE 6-continued

KEGG Database Matches-Phytoplankton Exudates.

| Phytoplankton Exudate Sample | Molecular Formula (m/z) | Structure/Name |
|---|---|---|
| Chlamydomonas 20:4 | C22H47O5N (405.3454) C19805 | [structure of Aminopentol] |

At lower light regimes, matches with molecules $C_9H_9O_2N$ and $C_{12}H_{15}O_2N$ with possible structures resembling 3-methyldioxyindole an indication of tryptophan metabolism and degradation[80] and N-acetyl-leucyl-methionine, a sulfur based amino acid protease inhibitor[82] in *Chlorella* exudates. Possible isomers of aminopentol ($C_{22}H_{47}O_5N$), a hydrolysis product of fungal mycotoxins commonly found on corn and other lipid-rich nutrient sources was found complexed to Hg in *Chlamydomonas* exudates at higher light regimes[83].

Examining phytoplankton exudates using Metlin yielded additional compounds of microorganism origin (Table 7). For example, $C_7H_{14}O_3$ found in *Chlorella* cultures at higher light regimes produced a potential isomer of a heptanoic acid, an oily carboxylic acid commonly found in algae complexed to Hg[84]. Furthermore, $C_{42}H_{81}NO_3$ found at *Chlamydomonas* during higher light regimes is a potential isomer of ceramide, a lipid assisting motile algae to swim towards light[85]. Finally, *Scenedesmus* at lower light durations revealed $C_{38}H_{67}N_2O_4S$, a possible isomer of tetradecane that possesses antimicrobial properties, complexing with Hg[86].

TABLE 7

Hg binding algal-derived ligands.

| m/z (Composition) | Name and Reference | Proposed Structure | Relative Abundance |
|---|---|---|---|
| *Chlorella* 16:8 | | | |
| 541.461563 (C36H61O3) | Momordicilin Kumar et al 2015[87] | [structure] | 0.67 |

TABLE 7-continued

Hg binding algal-derived ligands.

| m/z (Composition) | Name and Reference | Proposed Structure | Relative Abundance |
|---|---|---|---|
| 379.129713 (C15H25O8NS) | Sulfanilamide Singh 1975[88] | DTXCID80142255 | 0.27 |
| 551.503263 (C35H67O4) | Dihydroxypentatri-aconta-2,4-dienoic acid Laboratory techniques in Biochemistry and Molecular Biology. Chapter 1 Lipids[89] | | 0.23 |

*Chlorella* 20:4

| | | | |
|---|---|---|---|
| 155.080733 (C19H32O6N6) | Ala Thr Leu His Peptide chain of 4 amino acids | | 2.69 |
| 147.101563 (C7H14O3) | 2-Hydroxyheptanoic acid Everall and Lees 1997[90] | | 1.45 |

TABLE 7-continued

Hg binding algal-derived ligands.

| m/z (Composition) | Name and Reference | Proposed Structure | Relative Abundance |
|---|---|---|---|
| 145.085883 (C7H12O3) | (E)-penta-1,3-dien-2-ol Bagwell et al 2014[91] | | 0.87 |
| 629.513923 (C40H68O5) | Diglyceride Waxy lipid composed of two fatty chains Choi et al 1987[92] | | 0.35 |
| 471.367853 (C27H50O6) | Glycerol triaprylate U.S. Pat. No. 7,220,417 B2 | | 0.34 |
| | *Chlamydomonas* 16:8 | | |
| 377.086613 (C18H17O9) | 5,7,3',4'-Tetrahydroxy-3,6,5'-trimethoxyflavone Rabesa and Voirin 1980[93] | | 0.18 |

TABLE 7-continued

Hg binding algal-derived ligands.

| m/z (Composition) | Name and Reference | Proposed Structure | Relative Abundance |
|---|---|---|---|
| 423.419743 (C28H55O2) | 9-Octadecenoic acid Abdel-Aal et al. 2015[94] | DTXCID409259 | 0.29 |
| | *Chlamydomonas* 20:4 | | |
| 769.085773 (C33H22N4O17) | 1,2,3,4-tetrakis-o-(4-nitrobenzoyl) pentopyranose Vestola et al 2014[95] | | 1.16 |

TABLE 7-continued

Hg binding algal-derived ligands.

| m/z (Composition) | Name and Reference | Proposed Structure | Relative Abundance |
|---|---|---|---|
| 648.628843 (C42H81NO3) | Ceramide Michaelson et al 2010[96] | | 0.69 |
| 365.011463 (C11H12N2O8S2) | Cefsulodin monobactam Rossolini and Docquier 2006[97] | | 0.64 |
| 345.009093 (C14H7N2O8) | 2,7,9-Tricarboxypyrrolo(2,3-f)quinoline-4-ol-5-one Prince and Gallant 1983[98] | | 0.58 |

TABLE 7-continued
Hg binding algal-derived ligands.
| m/z (Composition) | Name and Reference | Proposed Structure | Relative Abundance |
|---|---|---|---|
| | | *Scenedesmus* 16:8 | |
| 616.475733 (C38H67N2O4S) | Tetradecane-1 Yamamoto et al 2014[99] | 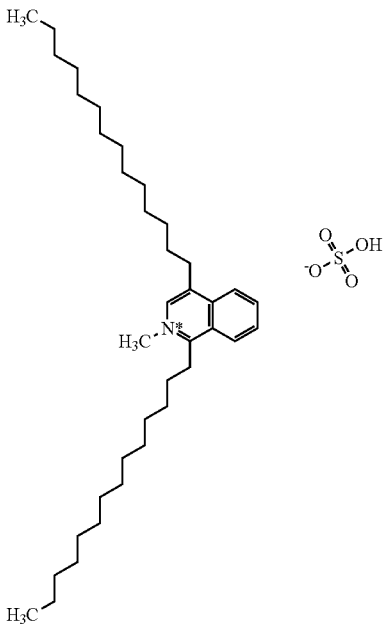 DTXCID60141766 | 0.30 |
| | | *Scenedesmus* 20:4 | |
| 619.478213 (C34H66O9) | 1-(O-alpha-D-glucopyranosyl)-3-keto-(1,25R,27R)-octacosanetriol Bauersachs 2010 (Thesis)[100] | 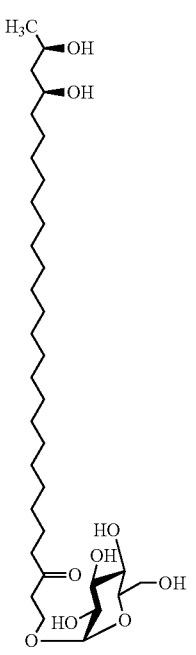 | 0.25 |

TABLE 7-continued

Hg binding algal-derived ligands.

| m/z (Composition) | Name and Reference | Proposed Structure | Relative Abundance |
|---|---|---|---|
| 661.464353 (C42H58N6O2) | 2,4-Bis[4,5-bis(pentylamino)isoquinolin-1-yl]cyclobutane-1,3-dione US 2008/0194732 A1 | DTXCID20751183 | 0.21 |

(f) Further Discussion

The present research incorporates Orbitrap high resolution mass spectrometry to allow for the identification of Hg-phytoplankton derived DOM complexes. Molecular composition of Hg-binding DOM can be confidently determined using Orbitrap HRMS. This study emphasizes the diversity in phytoplankton DOM composition between taxa at different photoperiods and how these DOM-Hg complexes can be detected and characterized using HRMS. It was showed that taxonomical differences in phytoplankton play a role in Hg binding and that greater similarities exist between *Scenedesmus* and *Chlorella* Hg-binding DOM than *Chlamydomonas*. The use of Orbitrap HRMS can be utilized for the putative identification of Hg binding DOM molecules.

Example 5: Effect of DOM Concentration on Bacterial Hg Bioavailability

I. Materials and Methods

Using bioreporter assays as described in Example 1, the impact of increasing concentrations of phytoplankton organic matter from *Chlorella, Chlamydomonas, Scenedesmus* and *Euglena gracilis* was evaluated. 5 nM of Hg in the absence of DOM was utilized as a calibration to observe a system lacking DOM in both oxic and anoxic conditions. Increasing concentrations of 0.1, 0.5 and 1 ppm DOM were allowed to bind to Hg for 1 hour prior to assays for *Chlorella, Chlamydomonas, Scenedesmus*. For *Euglena*, concentrations ranged from 1, 5, 10, 20 and 30 ppm DOM were used as concentrations >1 ppm did not significantly impact Hg mobility.

Orbitrap high resolution mass spectrometry was also conducted for *Euglena gracilis* at 1 and 30 ppm DOM to evaluate how DOM composition changes with concentration.

II. Results and Discussion

As DOM concentrations increase, there is a consistent and significant trend where Hg mobility decreases for all phytoplankton in both aerobic and anaerobic assays, except for *Euglena gracilis* in aerobic assays. Increasing concentrations >10 ppm DOM were shown to enhance Hg mobility into *E. coli* cells (FIG. 52). Orbitrap high resolution mass spectrometry spectra reveal that although some higher molecular weight DOM molecules are being produced by *Euglena gracilis* at 1 ppm DOM, these compounds are not preferentially released at higher DOM concentrations of 30 ppm DOM (FIG. 53). While not wishing to be limited by theory, these results show that the enhancement of low molecular weight molecules being selectively released by *Euglena gracilis* at higher DOM concentrations may shuttle Hg ions bound to these potential energy sources for smaller bacteria.

Example 6: Identification of Organic Ligands in Dissolved Organic Matter Produced by *Scenedesmus obliquus* Using Fourier Transform Ion Cyclotron Resonance Mass Spectrometry Laboratory grown cultures of *Scenedesmus obliquus* were obtained from the Canadian Phycological Culture Center (CPCC) in Waterloo, Ontario. The cells were grown using a bold basal media (BBM) at standard light regimes (16:8 h light to dark) fixed light intensity of 90-100 µmol photons $m^{-1}s^{-1}$ and fixed temperature of 21° C. constantly aerated in a growth chamber.

The toxicity of Cd (EC50=133 pbb or $\mu L^{-1}$ Cd) was determined using increasing concentration of $Cd(NO_3)_2$. Four algal cultures were grown in the presence of varying levels of Cd: control (0 $\mu L^{-1}$ Cd); EC20 (19.5 $\mu L^{-1}$ Cd); EC30 (46.4 $\mu L^{-1}$ Cd) and EC40 (78.8 $\mu L^{-1}$ Cd) starting at 1 million cells per mL for Replicate 1 and 2 million cells per mL for Replicate 2. The cells were harvested in early stationary phase for further analysis.

The supernatant (exudates) was separated from the cells by centrifugation. The exudates were filtered using a 0.45 µm Whatman filter. An aliquot that was made up of 50% methanol and 50% filtered exudates was adjusted to a pH of 6 before analysis using FT ICR-MS (FT-ICR ESI 7 Tesla, 16M; Range: m/z 200-2000; 200 scans in Negative Mode). Another set of exudates was spiked with 100 nM (Rep 1) and 300 nM (Rep 2) Cd (ICP-MS standard) at a pH of 6 and incubated overnight prior to analysis.

Data were exported and analyzed using Compass data analysis software (version 4.2, Bruker Daltonics). In order to detect Cd containing compounds the software Winnow[45] was used to detect 8 isotopologues of Cd ($^{106}$Cd, $^{108}$Cd, $^{110}$Cd, $^{111}$Cd, $^{112}$Cd, $^{113}$Cd, $^{114}$Cd and $^{116}$Cd). Only the peaks with a Winnow score of greater than 90% were further compared with respect to ratios of natural Cd abundances of at least $^{112}$Cd and $^{114}$Cd to confidently identify Cd molecular compositions using Compass data analysis Isotope simulation functions. In order to identify putative ligand complexes with Cd, the peaks with a Winnow score of greater than 90% were further compared to a modified database of known siderophores and their derivatives as well as different metabolomic online database such as Metlin, Chemspider, ChEBI, KEGG or Pubchem[45,54-56] based on accurate m/z with an error ppm.

The number of complexes were quite similar between Rep 1 and Rep 2 of the exudates derived from EC30 treatment (Table 8). However, an increase of complexes was observed in Rep 2 in most of the treatments. The number of complexes found in Rep 2 was greater than in Rep 1, while not wishing to be limited by theory, because of the higher cell densities Cd concentration were used in Rep 2.

TABLE 8

Number of Cd Complexes Found by Winnow Software

| Sample | No. Complexes Rep 1 | No. Complexes Rep 2 |
|---|---|---|
| EC20 | 57 | 167 |
| EC30 | 63 | 62 |
| EC40 | 41 | 99 |
| Spiked Control* | 63 | 104 |
| Spiked EC40** | 57 | 136 |

*Exudates produced by cells grown in the absence of Cd.
**Cells grown with Cd (EC40 level) and exudates spiked and incubated with 100 or 300 nM Cd.

Five compounds were found in the exudates of two biological replicates of cells grown in the absence of Cd ("Control") and at EC40 (Table 9). The proposed structures for the Cd-binding structures have been validated based on exact mass and natural Cd isotopic distribution. All proposed structures have been previously reported in microorganisms.

TABLE 9

Compound Details.

| Sample | Rep 1 complex m/z | Rep 2 complex m/z | Formula/Ligand Formula/Name | Chemspider ID | Ligand Reference |
|---|---|---|---|---|---|
| Spiked Control | 956.3886 | 956.3891 | $C_{37}H_{66}CdN_{10}O_{12}$ $C_{37}H_{66}N_{10}O_{12}$ Oligopeptides | 8366570 9345484 9495360 | Chemspider Chemspider Chemspider |
| Spiked EC40 | 878.4356 | 878.4351 | $C_{43}H_{74}CdNO_{10}$ $C_{43}H_{76}NO_{10}$ Bacteriohopanetetrol cyclitol ether | 58163504 | Schmerk et al., 2015[101] |
| Spiked EC40 | 940.37703 | 940.37839 | $C_{46}H_{68}CdNO_{12}$ $C_{46}H_{70}NO_{12}$ Azaspiracid-3 | 28469198 | Percopo et al., 2013[102] |
| Spiked EC40 | 958.3871 | 958.3879 | $C_{45}H_{64}CdN_8O_8$ $C_{45}H_{64}N_8O_8$ Brunsvicamide A | 10019079 | Müller et al., 2006[103] |
| EC40 | 958.3877 | 958.3878 | $C_{45}H_{64}CdN_8O_8$ $C_{45}H_{64}N_8O_8$ Brunsvicamide A | 10019079 | Müller et al., 2006[103] |

The molecular formula for oligopeptide complexes were identified (FIG. 54) by matching the top five Cd isotopes ($^{106}$Cd, $^{108}$Cd, $^{114}$Cd) with their predicted intensities (bottom panel). Three potential candidates for the Cd-binding ligands found in exudates produced by Scenedesmus in the absence of Cd were found: L-Leucyl-L-asparaginylglycyl-L-lysyl-L-alanyl-L-leucyl-L-valyl-L-glutamic acid (ChemSpider ID8366570); L-Leucyl-L-asparaginylglycyl-L-lysyl-L-alanyl-L-leucyl-L-valyl-L-glutamic acid (ChemSpider ID8366570) and L-Valyl-L-asparaginyl-L-isoleucyl-L-glutaminyl-L-lysyl-L-α-glutamyl-L-isoleucine (ChemSpider 109495360), which have the following structures, respectively:

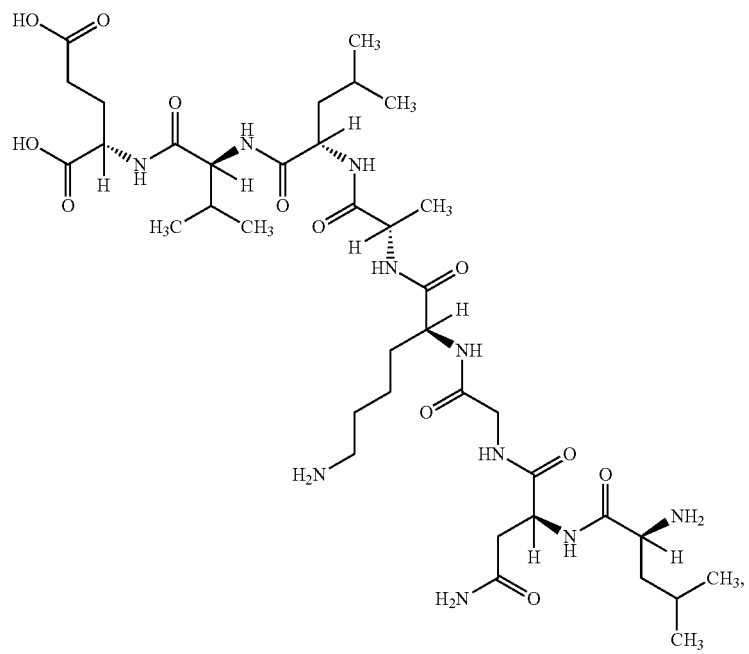
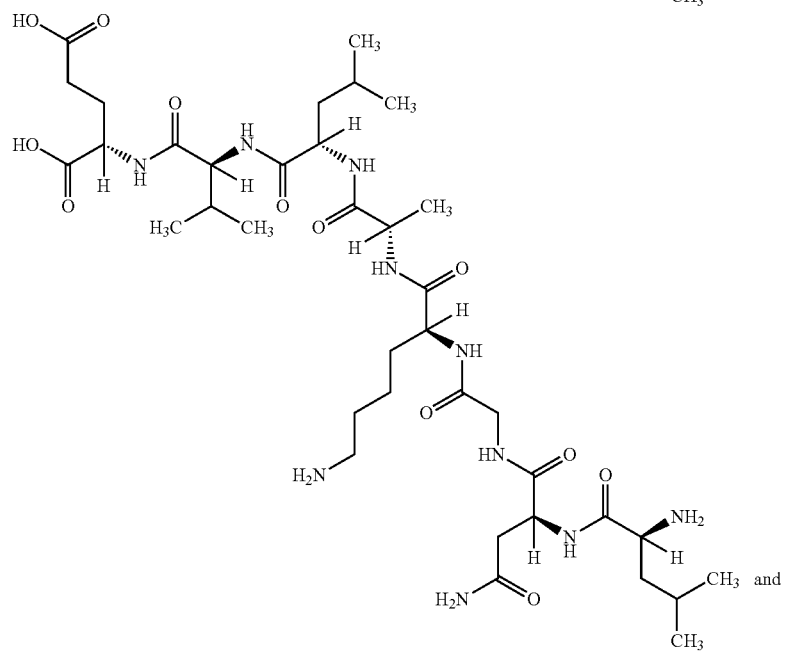
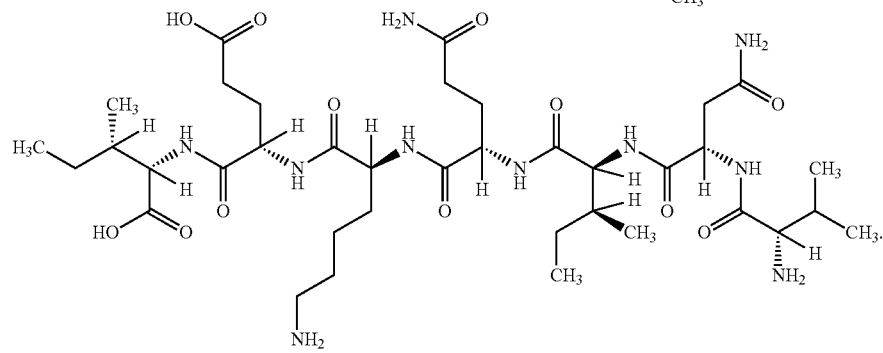
FIG. 55 shows an observed mass spectrum (top) compared to the corresponding predicted mass spectrum (bottom) for bacteriohopanetetrol cyclitol ether—Cd complex which ligand has the following structure:

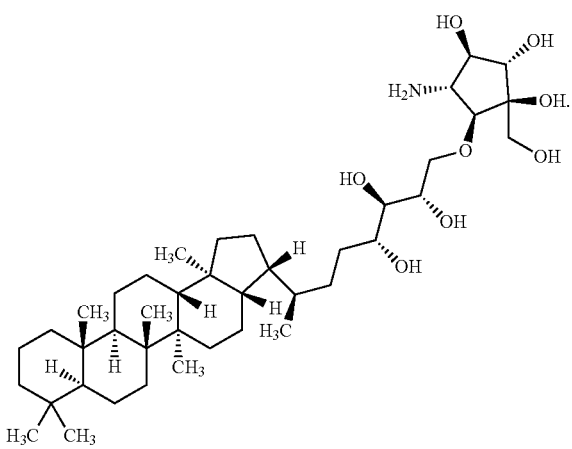

FIG. 56 shows an observed mass spectrum (top) compared to the corresponding predicted mass spectrum (bottom) for Azaspiracid-3—Cd complex which ligand has the following structure:

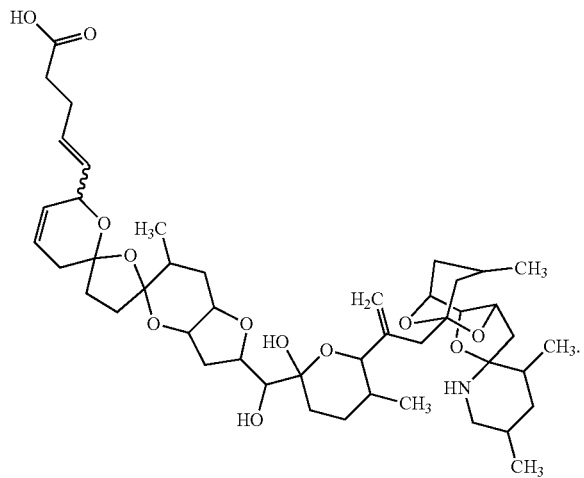 [SMILES: C=C(CC12CC(C)CC(O1)C1OC3(CC1O2)NCC(C)CC3C)C1OC(O)(C(O)C2CC3OC4(CCC5(CC=CC(C=CCCC(=O)O)O5)O4)C(C)CC3O2)CCC1C]

FIG. 57 shows an observed mass spectrum (top) compared to the corresponding predicted mass spectrum (bottom) for Brunsvicamide A—Cd complex, which ligand has the following structure:

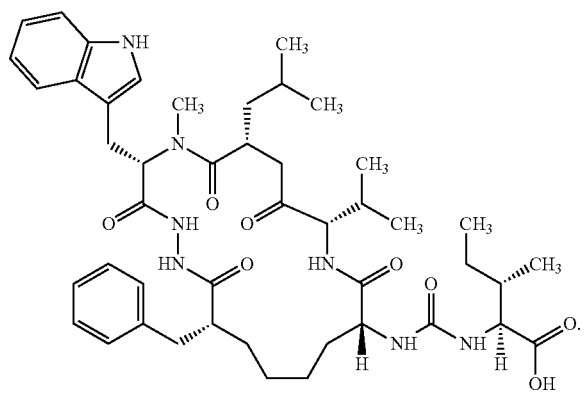 [SMILES: CC[C@H](C)[C@H](NC(=O)N[C@@H]1CCCC[C@H](Cc2ccccc2)C(=O)NNC(=O)[C@H](Cc2c[nH]c3ccccc23)N(C)C(=O)[C@H](CC(C)C)CC(=O)[C@H](C(C)C)NC1=O)C(=O)O]

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION (1a) Driscoll C. T., Mason R. P., Chan H. M., Jacob D. J., Pirrone N. Mercury as a Global Pollutant: Sources, Pathways and Effects. *Environ Sci. Technol.* 2013, 47, 4967-4983.

(1b) Lehnherr I., St. Louis V. L Hintelmann H., Kirk J. L. 2011. Methylation of inorganic mercury in polar marine waters. Nat Geosci. 4:298-302

(2) Graham A. M., Aiken G. R., Gilmour C. C. 2012. Dissolved Organic Matter Enhances Microbial Mercury Methylation Under Sulfidic Conditions. *Environ Sci. Technol.* 2012, 46, 2715-2723.

(3) Dieguez M. C., Queimalinos C. P., Guevara R., DiPasquale M. M., Cardenas C. S., et al. Influence of Dissolved Organic Matter Character on Mercury Incorporation by planktonic organisms: An Experimental study using oligotrophic water from Patagonian Lakes. *J. Environ. Sci.* 2013, 25 (10), 1980-1991.

(4) Cole, J. J., Carpenter, S. R., Pace, M. L., Van de Bogert, M. C., Kitchell, J. L. and Hodgson, J. R. Differential support of lake food webs by three types of terrestrial carbon. *Ecolo. Lett.* 2006, 9 (5), 558-568.

(5) Aiken G. R., Gilmour C. C., Krabbenhoft D. P., Orem W. Dissolved Organic Matter in the Florida Eerglades: Implications for Ecosystem Restoration. *Environ. Sci. Technol.* 2011, 41 (1), 271-248.

(6) Oestreich W. K., Ganju N. K., Pohlman J. W., Suttles S. E. Colored Dissolved Organic Matter in Shallow Estuaries: Relationships between Carbon sources and light attenuation. *Biogeosciences.* 2016, 13, 583-595.

(7) Miller C. L., Mason R. P., Gilmour C. G., Heyes A. Influence of Dissolved Organic Matter on the Complexation of Mercury Under Sulfidic Conditions. *Environ. Toxicol. Chem* 2007, 26 (4), 624-633.

(8) Schaefer J. K., Szczuka A., Morel F. M. M. Effect of Divalent Metals on Hg (II) Uptake and Methylation by Bacteria. *Environ. Sci. Technol.* 2014, 48, 3007-3013.

(9) Sun L., Perdue E. M., Meyer J. L., Weis J. Use of Elemental Composition to Predict Bioavailability of Dissolved Organic Matter in Georgia River. *Limnol. Oceanogr.* 1997, 42 (4), 714-721.

(10) Hopkinson C. S., Buffman I., Hobbie J., Vallino J., Perdue M et al. Terrestrial inputs of organic matter to Coastal Ecosystems: An Intercomparison of Chemical Characteristics and Bioavailability. *Biogeochem.* 1998, 43, 211-234.

(11) Xia K., Skyllberg L., Bleam W. F., Bloom P. R., Naer E. A., Helmke P. A. X-Ray Absorption Spectroscopic Evidence for the Complexation of Hg (II) by Reduced Sulfur in Soil Humic Substances. *Environ. Sc. Technol.* 1999, 33, 257-261.

(12) Hasterberg D., Chou J. W., Hutchison J. K., Sayers D. E. Bonding of Hg (II) to reduced organic sulfur in humic acid as affected by S/Hg ratio. *Environ. Sci. Technol.* 2001, 35 (13), 2741-2745.

(13) Drexel R. T., Haitzer M., Ryan J. N., Aiken G. R., Nagy K. L. Mercury (II) sorption to two Florida Everglades peats: evidence for strong and weak binding and competition by dissolved organic matter released from the peat. *Environ. Sci. Technol.* 2002, 36 (19), 4058-4064.

(14) Muresan B., Pernet Coudrier B., Cossa D., Varrault G. Measurement and modeling of mercury complexation by dissolved organic matter isolates from freshwater and effluents of a major wastewater treatment plant. *Appl. Geochem.* 2011, 26, 2057-2063.

(15) Seitzinger S. P., Hartnett H., Mazurek L. M., Minegishi T., Spyres G., et al. Molecular-level chemical characterization and bioavailability of dissolved organic matter using electrospray ionization mass spectrometry. *Limnol. Oceanogr.* 2005, 50 (1), 1-12.

(16) Amon R. M. W., Benner R. Photochemical and microbial consumption of dissolved organic carbon and dissolved oxygen in the Amazon River System. *Geochimica. Cosmochim Acta.* 1996, 60 (10), 41-51.

(17) Cabaniss S. E., Madey G., Leff L., Maurice P. A., Wetzel R. A stochastic model for the synthesis and degradation of natural organic matter. Part I. Data structures and reaction kinetics. *Biogeochem.* 2005, 76, 319-347.

(18) Smith S. Metal Speciation in Natural Waters with Emphasis on Reduced Sulfur Groups as Strong Metal Bindings Sites. *Comp Biochem Phys C.* 2002, 133, 65-74.

(19) Superville P. J., Pizeta I., Omanovic D., Billon G. Identification and on-line monitoring of reduced sulfur species (RSS) by voltammetry in oxic waters. *Talanta.* 2013, 112, 55-62.

(20) Yang X., Jiang C., Hsu-Kim H., Badireddy A. R., Dykstra M., Wiesner M., Hinton D. E., Meyer J. N. Silver Nanoparticle Behavior, Uptake and Toxicity in *Caenorhabditis elegans*: Effect of Natural Organic Matter. *Environ. Sci. Technol.* 2014, 48, 3486-3495.

(21) Mangal V., Guéguen C. Examining concentrations and molecular weights of thiols in microorganism cultures and in Churchill River (Manitoba) using a fluorescent-labeling method coupled to asymmetrical flow field-flow fractionation. *Anal. Bioanal. Chem.* 2015, 407, 4305-4313.

(22) Balch J., Guéguen C. Effects of Molecular Weight on the Diffusion Coefficient of Aquatic Dissolved Organic Matter and Humic Substances. *Chemosphere.* 2015, 119, 498-503.

(23) Cuss C. W. Guéguen C. Impacts of Microbial Activity on the Optical and Copper-Binding Properties of Leaf-Litter Leachate. *Front. Microbiol.* 2012, 3 (166), 1-10.

(24) Selifonova O., Burlage R., Barkay T. Bioluminescent Sensors for Detection of Bioavailable Hg (II) in the Environment. *Appl. Environ. Micro.* 1993, 59 (9), 3083-3090.

(25) Chiasson-Gould S. A., Blasis M. J., Poulain J. A. Dissolved Organic Matter Kinetically Controls Mercury Bioavailability. *Environ. Sci. Technol.* 2014, 48, 3153-3161.

(26) Qi Y., Barrow M. P., Li H., Meier S. E., Van Orden S. L. Absorption-Mode: The Next Generation of Fourier Transform Mass Spectra. *Anal. Chem.* 2012, 84, 2923-2929.

(27) D'Andrilli J., Foreman C. M., Marshall A. G., McKnight D. M. Characterization of IHSS Pony Lake fulvic acid dissolved organic matter by electrospray ionization Fourier transform ion cyclotron resonance mass spectrometry and fluorescence spectroscopy. *Org. Geochem.* 2013, 65, 19-28.

(28) Mangal V., Stock N. L., Guéguen C. Molecular characterization of phytoplankton dissolved organic matter (DOM) and sulfur components using high resolution Orbitrap Mass Spectrometry. *Anal. Bioanal. Chem.* 2016, 408 (7), 1891-1900.

(29) Kim S., Kramer R. W., Hatcher P. G. Graphical Method dor Analysis of Ultrahigh-Resolution Broadband Mass Spectra of natural Organic Matter, the Van Krevelen Diagram. *Anal. Chem.* 2003, 75, 5336-5344.

(30) Koch B. P., Dittmar T. From mass to structure: An aromaticity Index for High-Resolution Mass Data of Natural Organic Matter. *Rap. Comm. Mass. Spec.* 2006, 20, 926-932.

(31) Hammer, Ø., Harper, D. A. T., Ryan, P. D. PAST: Paleontological Statistics Software Package for Education and Data Analysis. *Palaeontol. Electron.* 2001, 4 (1), 9.

(32) Barkay T., Gillman M., Turner R. R. Effects of Dissolved Organic Carbon and Salinity on Bioavailability of Mercury. *App. Environ. Micro.* 1997, 63 (11), 4267-4273.

(33) Cory M. R., McNeill K., Cotner J. P., Amado A., Purcell J. M., Marshall A. G. Singlet Oxygen in the Coupled Photochemical and Biochemical Oxidation of Dissolved Organic Matter. *Environ. Sci. Technol.* 2010, 44, 3683-3689.

(34) Moreau J. W., Gionfriddo C. M., Krabbenhoft D. P., Ogorek J. M., DeWild J. F., Aiken G. R., Roden E. E. The Effect of Natural Organic Matter on Mercury Methylation by Desulfobulbus propionicus 1pr3. *Front. Microbiol.* 2015, 6 (1389), 1-15.

(35) Lemire J. A., Harrison J. J., Turner R. J. Antimicrobial activity of Metals: Mechanism, Molecular Targets and Applications. *Nat. Rev. Microbiol* 2016, 11, 371-384.

(36) Peuravuori J., Pihlaja B. K. ESI-MS analyses of Lake Dissolved Organic Matter in Light of Supramolecular Assembly. *Anal. Bioanal Chem.* 2007, 389, 1559-1568.

(37) Ma W., Zhang M., Wang R., Xin B., Guo W., Dai J. Mercury (II) Adsorption on Three Contrasting Chinese Soils Treated with Two Sources of Dissolved Organic Matter: II. Spectroscopic Characterization. *Soil Sed. Cont.* 2015, 24, 719-730.

(38) Mierle G. and Ingram R. The Role of Humic Substances in the mobilization of Mercury from watersheds. *Water Air Soil Pollut* 1991, 56 349-357.

(39) Benoit J. M., Mason R. P., Gilmour C. C., Aiken G. R. Constants for Mercury Binding by Dissolved Organic Matter Isolates from the Florida Everglades. *Geochim. Cosmochim. Acta.* 2001, 65 (24), 4445-4451.

(40) Ravichandran M. Interactions between Mercury and Dissolved Organic Matter-A Review. *Chemosphere.* 2004, 55:319-331.

(41) Schartup A. T., Ndu U., Balcom P. H., Mason R. P., Sunderland E. M. Contrasting Effects of Marine and Terrestrially Derived Dissolved Organic Matter on mercury Speciation and Bioavailability in Seawater. *Environ. Sci. Technol.* 2015, 49, 5965-5972.

(42) Ndu U., Mason R. P., Zhang H., Lin S., Visscher P. T. Effect of Inorganic and Organic Ligands on the Bioavailability of Methylmercury as Determined by Using a mer-lux Bioreporter. *App. Environ. Microbiol.* 2012, 78 (20), 7276-7282.

(43) Schnitzer M., Neyroud J. A. The alkaline hydrolysis of humic substances. *Geoderma.* 1975, 13, 171-188.

(44) Ohno et al., *Anal. Bioanal. Chem.* 2013, 405, 3299-3306.

(45) Doran M., Leblanc K. A computer program to simplify analysis of mass scan data of organometallic compounds from high-resolution mass spectrometers. *Rap. Comm. Mass Spec.*, 2016, 30, 2561-25.

(46) Chen, H., et al., Identification of Mercury and Dissolved Organic Matter Complexes Using Ultrahigh Resolution Mass Spectrometry. Environ. Sci. Technol. Lett., 2017, 4, 59-65.

(47) Ngu-Schwemlein, M., et al., Synthesis and ESI mass spectrometric analysis of the association of mercury(II) with multi-cysteinyl peptides. *J Inorg Biochem*, 2014, 133, 8-23.

(48) Solliec, M., A. Roy-Lachapelle, and S. Sauve, Quantitative performance of liquid chromatography coupled to Q-Exactive high resolution mass spectrometry (HRMS) for the analysis of tetracyclines in a complex matrix. *Anal Chim Acta*, 2015, 853, 415-424.

(49) Ohno, T. and P. E. Ohno, Influence of heteroatom pre-selection on the molecular formula assignment of soil organic matter components determined by ultrahigh resolution mass spectrometry. *Anal. Bioanal. Chem.*, 2013, 405 (10), 3299-3306.

(50) Roth, V. N., et al., The molecular composition of dissolved organic matter in forest soils as a function of pH and temperature. *PLoS One*, 2013, 10 (3), 1-23.

(51) Roth, V.-N., et al., Latitude and pH driven trends in the molecular composition of DOM across a north south transect along the Yenisei River. *Geochim Cosmochim Acta*, 2013, 123, 93-105.

(52) Riedel, T., H. Biester, and T. Dittmar, Molecular fractionation of dissolved organic matter with metal salts. *Environ Sci Technol*, 2012, 46, 4419-4426.

(53) Sipler, R. E., Kellogg, C. T. E., Connelly, T. L., Roberts, Q. N., Yager, P. L., Bronk, D. A. 2017. Microbial Community Response to Terrestrially Derived Dissolved Organic Matter in the Coastal Arctic. *Frontiers in Microbiology*. 8(1018): p. 1018.

(54) Baars, O., Morel, F. M. M., Perlman, D. H. 2014. ChelomEx: Isotope-assisted discovery of metal chelates in complex media using high-resolution LC-MS. *Analytical Chemistry*. 86(22): p. 11298-305.

(55) Hider, R. C., and Kong, X. 2009. Chemistry and biology of siderophores. *Natural Product Reports*. 27(5): p. 637-57.

(56) Bertrand, S. Siderophore Base—The Web Data Base of Microbial Siderophores. 2014.

(57) Kanehisa, M. G., Goto, S. 2000. *KEGG-Kyoto Encyclopedia of Genes and Genomes. Nucleic Acids Research.* 28(1): p. 27-30.

(58) Smith, A. C., O'Maille, G., Want, J. E., Qin, C., Trauger, A. S., et al. 2005. Metlin-A metabolite mass spectral database. *Therapeutic Drug Monitoring*. 27(6): p. 747-751.

(59) Han, J., Danell, R. M., Patel, J. R., Gumerov, D. R., Scarlett, C. O., et al. 2008. Towards high-throughput metabolomics using ultrahigh-field Fourier transform ion cyclotron resonance mass spectrometry. *Metabolomics*. 4(2): p. 128-140.

(60) Lancelot, C. 1984. Extracellular Release of Small and Large Molecules by Phytoplankton in the Southers Bight of the North Sea. *Estuaries, Coastal & Shelf Science*. 18: p. 65-77.

(61) Thornton, D. C. O. 2014. Dissolved organic matter (DOM) release by phytoplankton in the contemporary and future ocean. *European Journal of Phycology*. 49(1): p. 20-46.

(62) Holguin, F. O. and Schaub, T. 2013. Characterization of microalgal lipid feedstock by direct-infusion FT-ICR mass spectrometry. *Algal Research*. 2(1): p. 43-50.

(63) Ward, C. P., and Cory, R. M. 2016. Complete and Partial Photo-oxidation of Dissolved Organic Matter Draining Permafrost Soils. *Environmental Science & Technology*. 50(7): p. 3545-53.

(64) Duong, V. T., Ahmed, F., Thomas-Hall, S. R., Quigley, S Nowak, E., et al. 2015. High protein- and high lipid-producing microalgae from northern Australia as potential feedstock for animal feed and biodiesel. *Frontiers in Bioengineering & Biotechnology*. 3(53): p. 1-7.

(65) Schulze, C., Reinhardt, J., Wurster, M., Ortiz-Tena, J. G., Sieber, V., et al. 2016. A one-stage cultivation process for lipid- and carbohydrate-rich biomass of *Scenedesmus obtusiusculus* based on artificial and natural water sources. *Bioresource Technology*. 218: p. 498-504.

(66) Rasala, B. A. and Mayfield, S. P. 2015. Photosynthetic biomanufacturing in green algae; production of recombinant proteins for industrial, nutritional, and medical uses. *Photosynthesis Research*. 123(3): p. 227-39.

(67) Pirastru, L., Perreault, F., Chu, F. L., Oukarroum, A., Sleno, L., et al. 2012. Long-term stress induced by nitrate deficiency, sodium chloride, and high light on photosystem II activity and carotenogenesis of green alga *Scenedesmus* sp. *Botany*. 90(10): p. 1007-1014.

(68) Dupont, C. L., Geopfert, T. J., Lo, P., Wei, L., Ahner, B. A. 2004. Diurnal cycling of GSH in marine phytoplankton: Field and culture studies. *Limnology and Oceanography*. 49(4): p. 991-996.

(69) Baba, M., and Shiraiwa. Y. 2013. Biosynthesis of Lipids and Hydrocarbons in Algae, Photosynthesis: Agricultural and Biological Sciences. ISBN: 978-953-51-1161-0.

(70) Aluwihare, L. I., Repeta, D. J., Chen, R. F. 1997. A major biopolymeric components to DOC in surface sea water. *Letters to Nature*. 387(8): p. 166-169.

(71) Martone, P. T., Estevez, J. M., Lu, F., Ruel, K., Denny, M. W., et al. 2009. Discovery of lignin in seaweed reveals convergent evolution of cell-wall architecture. *Current Biology*. 19(2): p. 169-75.

(72) Hernes, P. J., Robinson, A. C., Aufdenkampe, A. K. 2007. Fractionation of lignin during leaching and sorption and implications for organic matter "freshness". *Geophysical Research Letters*. 34(17): p. 1-6.

(73) Yamada, E., Ohara, S., Uehara, T., Hirota, T., Hatori, N., et al. 2012. Biodegradation of Dissolved Organic Matter released from Phytoplankton in Lake Biwa. *Analytical Sciences*. 28: p. 675-681.

(74) Bronk, D. A., See, J. H., Bradley, P., Killberg, L. 2007. DON as a source of bioavailable nitrogen for phytoplankton. *Biogeosciences*. 4: p. 283-296.

(75) Remucal, C. K., Cory, R. M., Sander, M., McNeill, K. 2012. Low molecular weight components in an aquatic humic substance as characterized by membrane dialysis and orbitrap mass spectrometry. *Environmental Science & Technology*. 46(17): p. 9350-9.

(76) Haitzer, M., Aiken, G. R., Ryan, J. N. 2002. Binding of Hg to DOM the role of the Hg DOM ratio. *Environmental Science & Technology*. 36: p. 3564-3570.

(77) Mangal, V., Zhu, Y., Shi, Y. X., Guéguen, C. 2016. Assessing cadmium and vanadium accumulation using diffusive gradient in thin-films (DGT) and phytoplankton in the Churchill River estuary., Manitoba. *Chemosphere*. 163: p. 90-8.

(78) Le Faucheur, S., Campbell, P. G. C., Fortin, C., Slaveykova. 2014. Interactions between mercury and phytoplankton: speciation, bioavailability, and internal handling. *Environmental Toxicology & Chemistry.* 33(6): p. 1211-24.
(79) Leclerc, M., Planas, D., and Amyot, M. 2015. Relationship between Extracellular Low-Molecular-Weight Thiols and Mercury Species in Natural Lake Periphytic Biofilms. *Environmental Science & Technology.* 49(13): p. 7709-16.
(80) Diez, E. G., Loizeau, J. L., Cosio, C., Bouchet, S., Adatte, T., et al. 2016. Role of Settling Particles on Mercury Methylation in the Oxic Water Column of Freshwater Systems. *Environmental Science & Technology.* 50(21): p. 11672-11679.
(81) Johnstone, T. C. and Nolan, E. M. 2015. Beyond iron: non-classical biological functions of bacterial siderophores. *Dalton Transactions.* 44(14): p. 6320-39.
(82) Hughes, E. A., and Cresswell, P. 1998. The thiol oxireductase ERp57 is a component of the MHC class I peptide-loading complex. *Current Biology.* 8(12): p. 709-713.
(83) Cortez-Rocha, M. O., Trigo-Stockli, D. M., Wetzel, D. L., Reed, C. R. 2002. Effect of extrusion processing on fumonisin B(1) and hydrolyzed fumonisin B(1) in contaminated alkali-cooked corn. *Bull Environ Contam Toxicol.* 69(4): p. 471-8.
(84) Everall, N.C.L., and Lees, D. R. 1997. The identification and signifigance of chemicals released from decomposing barley straw during reservoir algal control. *Water Research.* 31(3): p. 614-620.
(85) Michaelson, L. V., Dunn, T. M., Napier, J. A. 2010. Viral trans-dominant manipulation of algal sphingolipids. *Trends Plant Science.* 15(12): p. 651-5.
(86) Rossolini, G. M., and Docquier, J. D. 2006. New beta-lactamases a paradigm for the rapid response of bacterial evolution in the clinical setting. *Future Microbiology.* 1(2): p. 295-308.
(87) Kumar B, Smita K., Cumbal L., Debut A. 2015. Green synthesis and characterization of silver nanoparticles using Andean blackberry fruit extract. *Saudi Journal of Biological Sciences.* 24(1):45-50.
(88) Singh P. K. 1975. Sensitization of algal virus to UV by the incorporation of 5-bromouracil and mutations of host alga Plectonema boryanum. *Journal of Basic Microbiology.* 75(7):547-52.
(89) Laboratory techniques in Biochemistry and Molecular Biology: Chapter 1 Lipids. 1972. Volume 3, page 342.
(90) Everall N. O and Lees D. R. 1997—The identification and significance of chemicals released from decomposing barley straw during reservoir algal control. *Water Research.* 31(3): 614-620.
(91) Bagwell C. E., Piskorska M, Soule T, Petelos A, Yeager C. M. 2014. A diverse assemblage of indole-3-acetic acid producing bacteria associated with unicellular green algae. *Applied Biochemistry and Biotechnology.* 173(8): 1977-84.
(92) Choi K. J., Nakhost Z., Barzana E., Karel M. 1987. Lipid content and fatty acid composition of green algae Scenedesmus obliquus grown in a constant cell density apparatus. *Food Biotechnology.* 1(1):117-28.
(93) Kurepa J., Nakabayashi R., Paunesku T., Suzuki M., Saito K., et al. 2014. Direct isolation of flavonoids from plants using ultra-small anatase $TiO_2$ nanoparticles. *The Plant Journal.* 77(3):443-53.
(94) Abdel-Aal E., Haroon M, A., Mofeed J. 2015. Successive solvent extraction and GC-MS analysis for the evaluation of the phytochemical constituents of the filamentous green alga Spirogyra longata. *The Egyptian Journal of Aquatic Research.* 41(3): 233-46.
(95) Vestola J., Shishido T. K., Jokela J., Fewer D. P., Aitio O., Permi P., et al. 2014. Hassallidins antifunfal glycolipopeptides are widespread among cyanobacteria and are the end product of a nonribsomal pathway. *Proceedings of the National Academy of Sciences.* 111(18): E1909-17.
(96) Michaelson L. V., Dunn T. M., Napier J. A. 2010. Viral trans-dominant manipulation of algal sphingolipids. *Trends in Plant Science.* 15:651-55
(97) Rossolini G. M., Docquier J. D. 2006. New b lactamases: a paradigm for the rapid response of bacterial evolution in the clinical setting. *Future Microbiology.* 1:295-308.
(98) Prince L. P., Gallant J. A. 1983—The glucose effect in Bacillus subtilis. *European Journal of Biochemistry.* 134: 105-7.
(99) Yamamoto M., Baldermann S., Keisuke Y., Fujita A., Mase N., Watanabe N. 2014. Determination of volatile compounds in four commercial samples of Japanese green algae using SPE GC-MS. *The Scientific World Journal.* 2014:1-8.
(100) Bauersachs 2010 (Thesis) Development and application of proxies for past cyanobacterial N2 fixation.
(101) Schmerk, C. L., Welander, P. V, Hamad, M. A., Bain, K. L., Bernards, M. A., Summons, R. E., Valvano, M. A., 2015. Elucidation of the *Burkholderia cenocepacia* hopanoid biosynthesis pathway uncovers functions for conserved proteins in hopanoid-producing bacteria. Environ. Microbiol. 17, 735-50. doi:10.1111/1462-2920. 12509.
(102) Percopo, I., Siano, R., Rossi, R., Soprano, V., Sarno, D., Zingone, A., 2013. A new potentially toxic Azadinium species (Dinophyceae) from the Mediterranean Sea, *A. dexteroporum* sp. nov. J. Phycol. 49, n/a-n/a. doi:10.1111/ jpy.12104.
(103) Müller, D., Krick, A., Kehraus, S., Mehner, C., Hart, M., Küpper, F. C.,
Saxena, K., Prinz, H., Schwalbe, H., Janning, P., Waldmann, H., König, G. M., 2006. Brunsvicamides A-C: Sponge-Related Cyanobacterial Peptides with *Mycobacterium tuberculosis* Protein Tyrosine Phosphatase Inhibitory Activity. J. Med. Chem. 49, 4871-4878. doi:10.1021/ jm060327w.

The invention claimed is:

1. A method of binding a metal ion in water, the method comprising:
   contacting the water with a fraction of dissolved organic material (DOM) to form a complex between the DOM fraction and the metal ion; and
   separating the complex from the water,
   wherein the fraction of DOM is a high molecular weight organic compound fraction of the DOM (HMW-DOM) having molecular weights ranging from 1800-3500 Da or a low molecular weight organic compound fraction of the DOM (LMW-DOM) having molecular weights ranging from 150-900 Da,
   and
   wherein the DOM is from phytoplankton.

2. The method of claim 1, wherein the LMW-DOM comprises 3-methyldioxyindole, bellendine, linoleoyl, gluconapin, N-acetylleucyl-leucyl-methionianal, aminopentol, momordicilin, sulfanilamide, dihydroxypentatriaconta-2,4-dienoic acid, an oligo peptide (e.g. Ala-Thr-Leu-His; L-leucyl-L-asparaginylglycyl-L-lysyl-L-alanyl-L-leucyl-L-valyl-L-glutamic acid; L-leucyl-L-asparaginylglycyl-L-lysyl-L-alanyl-L-leucyl-L-valyl-L-glutamic acid; and/or L-valyl-L-asparaginyl-L-isoleucyl-L-glutaminyl-L-lysyl-L-α-glutamyl-L-isoleucine), 2-hydroxyheptanoic acid, (E)-penta-1,3-dien-2-ol, a diglyceride, glycerol triaprylate, 5,7,3',4'-tetrahydroxy-3,6,5'-trimethoxyflavone, 9-octadecenoic acid, 1,2,3,4-tetrakis-o-(4-nitrobenzoyl)pentopyranose, ceramide, cefsulodin monobactam, 2,7,9-tricarboxypyrrolo(2,3-f)quinoline-4-ol-5-one, tetradecane-1, 1-(O-alpha-D-glucopyranosyl)-3-keto-(1,25R,27R)-octacosanetriol, 2,4-bis[4,5-bis(pentylamino)isoquinolin-1-yl]cyclobutane-1,3-dione, bacteriohopanetetrol cyclitol ether, azaspiracid-3, brunsvicamide A, siderochelin A, benarthin, chrysobactin, dihydroxybenzoic acid, rhizobactin, schizokinen, desferrioxamine, cyclic trichrisobactin, carboxymycobactin, exochelin, vibrioferrin, acinetoferrin, ferrioxamine or mixtures thereof.

3. The method of claim 1, wherein the method is for remediation of wastewater having a metal ion to be removed and the water is wastewater.

4. The method of claim 3, wherein the wastewater is domestic wastewater, urban wastewater, industrial wastewater or combinations thereof.

5. The method of claim 4, wherein the industrial wastewater comprises effluent from a mining operation.

6. The method of claim 1, wherein the separation comprises contacting the complex with a microorganism to sequester the complex.

7. The method of claim 1, wherein the phytoplankton is a *Chlorella* sp., a *Chlamydomonas* sp., a *Euglena* sp., a diatom, a cyanobacteria, a protist or mixtures thereof, and/or the phytoplankton is *Chlorella vulgaris, Chlamydomonas reinhardtii, Euglena gracilis, Euglena mutabilis, Scenedesmus obliquus, Thalassiosira weissflogii* or combinations thereof.

8. The method of claim 7, wherein the phytoplankton is *Euglena gracilis*.

9. The method of claim 1, wherein the DOM fraction is isolated from DOM by field-flow filtration, ultrafiltration or ultracentrifugation.

10. The method of claim 9, wherein the DOM fraction is isolated from DOM by a method comprising field-flow filtration.

11. The method of claim 9, wherein the DOM is produced under conditions suitable to obtain an increased percentage of one or more desired metal ion-binding compounds in the DOM fraction.

12. The method of claim 11, wherein the conditions comprise growing a culture of phytoplankton under conditions suitable to obtain the increased percentage of one or more desired metal ion-binding compounds in the DOM fraction.

13. The method of claim 12, wherein the conditions comprise one or more of a desired medium, temperature, light, pH, ionic strength and metal concentration.

14. The method of claim 13, wherein the conditions comprise varying the light regime.

15. The method of claim 1, wherein the metal ion is a rare earth element, a divalent metal, a transition metal, or a divalent transition metal.

16. The method of claim 1, wherein the metal ion is $Hg^{2+}$ or $Cd^{2+}$.

17. The method of claim 1, wherein the LMW-DOM comprises molecular weights ranging from 300-900 Da.

* * * * *